(12) United States Patent
Vangbo et al.

(10) Patent No.: US 8,748,165 B2
(45) Date of Patent: *Jun. 10, 2014

(54) METHODS FOR GENERATING SHORT TANDEM REPEAT (STR) PROFILES

(75) Inventors: Mattias Vangbo, Fremont, CA (US);
William D. Nielsen, San Jose, CA (US);
Iuliu I. Blaga, Fremont, CA (US);
Michael Van Nguyen, San Diego, CA (US); Steven B. Jovanovich, Livermore, CA (US)

(73) Assignee: IntegenX Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/590,965

(22) Filed: Aug. 21, 2012

(65) Prior Publication Data

US 2013/0053255 A1 Feb. 28, 2013

Related U.S. Application Data

(63) Continuation of application No. 12/321,594, filed on Jan. 21, 2009.

(60) Provisional application No. 61/022,722, filed on Jan. 22, 2008, provisional application No. 61/140,602, filed on Dec. 23, 2008.

(51) Int. Cl.
*C12M 3/00* (2006.01)
*C12M 1/34* (2006.01)

(52) U.S. Cl.
USPC .................. 435/287.2; 435/287.1; 435/287.3; 435/288.5; 435/288.7; 422/50; 422/81; 422/68.1; 422/502; 436/63; 436/94

(58) Field of Classification Search
USPC .............. 204/453, 604; 435/6.12, 6.16, 91.2, 435/287.1, 287.2, 287.3, 288.7, 288.5; 436/63, 94

See application file for complete search history.

(56) References Cited

U.S. PATENT DOCUMENTS

| | | | |
|---|---|---|---|
| 3,190,310 A | 6/1965 | Honsinger |
| 3,352,643 A | 11/1967 | Ando et al. |
| 3,433,257 A | 3/1969 | Jensen |
| 3,568,692 A | 3/1971 | Metzger et al. |
| 3,610,274 A | 10/1971 | Levesque et al. |
| 4,113,665 A | 9/1978 | Law et al. |
| 4,558,845 A | 12/1985 | Hunkapiller |
| 4,703,913 A | 11/1987 | Hunkapiller |

(Continued)

FOREIGN PATENT DOCUMENTS

| | | |
|---|---|---|
| CA | 2433145 A1 | 5/2002 |
| EP | 0459241 B1 | 12/1991 |

(Continued)

OTHER PUBLICATIONS

U.S. Appl. No. 13/590,051, filed Feb. 6, 2012, Vangbo et al.

(Continued)

*Primary Examiner* — Michael Marcheschi
*Assistant Examiner* — Shanta G Doe

(57) ABSTRACT

This invention provides a method for generating short tandem repeat (STR) profiles on each of a plurality of samples comprising, for each sample: a) isolating DNA from the sample; b) amplifying STR markers in the isolated DNA and c) analyzing the amplification product by electrophoresis.

27 Claims, 53 Drawing Sheets

(56) References Cited

U.S. PATENT DOCUMENTS

| | | |
|---|---|---|
| 4,847,120 A | 7/1989 | Gent |
| 4,963,498 A | 10/1990 | Hillman et al. |
| 5,085,757 A | 2/1992 | Karger et al. |
| 5,275,645 A | 1/1994 | Ternoir et al. |
| 5,364,759 A | 11/1994 | Caskey et al. |
| 5,376,252 A | 12/1994 | Ekström et al. |
| 5,387,505 A | 2/1995 | Wu |
| 5,453,163 A | 9/1995 | Yan |
| 5,482,836 A | 1/1996 | Cantor et al. |
| 5,523,231 A | 6/1996 | Reeve |
| 5,571,410 A | 11/1996 | Swedberg et al. |
| 5,587,128 A | 12/1996 | Wilding et al. |
| 5,635,358 A | 6/1997 | Wilding et al. |
| 5,639,428 A | 6/1997 | Cottingham |
| 5,675,155 A | 10/1997 | Pentoney et al. |
| 5,681,946 A | 10/1997 | Reeve |
| 5,705,628 A | 1/1998 | Hawkins |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,776,748 A | 7/1998 | Singhvi et al. |
| 5,830,662 A | 11/1998 | Soares et al. |
| 5,842,787 A | 12/1998 | Kopf-sill et al. |
| 5,856,174 A | 1/1999 | Lipshutz et al. |
| 5,863,502 A | 1/1999 | Southgate et al. |
| 5,872,010 A | 2/1999 | Karger et al. |
| 5,885,470 A | 3/1999 | Parce et al. |
| 5,898,071 A | 4/1999 | Hawkins |
| 5,900,130 A | 5/1999 | Benvegnu |
| 5,908,552 A | 6/1999 | Zimmerman et al. |
| 5,922,591 A | 7/1999 | Anderson et al. |
| 5,942,443 A | 8/1999 | Parce et al. |
| 5,948,684 A | 9/1999 | Weigl et al. |
| 5,971,158 A | 10/1999 | Yager et al. |
| 5,994,064 A | 11/1999 | Staub et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,110,343 A | 8/2000 | Ramsey et al. |
| 6,120,184 A | 9/2000 | Laurence et al. |
| 6,136,212 A | 10/2000 | Mastrangelo et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,342,142 B1 | 1/2002 | Ramsey |
| 6,348,318 B1 | 2/2002 | Valkirs |
| 6,379,929 B1 | 4/2002 | Burns et al. |
| 6,387,234 B1 | 5/2002 | Yeung et al. |
| 6,387,707 B1 | 5/2002 | Seul et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,191 B2 | 8/2002 | Schutt |
| 6,432,290 B1 | 8/2002 | Harrison et al. |
| 6,454,924 B2 | 9/2002 | Jedrzejewski et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,527,003 B1 | 3/2003 | Webster |
| 6,531,041 B1 | 3/2003 | Cong et al. |
| 6,531,282 B1 | 3/2003 | Dau et al. |
| 6,532,997 B1 | 3/2003 | Bedingham et al. |
| 6,533,914 B1 | 3/2003 | Liu |
| 6,534,262 B1 | 3/2003 | Mckernan et al. |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,581,899 B2 | 6/2003 | Williams |
| 6,605,454 B2 * | 8/2003 | Barenburg et al. ........ 435/173.7 |
| 6,613,525 B2 | 9/2003 | Nelson et al. |
| 6,614,228 B2 | 9/2003 | Hofmann et al. |
| 6,618,679 B2 | 9/2003 | Loehrlein |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,663,833 B1 | 12/2003 | Stave et al. |
| 6,685,442 B2 | 2/2004 | Chinn et al. |
| 6,685,809 B1 | 2/2004 | Jacobson et al. |
| 6,705,345 B1 | 3/2004 | Bifano |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,063,304 B2 | 6/2006 | Leys |
| 7,087,380 B2 | 8/2006 | Griffiths et al. |
| 7,097,809 B2 | 8/2006 | Van Dam et al. |
| 7,118,910 B2 | 10/2006 | Unger et al. |
| 7,157,228 B2 | 1/2007 | Hashmi et al. |
| 7,169,557 B2 | 1/2007 | Rosenblum et al. |
| 7,198,759 B2 | 4/2007 | Bryning et al. |
| 7,211,388 B2 | 5/2007 | Cash et al. |
| 7,232,656 B2 | 6/2007 | Balasubramanian et al. |
| 7,244,961 B2 | 7/2007 | Jovanovich et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,323,305 B2 | 1/2008 | Leamon et al. |
| 7,329,388 B2 * | 2/2008 | Guzman .................... 422/82.01 |
| 7,361,471 B2 | 4/2008 | Gerdes et al. |
| 7,377,483 B2 | 5/2008 | Iwabuchi et al. |
| 7,416,165 B2 | 8/2008 | Ohmi et al. |
| 7,438,856 B2 | 10/2008 | Jedrzejewski et al. |
| 7,445,926 B2 | 11/2008 | Mathies et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,537,886 B1 | 5/2009 | Nazarenko et al. |

(56) References Cited

U.S. PATENT DOCUMENTS

| | | |
|---|---|---|
| 7,575,865 B2 | 8/2009 | Leamon et al. |
| 7,645,580 B2 | 1/2010 | Barber et al. |
| 7,691,614 B2 | 4/2010 | Senapathy |
| 7,745,207 B2 | 6/2010 | Jovanovich et al. |
| 7,763,453 B2 | 7/2010 | Clemmens et al. |
| 7,766,033 B2 | 8/2010 | Mathies et al. |
| 7,799,553 B2 | 9/2010 | Mathies et al. |
| 7,803,281 B2 | 9/2010 | Davies |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 * | 1/2011 | Nasarabadi ............... 435/6.16 |
| 7,885,770 B2 | 2/2011 | Gill et al. |
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,972,561 B2 | 7/2011 | Viovy et al. |
| 7,976,789 B2 | 7/2011 | Kenis et al. |
| 7,976,795 B2 | 7/2011 | Zhou et al. |
| 8,007,746 B2 | 8/2011 | Unger et al. |
| 8,018,593 B2 | 9/2011 | Tan et al. |
| 8,037,903 B2 | 10/2011 | Wang et al. |
| 8,053,192 B2 | 11/2011 | Bignell et al. |
| RE43,122 E | 1/2012 | Harrison et al. |
| 8,222,023 B2 * | 7/2012 | Battrell et al. ............. 435/287.2 |
| 8,394,642 B2 | 3/2013 | Jovanovich et al. |
| 8,562,918 B2 | 10/2013 | Jovanovich et al. |
| 2001/0041357 A1 | 11/2001 | Fouillet et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2002/0127736 A1 | 9/2002 | Chou et al. |
| 2002/0139084 A1 | 10/2002 | Tobolka |
| 2002/0144738 A1 | 10/2002 | Unger et al. |
| 2002/0148992 A1 | 10/2002 | Hayenga et al. |
| 2002/0157951 A1 | 10/2002 | Foret et al. |
| 2002/0160361 A1 | 10/2002 | Loehrlein et al. |
| 2003/0008308 A1 | 1/2003 | Enzelberger et al. |
| 2003/0021734 A1 | 1/2003 | Vann et al. |
| 2003/0029724 A1 | 2/2003 | Derand et al. |
| 2003/0070677 A1 | 4/2003 | Handique et al. |
| 2003/0077839 A1 | 4/2003 | Takei |
| 2003/0095897 A1 | 5/2003 | Grate et al. |
| 2003/0104466 A1 | 6/2003 | Knapp et al. |
| 2003/0217923 A1 | 11/2003 | Harrison et al. |
| 2004/0003997 A1 | 1/2004 | Anazawa et al. |
| 2004/0013536 A1 | 1/2004 | Hower et al. |
| 2004/0014091 A1 | 1/2004 | Duck et al. |
| 2004/0018611 A1 | 1/2004 | Ward et al. |
| 2004/0021068 A1 | 2/2004 | Staats |
| 2004/0037739 A1 | 2/2004 | Mcneely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086870 A1 | 5/2004 | Tyvoll et al. |
| 2004/0086872 A1 | 5/2004 | Childers et al. |
| 2004/0132170 A1 | 7/2004 | Storek et al. |
| 2004/0151629 A1 | 8/2004 | Pease et al. |
| 2004/0185484 A1 | 9/2004 | Costa et al. |
| 2004/0197845 A1 | 10/2004 | Hassibi et al. |
| 2004/0200724 A1 | 10/2004 | Fujii et al. |
| 2004/0209354 A1 | 10/2004 | Mathies et al. |
| 2004/0224380 A1 | 11/2004 | Chou et al. |
| 2005/0026300 A1 | 2/2005 | Samper et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0161326 A1 | 7/2005 | Morita et al. |
| 2005/0161669 A1 | 7/2005 | Jovanovich et al. |
| 2005/0224134 A1 | 10/2005 | yin et al. |
| 2005/0224352 A1 | 10/2005 | Harrison et al. |
| 2005/0241941 A1 | 11/2005 | Parce et al. |
| 2005/0255000 A1 | 11/2005 | yamamoto et al. |
| 2005/0255003 A1 | 11/2005 | Summersgill et al. |
| 2005/0255007 A1 | 11/2005 | Yamada et al. |
| 2005/0266582 A1 | 12/2005 | Modlin et al. |
| 2005/0287572 A1 | 12/2005 | Mathies et al. |
| 2006/0027456 A1 | 2/2006 | Harrison et al. |
| 2006/0040300 A1 | 2/2006 | Dapprich et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0186043 A1 | 8/2006 | Covey et al. |
| 2006/0210994 A1 * | 9/2006 | Joyce ............................... 435/6 |
| 2006/0260941 A1 | 11/2006 | Tan et al. |
| 2006/0263789 A1 | 11/2006 | Kincaid |
| 2006/0266645 A1 | 11/2006 | Chen et al. |
| 2006/0292032 A1 | 12/2006 | Hataoka et al. |
| 2007/0015179 A1 | 1/2007 | Klapperich et al. |
| 2007/0017812 A1 | 1/2007 | Bousse |
| 2007/0031865 A1 | 2/2007 | Willoughby |
| 2007/0034025 A1 | 2/2007 | Pant et al. |
| 2007/0105163 A1 | 5/2007 | Grate et al. |
| 2007/0113908 A1 | 5/2007 | Lee et al. |
| 2007/0122819 A1 | 5/2007 | Wu et al. |
| 2007/0175756 A1 | 8/2007 | Nguyen et al. |
| 2007/0184463 A1 | 8/2007 | Molho et al. |
| 2007/0184547 A1 | 8/2007 | Handique et al. |
| 2007/0202531 A1 | 8/2007 | Grover |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0289941 A1 | 12/2007 | Davies |
| 2007/0297947 A1 | 12/2007 | Sommers et al. |
| 2008/0014576 A1 | 1/2008 | Jovanovich et al. |
| 2008/0014589 A1 | 1/2008 | Link et al. |
| 2008/0047836 A1 | 2/2008 | Strand et al. |
| 2008/0064610 A1 | 3/2008 | Lipovsek et al. |
| 2008/0124723 A1 | 5/2008 | Dale et al. |
| 2008/0138809 A1 | 6/2008 | Kapur et al. |
| 2008/0164155 A1 | 7/2008 | Pease et al. |
| 2008/0179255 A1 | 7/2008 | Jung et al. |
| 2008/0179555 A1 | 7/2008 | Landers et al. |
| 2008/0237146 A1 | 10/2008 | Harrison et al. |
| 2008/0242560 A1 | 10/2008 | Gunderson et al. |
| 2008/0257437 A1 | 10/2008 | Fernandes et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0023603 A1 | 1/2009 | Selden et al. |
| 2009/0035770 A1 | 2/2009 | Mathies et al. |
| 2009/0053799 A1 | 2/2009 | Chang-yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0092970 A1 | 4/2009 | Williams |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0178934 A1 | 7/2009 | Jarvius et al. |
| 2009/0181411 A1 | 7/2009 | Battrell et al. |
| 2009/0253181 A1 | 10/2009 | Vangbo et al. |
| 2009/0269504 A1 | 10/2009 | Liao |
| 2009/0286327 A1 | 11/2009 | Cho et al. |
| 2009/0311804 A1 | 12/2009 | Mcbrady et al. |
| 2009/0314972 A1 | 12/2009 | Mcavoy et al. |
| 2009/0325277 A1 | 12/2009 | Shigeura et al. |
| 2010/0068723 A1 | 3/2010 | Jovanovich et al. |
| 2010/0111770 A1 | 5/2010 | Hwang et al. |

(56) References Cited

U.S. PATENT DOCUMENTS

| | | |
|---|---|---|
| 2010/0129810 A1 | 5/2010 | Greiner et al. |
| 2010/0165784 A1 | 7/2010 | Jovanovich et al. |
| 2010/0172898 A1 | 7/2010 | Doyle et al. |
| 2010/0173398 A1 | 7/2010 | Peterman |
| 2010/0197507 A1 | 8/2010 | Rothberg et al. |
| 2010/0210008 A1 | 8/2010 | Strand et al. |
| 2010/0221726 A1 | 9/2010 | Zenhausern et al. |
| 2010/0224255 A1 | 9/2010 | Mathies et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0252123 A1 | 10/2010 | Mathies et al. |
| 2010/0266432 A1 | 10/2010 | Pirk et al. |
| 2010/0285578 A1 | 11/2010 | Selden et al. |
| 2010/0285606 A1 | 11/2010 | Philips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0326826 A1 | 12/2010 | Harrison et al. |
| 2011/0003301 A1 | 1/2011 | Raymond et al. |
| 2011/0005932 A1 | 1/2011 | Jovanovich et al. |
| 2011/0008813 A1 | 1/2011 | Dilleen et al. |
| 2011/0020920 A1 | 1/2011 | Mathies et al. |
| 2011/0027913 A1 | 2/2011 | Bau et al. |
| 2011/0038758 A1 | 2/2011 | Akaba et al. |
| 2011/0039303 A1 | 2/2011 | Jovanovich et al. |
| 2011/0045505 A1 | 2/2011 | Warthoe et al. |
| 2011/0048945 A1 | 3/2011 | Harrison et al. |
| 2011/0053784 A1 | 3/2011 | Unger et al. |
| 2011/0070578 A1 | 3/2011 | Bell et al. |
| 2011/0076735 A1 | 3/2011 | Jovanovich et al. |
| 2011/0124049 A1 | 5/2011 | Li et al. |
| 2011/0126910 A1 | 6/2011 | May |
| 2011/0127222 A1 | 6/2011 | Chang-yen et al. |
| 2011/0136179 A1 | 6/2011 | Bin/lee et al. |
| 2011/0137018 A1 | 6/2011 | Chang-yen et al. |
| 2011/0171086 A1 | 7/2011 | Prins et al. |
| 2011/0172403 A1 | 7/2011 | Harrold et al. |
| 2011/0189678 A1 | 8/2011 | Mcbride et al. |
| 2011/0206576 A1 | 8/2011 | Woudenberg et al. |
| 2011/0212440 A1 | 9/2011 | Viovy et al. |
| 2011/0212446 A1 | 9/2011 | Wang et al. |
| 2011/0223605 A1 | 9/2011 | Bienvenue et al. |
| 2011/0240127 A1 | 10/2011 | Eberhart et al. |
| 2011/0290648 A1 | 12/2011 | Majlof et al. |
| 2012/0115189 A1 | 5/2012 | Jovanovich et al. |
| 2012/0164036 A1 | 6/2012 | Stern et al. |
| 2012/0181460 A1 | 7/2012 | Eberhart et al. |
| 2012/0315635 A1 | 12/2012 | Vangbo et al. |

FOREIGN PATENT DOCUMENTS

| | | |
|---|---|---|
| EP | 0637999 A1 | 2/1995 |
| EP | 0527905 B1 | 11/1995 |
| EP | 1065378 B1 | 4/2002 |
| EP | 1411340 A2 | 4/2004 |
| EP | 1411340 A3 | 5/2004 |
| EP | 1345697 B1 | 6/2007 |
| EP | 1658890 B1 | 5/2008 |
| EP | 1345551 B1 | 4/2009 |
| EP | 2345739 A2 | 7/2011 |
| EP | 2345739 A3 | 10/2011 |
| JP | 2007-506430 A | 7/1995 |
| JP | 408327594 A | 12/1996 |
| JP | 2001-500966 A | 1/2001 |
| JP | 2001-521818 A | 11/2001 |
| JP | 2002-370200 A | 12/2002 |
| JP | 2003-536058 A | 12/2003 |
| JP | 2004-025159 A | 1/2004 |
| JP | 2004-108285 A | 4/2004 |
| JP | 2004-180594 A | 7/2004 |
| JP | 2005-323519 A | 11/2005 |
| JP | 2005-337415 | 12/2005 |
| JP | 2005-345463 A | 12/2005 |
| JP | 2007-155491 A | 6/2007 |
| JP | 2008-513022 A | 5/2008 |
| WO | WO 93/22053 A1 | 4/1993 |
| WO | WO 96/04547 A1 | 2/1996 |
| WO | WO 96/14934 A1 | 5/1996 |
| WO | WO 98/10277 A1 | 7/1997 |
| WO | WO 99/22868 A1 | 10/1998 |
| WO | WO 98/52691 A1 | 11/1998 |
| WO | WO 98/53300 A2 | 11/1998 |
| WO | WO 98/53300 A3 | 2/1999 |
| WO | WO 99/36766 A1 | 7/1999 |
| WO | WO 99/40174 A1 | 8/1999 |
| WO | WO 00/40712 A1 | 7/2000 |
| WO | WO 00/60362 A1 | 10/2000 |
| WO | WO 00/61198 A1 | 10/2000 |
| WO | WO 01/32930 A1 | 5/2001 |
| WO | WO 01/38865 A1 | 5/2001 |
| WO | WO 01/85341 A1 | 11/2001 |
| WO | WO 02/43864 A2 | 11/2001 |
| WO | WO 02/41995 A1 | 5/2002 |
| WO | WO 02/43615 A2 | 6/2002 |
| WO | WO 02/043864 A3 | 8/2002 |
| WO | WO 02/043615 A3 | 3/2003 |
| WO | WO 03/044528 A2 | 5/2003 |
| WO | WO 03/085379 A2 | 10/2003 |
| WO | WO 2004/038363 A2 | 5/2004 |
| WO | WO 03/044528 A3 | 6/2004 |
| WO | WO 2004/061085 A2 | 7/2004 |
| WO | WO 2004/061085 A3 | 10/2004 |
| WO | WO 2004/098757 A2 | 11/2004 |
| WO | WO 2004/038363 A3 | 12/2004 |
| WO | WO 2005/075081 A1 | 8/2005 |
| WO | WO 2005/091820 A2 | 10/2005 |
| WO | WO 2005/108620 A2 | 11/2005 |
| WO | WO 2005/118867 A2 | 12/2005 |
| WO | WO 2005/121308 A1 | 12/2005 |
| WO | WO 2006/032044 A2 | 3/2006 |
| WO | WO 2005/108620 A3 | 4/2006 |
| WO | WO 2004/098757 A3 | 5/2006 |
| WO | WO 2005/091820 A3 | 10/2006 |
| WO | WO 2006/032044 A3 | 1/2007 |
| WO | WO 2007/002579 A2 | 1/2007 |
| WO | WO2007/106579 * | 3/2007 |
| WO | WO 2007/064635 A1 | 6/2007 |
| WO | WO 2007/082480 A1 | 7/2007 |
| WO | WO 2007/109375 A2 | 9/2007 |
| WO | WO 2005/118867 A3 | 12/2007 |
| WO | WO 2008/012104 A2 | 1/2008 |
| WO | WO 2008/024319 A2 | 2/2008 |
| WO | WO 2008/024319 A3 | 4/2008 |
| WO | WO 2008/039875 A1 | 4/2008 |
| WO | WO 2008/012104 A3 | 5/2008 |
| WO | WO 2008/115626 A2 | 9/2008 |
| WO | WO 2007/109375 A3 | 10/2008 |
| WO | WO 2008/115626 A3 | 11/2008 |
| WO | WO 2009/008236 A1 | 1/2009 |
| WO | WO 2009/015296 A1 | 1/2009 |
| WO | WO 2007/002579 A3 | 9/2009 |
| WO | WO 2009/108260 A2 | 9/2009 |
| WO | WO 2009/129415 A1 | 10/2009 |
| WO | WO 2009/108260 A3 | 12/2009 |
| WO | WO 2010/041174 A1 | 4/2010 |
| WO | WO 2010/041231 A2 | 4/2010 |
| WO | WO 2010/042784 A2 | 4/2010 |
| WO | WO 2010/042784 A3 | 7/2010 |
| WO | WO 2010/041231 A3 | 9/2010 |
| WO | WO 2010/109392 A1 | 9/2010 |
| WO | WO 2010/130762 A2 | 11/2010 |
| WO | WO 2010/141921 A1 | 12/2010 |
| WO | WO 2011/003941 A1 | 1/2011 |
| WO | WO 2010/130762 A3 | 2/2011 |
| WO | WO 2011/012621 A1 | 2/2011 |
| WO | WO 2011/034621 A2 | 3/2011 |
| WO | WO 2011/084703 A2 | 7/2011 |
| WO | WO 2011/034621 A3 | 11/2011 |

OTHER PUBLICATIONS

Office action dates Sep. 19, 2012 for U.S. Appl. No. 12/321,594.

(56) References Cited

OTHER PUBLICATIONS

U.S. Appl. No. 12/026,510, filed Feb. 5, 2008, Jovanovich et al.
U.S. Appl. No. 13/202,877, filed Aug. 23, 2011, Vangbo et al.
U.S. Appl. No. 13/202,884, filed Aug. 23, 2011, Jovanovich et al.
U.S. Appl. No. 13/287,398, filed Nov. 2, 2011, Jovanovich et al.
U.S. Appl. No. 13/349,832, filed Jan. 13, 2012, Eberhart et al.
U.S. Appl. No. 13/367,326, filed Feb. 6, 2012, Jovanovich et al.
U.S. Appl. No. 13/384,753, filed Jan. 18, 2012, Stern et al.
U.S. Appl. No. 90/011,453, filed Jan. 21, 2011, Mathias et al.
Allowed Claims dated May 6, 2010 for U.S. Appl. No. 11/726,701.
Allowed Claims dated Jul. 1, 2010 for U.S. Appl. No. 11/139,018.
Allowed Claims dated Aug. 13, 2008 for U.S. Appl. No. 10/750,533.
Amendment and Request for Correction of Inventorship mailed Jan. 10, 2008 in U.S. Appl. No. 10/750,533.
Anderson, et al. A miniature integrated device for automated multistep genetic assays. Nucleic Acids Research. 2000;28:e60.
Armani, et al. Re-configurable fluid circuits by PDMS elastomer micromachining. Proceedings of IEEE Micro Electro Mechanical Systems: MEMS. 1999; 222-227.
Auroux, et al. Micro Total Analysis Systems 2. Analytical Standard Operations and Applications. Anal. Chem. 2002; 2637-2652.
Belgrader, et al. A Minisonicator to Rapidly Disrupt Bacterial Spores for DNA Analysis. Anal. Che. 1999; 4232-4236.
Belgrader, et al. PCR Detection of Bacteria in Seven Minutes. Science Magazin. 1999; 284(5413):449-450.
Belgrader, et al. Rapid PCR for Identity Testing Using a Battery-Powered Miniature Thermal Cycler. J Forensic Sci. 1998; 315-319.
Bennett, et al. Toward the 1,000 dollars human genome. Pharmacogenomics, 6 (4) 373-382. (Jun. 2005).
Bianco, et al. Teflon-like coatings for micro devices. CPAC Satellite Workshops. Rome, Italy. Mar. 23, 2009.
Bings, et al. Microfluidic Devices Connected to Fused-Silica Capillaries with Minimal Dead Dead Volume. Analytical Chemistry. 1999;71(15):3292-3296.
Birnboim. A Rapid Alkaline Extraction Method for the Isolation of Plasmid DNA. Methods of Enzymology. 1983; 100:243-255.
Blaga, et al. Microfluidic device for automated sample preparation. Poster. MSB Conference. Dalian, China. Oct. 2009.
Blaga, et al. Plastic chips with valves and pumps. MSB Conference. Berlin, Germany. Mar. 2008. Abstract only.
Blazej, et al. Inline injection microdevice for attomole-scale sanger DNA sequencing. Anal Chem. Jun. 15, 2007;79(12):4499-506. Epub May 12, 2007.
Blazej, et al. Microfabricated bioprocessor for integrated nanoliter-scale Sanger DNA sequencing. Proc. Natl. Acad. Sci. USA 2006;103:7240-7245.
Blazej, et al. Polymorphism Ratio Sequencing: A New Approach for Single Nucleotide Polymorphism Discovery and Genotyping. Genome Research. 2003;13:287-293.
Brenner, et al. Gene expression analysis by massively parallel signature sequencing (MPSS) on microbead arrays. Nature Biotechnology. 2000;18(6):630-634.
Buchholz, et al. The use of light scattering for precise characterization of polymers for DNA sequencing by capillary electrophoresis. Electrophoresis. 2001;22:4118-4128.
Burns, et al. An Integrated Nanoliter DBA Analysis Device. Science Magazine. 1998; 484-487.
Call, et al. Detecting and genotyping *Escherichia coli* 0157:H7 using multiplexed PCR and nucleic acid microarrays. International Journal of Food Microbiology. 2001; 67:71-80.
Cameron, et al. High Internal Phase Emulsions (HIPEs) Structure, Properties and Use in Polymer Preparation. University of Strathclyde. 1995; 163214.
Canadian Office Action dated Jun. 10, 2011 for CA Application No. 2512071.
Capanu, et al. Design Fabrication and Testing of a Bistable Electromagnetically Actuated Microvalve. Journal of Microelectromechanical System. 2000; 9:181-189.

CAPLUS abstract of Krokhin et al. Modified silica as a stationary phase for ion chromatography. Journal of Chromatography A. 1995;706:93-8.
Chan, et al. Microfabricated Polymer Devices for Automated Sample Delivery of Peptides for Analysis by Electrospray Ionization Tandem Mass Spectrometry. Analytical Chemistry. 1999;71(20):4437-4444.
Chandler, et al. Automated immunomagnetic separation and microarray detection of *E. coli* 0157:H7 from poultry carcass rinse. International Journal of Food Microbiology. 2001; 70:143-154.
Charlieu, et al. 3' Alu PCR: a simple and rapid method to isolate human polymorphic markers. Nucleic Acids Res. Mar. 25, 1992;20(6):1333-7.
Chiem, et al. Microchip systems for immunoassay: an integrated immunoreactor with electrophoretic separation for serum theophylline determination. Clinical Chemistry.1998;44(3):591-598.
Chiem, et al. Room temperature bonding of micromachined glass devices for capillary electrophoresis. Sensors and Actuators. 2000;B63(3):147-152.
Chinese office action dated Jan. 18, 2012 for CN 200980108368.7. (in Chinese with English translation).
Chinese Office Action dated Jan. 25, 2008 for Application No. 2003801100666.
Chinese office action dated Jan. 31, 2011 for CN 200580035911.7. (in Chinese with English translation).
Chinese office action dated Feb. 24, 2010 for CN Application No. 200780018073.1.
Coleman, et al. A sequential injection microfluidic mixing strategy. Microfluidics and Nanofluidics. 2005;319-327.
Curcio, et al. Continuous Segmented-Flow Polymerase Chain Reaction for High-Throughput Miniaturized DNA Amplification. Analytical Chemistry. 2003;75(1):1-7.
Datasheet Cycle Sequencing, Retrieved from the internet, URL:http//answers.com/topic/cycle sequencing. Printed Sep. 3, 2010, pp. 1-2.
Delehanty, et al. A Microarray Immunoassay for Simultaneous Detection of Proteins and Bacteria. Anal. Chem. 2002; 74:5681-5687.
Diehl, et al. BEAMing: single-molecule PCR on microparticles in water-in-oil emulsions. Nature Methods. 2006;3(7):551-9.
Dodson, et al. Fluidics Cube for Biosensor Miniaturization. Anal. Chem. 2001; 3776-3780.
Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.
Doherty, et al. Sparsely cross-linked "nanogels" for microchannel DNA sequencing. Electrophoresis. 2003;24(24):4170-4180.
Dorfman, et al. Contamination-Free Continuous Flow Microfluidic Polymerase Chain Reaction for Quantitative and Clinical Applications. Analytical Chemistry. 2005;77(11):3700-3704.
Doyle, et al. Self-Assembled Magnetic Matrices for DNA Separation Chips. Science. 2000;295:2237.
Dressman, et al. Transforming single DNA molecules into fluorescent magnetic particles for detection and enumeration of genetic variations. Proc Natl Acad Sci USA. 2003;100(15):8817-8822.
Duffy, et al. Rapid Prototyping of Microfluidic Systems in Poly(dimethylsiloxane). Anal. Chem. 1998; 4974-4984.
Emrich, et al. Microfabricated 384-Lane Capillary Array Electrophoresis Bioanalyzer for Ultrahigh-Throughput Genetic Analysis. Analytical Chemistry. 2002;74(19):5076-5083.
Ericson, et al. Electroosmosis- and Pressure-Driven Chromatography in Chips Using Continuous Beds. Analytical Chemistry. 2000;72(1):81-87.
Erratum for Margulies, et al. Genome sequencing in microfabricated high-density picolitre reactors. Nature. 2005;437(7057):376-80.: Margulies, et al. Nature. 441(7089):120. (May 4, 2006).
European office action dated Apr. 7, 2011 for EP Application No. 05804847.1.
European search report and search opinion dated Jun. 6, 2011 for Application No. 10011511.2.
European search report and search opinion dated Aug. 17, 2011 for Application No. 08799648.4.
European search report dated Dec. 18, 2009 for Application No. 03808583.3.

(56) References Cited

OTHER PUBLICATIONS

European search report dated Sep. 1, 2010 for Application No. 5804847.1.
Ewing, et al. Base-Calling of Automated Sequencer Traces Using Phred. I. Accuracy Assessment. Genome Research. 1998;8:175-185.
Ewing, et al. Base-Calling of Automated Sequencer Traces Using Phred. II. Error probabilities. Genome Research. 1998;8:186-194.
Figeys, et al. A Microfabricated Device for Rapid Protein Identification by Microelectrospray Ion Trap Mass Spectrometry. Analytical Chemistry. 1997;69(16):3153-3160.
Figeys, et al. An Integrated Microfluidics-Tandem Mass Spectrometry System for Automated Protein Analysis. Analytical Chemistry. 1998;70(18):3728-3734.
Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.
Figeys, et al. Nanoflow Solvent Gradient Delivery from a Microfabricated Device for Protein Identifications by Electrospray Ionization Mass Spectrometry. Analytical Chemistry. 1998;70(18):3721-3727.
Francis, et al. Flow analysis based on a pulsed flow of solution: theory, instrumentation and applications. Talanta. 2002;58(6):1029-1042.
Franklin, et al. Apollo 200: an integrated platform for DNA profiling. Poster. MCB Conference. Prague, Czech Republic. Mar. 2010.
Gau, et al. A MEMS based amperometric detector for *E. coli* bacteria using self-assembled monolayers. Biosensors & Bioelectronic. 2001; 16:745755.
Ghadessy, et al. Directed evolution of polymerase function by compartmentalized self-replication. Proc Natl Acad Sci USA. 2001;98:4552-4557.
Giddings, et al. A software system for data analysis in automated DNA sequencing. Genome Research. 1998;8:644-665.
Goll, et al. Microvalves with bistable buckled polymer diaphragms. Journal of Micromechanics and Microengineering. 1996;6:77-79.
Grover, et al. An integrated microfluidic processor for single nucleotide polymorphism-based DNA computing. Lab on a Chip. 2005;5(10):1033-1040.
Grover, et al. Development and multiplexed control of latching pneumatic valves using microfluidic logical structures. Lab on a chip. 2006;6:623-631.
Grover, et al. Monolithic membrane valves and diaphragm pumps for practical large-scale integration into glass microfluidic devices. Sensors and Actuators. 2003;B89:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.
Hansen, et al. Polymerase chain reaction assay for the detection of *Bacillus cereus* group cells. FEMS Microbology Letters. 2001; 202:209-213.
Harrison, et al. Micromachining a Miniaturized Capillary Electrophoresis-Based Chemical Analysis System on a Chip. Science. 1993;261(5123):895-897.
Hartmann, et al. Direct immobilization of antibodies on phthalocyaninato-polysiloxane photopolymers. Thin Solid Films. 1994; 245:206-210.
Hartmann, et al. One-step immobilization of immunoglobulin G and potential of the method for application in immunosensors. Sensors and Actuators. 1995; 28 (2):143-149.
Hayes, et al. EDGE: A Centralized Resource for the Comparison, Analysis, and Distribution of Toxicogenomic Information. Molecular Pharmacology. 2005;67(4):1360-1368.
He, et al. Fabrication of Nanocolumns for Liquid Chromatography. Anal. Chem. 1998; 3790-3797.
Hjerten. High-performance electrophoresis : Elimination of electroendosmosis and solute adsorption. J. Chromotography. 1985; 347:191-198.
Hosokawa, et al. A Pneumatically-Actuated Three-Way Microvalve Fabricated with Polydimcthylsiloxanc Using the Membrane Transfer Technique. J. Micinicch. Microcng. 2000; 10:415-420.
Hultman, et al. Bidirectional Solid-Phase Sequencing of In Vitro-Amplified Plasmid DNA. BioTechniques. 1991;10(1):84-93.
International Preliminary Report for corresponding PCT Application No. PCT/CA2000/01421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/007381 dated Sep. 23, 2008.
International Preliminary Report for corresponding PCT Application No. PCT/US2007/02721 dated Aug. 5, 2008.
International Preliminary Report for corresponding PCT Application No. PCT/US2007/061573 dated Aug. 26, 2008.
International search report and written opinion dated Oct. 29, 2007 for PCT/US2005/018678.
International search report and written opinion dated Mar. 16, 2012 for PCT/US2011/048528.
International search report and written opinion dated Mar. 24, 2011 for PCT Application No. US2010/58227.
International search report and written opinion dated Apr. 30, 2012 for PCT/US2012/021217.
International search report and written opinion dated Jun. 9, 2011 for PCT Application No. US2011/30973.
International search report and written opinion dated Jul. 15, 2008 for PCT/US2007/007381.
International search report and written opinion dated Sep. 1, 2010 for PCT Application No. US2010/040490.
International search report dated Sep. 1, 2010 for PCT/US2010/040490.
International search report dated Oct. 6, 2010 for PCT Application No. US10/37545.
International search report dated Apr. 5, 2001 for PCT Application No. CA2000/01421.
International search report dated May 14, 2010 for PCT Application No. US2009/06640.
International search report dated Jul. 11, 2008 for PCT Application No. US07/61573.
International search report dated Jul. 30, 2010 for PCT Application No. US2010/36464.
International search report dated Aug. 18, 2009 for PCT Application No. US09/00419.
International search report dated Aug. 23, 2006 for PCT Application No. US2005/033347.
International search report dated Aug. 26, 2004 PCT Application No. US2003/41466.
International search report dated Sep. 25, 2007 for PCT Application No. US2007/02721.
International Search Report for PCT/US2005/033347.
International written opinion dated Oct. 6, 2010 for PCT Application No. US10/37545.
International written opinion report dated Jul. 30, 2010 for PCT Application No. US2010/36464.
Jacobson, et al. Electrokinetic Focusing in Microfabricated Channel Structures. Anal. Chem., 1997, 69 (16), pp. 3212-3217.
Jacobson, et al. High-Speed Separations on a Microchip. Anal. Chem. 1994; 1114-1118.
Jacobson, et al. Integrated Microdevice for DNA Restriction Fragment Analysis Anal. Chem. 1996; 720-723.
Japanese Office Action dated Jan. 13, 2010 for JP Application No. 2005508628.
Japanese office action dated Mar. 1, 2011 for JP Application. No. 2007-515379.
Japanese office action dated May 11, 2012 for Application No. 2008-553535 (English translation).
Japanese office action dated May 27, 2011 for Application No. 2007-532553 (in Japanese with English translation).

(56) References Cited

OTHER PUBLICATIONS

Japanese office action dated Jul. 28, 2011 for Application No. 2008-553535 (in Japanese with English translation).
Japanese Office Action dated Aug. 10, 2010 for JP Application No. 2005508628.
Japanese Office Action dated Dec. 21, 2010 for Application No. JP2001-540363 (in Japanese with English translation).
Japanese Office Action dated Apr. 27, 2010 for Application No. JP2001-540363 (in Japanese with English translation).
Ju, et al. Fluorescence energy transfer dye-labeled primers for DNA sequencing and analysis. Proc. Natl. Acad. Sci. USA. 1995;92:4347-4351.
Kamei, et al. Integrated Amorphous Silicon Photodiode Detector for Microfabricaqted Capillary Electrophoresis Devices. Micro Total Analysis Systems. 2002; 257-259.
Kamei, et al. Integrated hydrogenated amorphous Si photodiode detector for microfluidic bioanalytical devices. Anal Chem. Oct. 15, 2003;75(20):5300-5.
Kan, et al. A novel thermogelling matrix for microchannel DNA sequencing based on poly-N-alkoxyalkylaclylamide copolymers. Electrophoresis. 2003;24(24):4161-4169.
Kimura, et al. Restriction-Site-Specific PCR as a Rapid Test to Detect Enterohemorrhagic *Escherichia coli* 0157:H7 Strains in Environmental Samples. Applied and Environmental Microbiology. Jun. 2000; 25132519.
Koch, et al. Optical flow-cell multichannel immunosensor for the detection of biological warfare agents. Biosens Bioelectron. Jan. 2000;14(10-11):779-84.
Koh, et al. Integrating Polymerase Chain Reaction, Valving, and Electrophoresis in a Plastic Device for Bacterial Detection. Analytical Chemistry. 2003;75(17):4591-4598.
Kong, et al. Rapid detection of six types of bacterial pathogens in marine waters by multiplex PCR. Water Research. 2002; 36: 2802-2812.
Kopp, et al. Chemical Amplification Continuous-Flow PCR on a Chip. Science. 1998;280:1046-1048.
Kourentzi, et al. Microbial identification by immunohybridization assay of artificial RNA labels. Journal of Microbiological Methods. 2002; 49:301-306.
Kuhnert, et al. Detection System for *Escherichia coli*-Specific Virulence Genes: Absence of Virulence Determinants in B and C Strains. applied and Environmental Microbiology. 1997:703-709.
Lagally, et al. Fully integrated PCR-capillary electrophoresis microsystem for DNA analysis. Lab on a Chip. 2001;1(2):102-107.
Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;B63(3):138-146.
Lagally, et al. Single-Molecule DNA Amplification and Analysis in an Integrated Microfluidic Device. Analytical Chemistry. 2001;73(3): 565-570.
Lazar, et al. Subattomole-Sensitivity Microchip Nanoelectrospray Source with Time-of-Flight Mass Spectrometry Detection. Analytical Chemistry. 1999;71(17):3627-3631.
Lee, et al. Polymer nanoengineering for biomedical applications. Annals Biomed. Eng. 2006; 34:75-88.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Li, et al. Rapid and sensitive separation of trace level protein digests using microfabricated devices coupled to a quadrupole—time-of-flight mass spectrometer. Electrophoresis. 2000;21:198-210.
Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.
Licklider, et al. A Micromachined Chip-Based Electrospray Source for Mass Spectrometry. Analytical Chemistry. 2000;72(2):367-375.
Ligler, et al. Integrating Waveguide Biosensor. Anal Chem. Feb. 1, 2002;74(3):713-9.
Lisec, et al. A bistable pneumatic microswitch for driving fluidic components. Sensors and Actuators. 1996;A54:746-749.
Liu, et al. Automated parallel DNA sequencing on multiple channel microchips. Proc. Natl. Acad. Sci. USA. 2000;97(10):5369-5374.
Liu, et al. Optimization of High-Speed DNA Sequencing on Microfabricated Capillary Electrophoresis Channels. Analytical Chemistry. 1999;71:566-573.
Lu, et al. New valve and bonding designs for microfluidic biochips containing proteins. Anal. Chem. 2007; 79:994-1001.
Manz, et al. Miniaturized Total Chemical Analysis Systems: A Novel Concept for Chemical Sensing. Sensors & Actuators. 1990; 244-248.
Margulies, et al. Genome sequencing in microfabricated high-density picolitre reactors. Nature. 2005;437(7057):376-80.
McLaughlin, et al. Molecular Approaches to the Identification of *Streptococci*. Methods in Molecular Medicine. 1998; 15:117-139.
Medintz, et al. Genotyping Energy-Transfer Cassette Labeled Short Tandem Repeat Amplicons with Capillary Array Electrophoresis Microchannel Plates. Clinical Chemistry. 2001; 1614-1621.
Medintz, et al. High-Performance Genetic Analysis Using Microfabricated Capillary Array Electroporesis Microplates. Electrophoresis. 2001; 38453856.
Medintz, et al. High-Performance Multiplex SNP Analysis of Three Hemochmromatosis-Related Mutations with Capillary Array Electrophoresis Microplates. Genome Research. 2001; 413-421.
Medintz, et al. Novel Energy Transfer Fluorescence Labeling Cassette. BioTechniques. 2002; 32(2):270.
Melin, et al. A Passive 2-Dimensional Liquid Sample Micromixer. 7th International Conference on Miniaturized Chemical and Biochemical Analysis Systems. 2003;167-170.
MillGat pump user manual, version 2.12, published 2005, pp. 1-28.
Mitra, et al. Digital genotyping and haplotyping with polymerase colonies. Proc Natl Acad Sci USA. 2003.100(10):15926-5931.
Nataro, et al. Diarrheagenic *Escherichia coli*. Clinical MicroBiology Reviews. Jan. 1998;142-201.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.
Notice of Allowance dated May 6, 2010 for U.S. Appl. No. 11/726,701.
Notice of allowance dated Jun. 9, 2011 for U.S. Appl. No. 12/831,949.
Notice of Allowance dated Jul. 1, 2010 for U.S. Appl. No. 11/139,018.
Notice of Allowance dated Aug. 13, 2008 for U.S. Appl. No. 10/750,533.
Notice of allowance dated Sep. 8, 2011 for U.S. Appl. No. 12/820,390.
Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.
Ocvirk, et al. High Performance Liquid Chromatography Partially Integrated onto a Silicon Chip. Analytical Methods and Instrumentation. 1995;2:74-82.
Ocvirk, et al. Optimization of confocal epifluorescence microscopy for microchip-based miniaturized total analysis systems. The Analyst. 1998;123:1429-1434.
Office action dated Jan. 7, 2011 for U.S. Appl. No. 12/844,544.
Office action dated Jan. 20, 2010 for U.S. Appl. No. 11/978,224.
Office action dated Feb. 22, 2010 for U.S. Appl. No. 11/139,018.
Office action dated Mar. 2, 2008 for U.S. Appl. No. 10/540,658.
Office action dated Mar. 29, 2012 for U.S. Appl. No. 12/789,186.
Office action dated Mar. 30, 2012 for U.S. Appl. No. 12/795,515.
Office action dated Apr. 11, 2012 for U.S. Appl. No. 11/139,018.
Office action dated Apr. 29, 2009 for U.S. Appl. No. 11/139,018.
Office action dated May 22, 2012 for U.S. Appl. No. 12/526,015.
Office action dated Aug. 27, 2008 for U.S. Appl. No. 11/139,018.

(56) References Cited

OTHER PUBLICATIONS

Office action dated Oct. 8, 2008 for U.S. Appl. No. 10/540,658.
Office action dated Oct. 25, 2010 for U.S. Appl. No. 11/978,224.
Office action dated Nov. 6, 2009 for U.S. Appl. No. 11/139,018.
Office action dated Dec. 11, 2009 for U.S. Appl. No. 11/726,701.
Office action dates Dec. 7, 2012 for U.S. Appl. No. 13/590,051.
Office Action Final dated Feb. 19, 2008 issued in U.S. Appl. No. 10/540,658.
Office Action Final dated Feb. 6, 2008 issued in U.S. Appl. No. 11/139,018.
Office Action mailed Apr. 27, 2007 in U.S. Appl. No. 11/139,018, filed May 25, 2005.
Office Action mailed Jul. 2, 2007 in U.S. Appl. No. 10/540,658, filed Jun. 23, 2005.
Office Action mailed Jul. 12, 2007 in U.S. Appl. No. 10/750,533, filed Dec. 29, 2003.
Oh, et al. A review of microvalves. J. Micromech. Microeng. 2006; 16:R13-R39.
Ohori, et al. Partly disposable three-way mirovalve for a medical micro total analysis system (muTAS). Sensors and Actuators. 1998;A64(1): 57-62.
Oleschuk, et al. Trapping of Bead-Based Reagents within Microfluidic Systems: On-Chip Solid-Phase Extraction and Electrochromatography. Analytical Chemistry. 2000;72:585-590.
Olsen, et al. Immobilization of DNA Hydrogel Plugs in Microfluidic Channels. Analytical Chemistry. 2002;74:1436-1441.
O'Mahony, et al. A real time PCR assay for the detection and quantitation of *Mycobacterium avium* subsp. Paratuberculosis using SyBR Green and the Light Cycler. Journal of Microbiological Methods. 2002; 51:283-293.
Paegel, et al. High-throughput DNA sequencing with a 96-lane capillary array electrophoresis bioprocessor. Proc Natl Acad Sci USA. 2002;99:574-579.
Paegel, et al. Microchip Bioprocessor for Integrated Nanovolume Sample Purification and DNA Sequencing. Analytical Chemistry. 2002;74(19):5092-5098.
Paegel, et al. Microfluidic devices for DNA sequencing: sample preparation and electrophoretic analysis. Current Opinion in Biotechnology. 2003;14(1):42-50.
Paegel, et al. Turn Geometry for Minimizing Band Broadening in Microfabricated Capillary Electrophoresis Channels. Analytical Chemistry. 2000;72:3030-3037.
Papadelli, et al. Rapid detection and identification of *Streptococcus macedonicus* by species-specific PCR and DNA hybridisation. International Journal of Food Microbiology. 2003; 81:231-239.
PCT Notification of Transmittal of the International Search Report and The Written Opinion of the International Searching Authority, or the Declaration, mailed Jun. 17, 2008, Application No. PCT/US2007/082568.
Peng, et al. Immuno-capture PCR for detection of Aeromonas hydrophila Journal of Microbiological Methods. 2002; 49:335-338.
Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.
Press, et al., An Integrated Microfluidic Processor for Single Nucleotide Polymorphism-based DNA Computing, Lab on a Chip. 2005, 5:10, 8 pages.
Press, et al., The Art of Scientific Computing, Numerical Recipes in C, 2nd Edition, Cambridge University Press, 1992, (table of Contents).
Quake, et al. From Micro-to Nanofabrication with Soft Materials. Science Magazine. 2000; 1536-1540.
Ramsey, et al. Generating Electrospray from Microchip Devices Using Electroosmotic Pumping. Analytical Chemistry. 1997;69(6):1174-1178.
Reyes, et al. Micro Total Analysis Systems. 1. Introduction Theory and Technology. Anal Chem. 2002; 2623-2636.
Rohr, et al. Porous polymer monoliths: Simple and efficient mixers prepared by direct polymerization in the channels of microfluidic chips. Electrophoresis. 2001;22:3959-3967.
Roth, et al. Fundamentals of Logic Design, 3rd Edition, West Publishing Company, 1985 (Table of Content).
Rowe, et al. Array Biosensor for Simultaneous Identification of Bacterial, Viral and Protein Analytes. Anal. Chem. 1999; 71:3846-3852.
Rowe-Taitt, et al., Simultaneous detection of six biohazardous agents using a planar waveguide array biosensor. Biosensors & Bioelectronics. 2000; 15:579-589.
Ruan, et al. Immunobiosensor Chips for Detection of *Escherichia coli* 0157:H7 Using Electrochemical Impedance Spectroscopy. Anal. Chem. 2002; 74:4814-4820.
Rye, et al. High-sensitivity two-color detection of double-stranded DNA with a confocal fluorescence gel scanner using ethidium homodimer and thiazole orange. Nucleic Acids Research. 1991;19(2):327-333.
Samel. Novel Microfluidic devices based on a thermally responsive PDMS composite. KTH Royal Institute of Technology, Stockholm, Sweden. 2007; 1-80.
Sanford, et al. Photoactivatable Cross-Linked Polyacrylamide for the Site-Selective Immobilization of Antigens and Antibodies Chem Mater. 1998; 10(6): 15101520.
Scherer, et al. High-Pressure Gel Loader for Capillary Array Electrophoresis Microchannel Plates. Biotechniques. 2001;31(5):1150-1154.
Schomburg, et al. Design Optimization of Bistable Microdiaphragm Valves. Sensors and Actuators. 1998;A64:259-264.
Seifar, et al. Capillary electrochromatography with 1.8-mum ODS-modified porous silica particles. Journal of Chromatography. 1998; A808:71-77.
Shi, et al. Radial Capillary Array Electrophoresis Microplate and Scanner for High Performance Nucleic Acid Analysis. Anal. Chem. 1999; 5354-5361.
Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Soper, et al. Polymeric Microelectro-mechanical Systems. Anal. Chem 2000; 643-651.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Stumpfle, et al. Absence of DNA sequence homology with genes of the *Escherichia coli* hemB locus in Shiga-toxin producing *E. coli* (STEC) 0157 Strains. FEMS Microbiology Letters. 1999; 174:97-103.
Sun, et al. A Heater-Integrated Transparent Microchannel Chip for Continuous Flow PCR. Sensors and Actuators B. 2002; 84:283-289.
Tajima, et al. Physiochemical properties and morphology of fluorocarbon films synthesized on crosslinked polyethylene by capacitively coupled octafluorocyclobutane plasma. J. Phys. Chem. C. 2007; 111(11):4358-4367.
Takao, et al. A Pneumatically Actuated Full In-Channel Microvalve With MOSFET-Like Function in Fluid Channel Networks. Journal of Microelectromechanical Systems. 2002;11(5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Thomas, et al. Application of Genomics to Toxicology Research. Environmental Health Perspectives. 2002;110(6):919-923.
Thorsen, et al. Microfluidic Large-Scale Integration. Science. 2002;298(5593):580-584.
Tian, et al. Evaluation of Silica Resins for Direct and Efficient Extraction of DNA from Complex Biological Matrices in a Miniaturized Format. Analytical Biochemistry. 2000; 283:175-191.

(56) References Cited

OTHER PUBLICATIONS

Tice, et al. Formation of Droplets and Mixing in Multiphase Microfluidics at Low Values of the Reynolds and the Capillary Numbers. Langmuir. 2003;19:9127-9133.
Unger, et al. Monolithic Microfabricated Valves and Pumps by Multilayer Soft Lithography. Science. 2000;288:113-116.
Van Der Moolen, et al. A Micromachined Injection Device for CZE: Application to Correlation CZE. Analytical Chemistry. 1997;69(20):4220-4225.
Van Der Moolen, et al. Correlation Capillary Zone Electrophoresis, a Novel Technique to Decrease Detection Limits. Chromatographia. 1995;40(7/8):368-374.
Vazquez, et al. Electrophoretic Injection within Microdevices. Analytical Chemistry. 2002;74:1952-1961.
Veenstra, et al. The design of an in-plane compliance structure for microfluidical systems. Sensors and Actuators. 2002;B81:377-383.
Verlee, et al. .Fluid Circuit Technology: Integrated Interconnect Technology for Miniature Fluidic Devices. Abbott Laboratories Hospital Division, Abbott Park, IL. 1996; 9-14.
Waller, et al. Quantitative Immunocapture PCR Assay for Detection of Campylobacter jejuni in Foods. Applied Environmental Microbiology. 2000; 66(9):4115-4118.
Walt, et al. Biological Warefare Detection. Analytical Chemistry 2000; 739-746.
Waters, et al. Microchip Device for Cell Lysis, Multiplex PCR Amplification, and Electrophoretic Sizing. Anal. Chem. 1999; 158-162.
Webster, et al. Monolithic Capillary Electrophoresis Device with Integrated Fluorescence Detector. Anal. Chem. 2001;1622-1626.
Weimer, et al. Solid-Phase Capture of Proteins, Spores, and Bacteria. Applied Environmental Microbiology. 2001;67(3):1300-1307.
Wen, et al. Microfabricated isoelectric focusing device for direct electrospray ionization-mass spectrometry. Electrophoresis. 2000;21:191-197.
White, et al. Flash detection/identification of pathogens, bacterial spores and bioterrorism agent biomarker from clinical and environmental matrices. Journal of Microbiological Methods. 2002; 48:139-147.
Wikipedia brochure for defining stocahstic process. Sep. 2, 2009.
Williams, et al. Amplification of complex gene libraries by emulsion PCR. Nature Methods. 2006;3(7):545-50.
Willis, et al. Monolithic teflon membrane valves and pumps for harsh chemical and low-temperature use. Lab Chip. 2007; 7:1469-1474.
Woolley, et al. Functional Integration of PCR Amplification and Capillary Electrophoresis in a Microfabricated DNA Analysis Device. Analytical Chemistry. 1996;68(23):4081-4086.
Wright, et al. Behavior and Use of Nonaqueous Media without Supporting Electrolyte in Capillary Electrophoresis and Capillary Electrochromatography. Analytical Chemistry. 1997;69(16):3251-3259.
Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.
Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.
Xue, et al. Multichannel Microchip Electrospray Mass Spectrometry. Analytical Chemistry. 1997;69(3):426-430.
Yacoub-George, et al. Chemiluminescence multichannel immunosensor for biodetection Analytica Chimica Acta. 2002; 457:3-12.
Yang, et al. A MEMS thermopneumatic silicone rubber membrane valve. Sensors and Actuators. 1998;A64(1):101-108.
Yang, et al. An Integrated Stacked Microlaboratory for Biological Agent Detection with DNA and Immunoassays. Biosensors & Bioelectronics. 2002; 17:605-618.
Yu, et al. Preparation of Monolithic Polymers with Controlled Porous Properties for Microfluidic Chip Applications Using Photoinitiated Free Radical Polymerization. Journal of Polymer Science. 2002;40:755-769.
Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.
Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.
Zhang, et al. Microfabricated Devices for Capillary Electrophoresis-Electrospray Mass Spectrometry. Analytical Chemistry. 1999;71(15):3258-3264.
Zhang, et al. PMMA/PDMS valves and pumps for disposable microfluidics. Lap Chip. 2009; 9:3088-3094.
Zhu, et al. High-Sensitivity Capillary Electrophoresis of Double-Stranded DNA Fragments Using Monomeric and Dimeric Fluorescent Intercalating Dyes. Anal Chem. 1994; 1941-1948.

\* cited by examiner

METHODS FOR GENERATING SHORT TANDEM REPEAT (STR) PROFILES

CROSS-REFERENCE

This application is a continuation of U.S. patent application Ser. No. 12/321,594, filed Jan. 21, 2009, which claims the benefit of U.S. Provisional Application No. 61/022,722, filed Jan. 22, 2008 and U.S. Provisional Application No. 61/140,602, filed Dec. 23, 2008, which are hereby incorporated by reference in their entirety.

STATEMENT AS TO FEDERALLY SPONSORED RESEARCH

Aspects of this invention were made with government support under one or more of Project No. W911SR-04-P-0047 awarded by the Department of Defense and Grant No. 5R01HG003583 awarded by the NIH. The government may have certain rights in this invention.

BACKGROUND OF THE INVENTION

Sample preparation is a ubiquitous problem in biological analytical systems. The issue of providing sufficiently purified targets from diverse raw sample types to reliably perform downstream analytical assays is pervasive and covers cell biology, genomics, proteomics, metabolomics, food biology, molecular diagnostics, and many other biological and medical assays. While many advances in sample preparation have been made the chief solution has been to develop reagents that are used manually or in robotic systems that use rectilinear stages or multi-axis arms to manipulate samples.

Microfluidics and nanofluidics allow miniaturized sample volumes to be prepared for analysis. Advantages include the nanoscale consumption of reagents to reduce operating costs and full automation to eliminate operator variances. Microfluidic sample preparation can either interface with existing or future detection methods or be part of a completely integrated system. In the present application, methods and apparatuses are disclosed that integrate full volume sample preparation with volumes over 10 mL with microliter and smaller volumes for sample preparation and analysis.

Starting from the sample, the present invention can be applied to concentrate, and pre-separate components for further processing to detect and classify organisms in matrices comprising aerosol samples, water, liquids, blood, stools, nasal, buccal and other swabs, bodily fluids, environmental samples with analysis by ELISA, PCR or other nucleic acid amplification techniques, single molecule detection, protein arrays, mass spectroscopy, and other analytical methods well known to one skilled in the art.

Microfluidic nucleic acid purification can be performed to prepare the sample for nucleic acid assays. For DNA analysis, PCR amplification is one current method. Microarray DNA, RNA and protein analysis also requires extensive sample preparation before the sample can be applied to the microarray for reaction and readout.

Samples can be obtained by a wide variety of substrates and matrices. The matrix may contain complex mixtures including inhibitory compounds such as hemes, indigo, humic acids, divalent cations, and proteins etc that interfere with DNA-based amplification. Aerosols can contain large amounts of molds, metals, and soils humic and other acids that all interfere with PCR amplification—the gold standard. Early work showed that as few as three seeded organisms could be detected from diluted samples of soil extracts followed by PCR amplification of two 16S ribosomal gene fragments. Low-melting-temperature agarose has been used to extract DNA from soil samples for 16S and 18S rDNA PCR amplification using universal primers. Spun separation gels in column format can be used, such as Sephadex columns. Multistep purifications such as organic extractions combined with Sephadex columns were developed. Bead beating was found to be an effective way to prepare samples for high numbers of organisms and grinding in liquid nitrogen to detect low numbers of organisms. While these methods are effective they were best suited for research laboratory environments.

Solid phase extractions to columns, beads, and surfaces can be used to purify DNA before DNA analysis. Proteinase K followed by a Qiagen QIA Amp silica-gel membrane columns and IsoCode Stix, an impregnated membrane-based technology, followed by heating, washing and a brief centrifugation were compared for *B. anthracis* Sterne vegetative cells in buffer, serum, and whole blood and spores in buffer and found to work well.

A variety of separations can be performed using the devices and methods of the invention. For example, the devices and methods of the invention can be used to perform chromatography, phase-based or magnetic-based separation, electrophoresis, distillation, extraction, and filtration. For example, a microfluidic channel or a capillary can be used for chromatography or electrophoresis. As well, beads, such as magnetic beads can be used for phase-based separations and magnetic-based separations. The beads, or any other surfaces described herein, can be functionalized with binding moieties that exhibit specific or non-specific binding to a target. The binding can be based on electrostatics, van der Walls interactions, hydrophobicity, hydrophilicity, hydrogen bonding, ionic interactions, as well as partially covalent interactions like those exhibited between gold and sulfur. In preferred embodiments, the devices and methods of the invention utilize immunomagnetic separations.

Immunomagnetic separation (IMS) is a powerful technology that allows targets to be captured and concentrated in a single step using a mechanistically simplified format that employs paramagnetic beads and a magnetic field (see Grodzinski P, Liu R, Yang J, Ward M D. Microfluidic system integration in sample preparation microchip-sets—a summary. Conf Proc IEEE Eng Med Biol Soc. 2004; 4:2615-8, Peoples M C, Karnes H T. Microfluidic immunoaffinity separations for bioanalysis. J Chromatogr B Analyt Technol Biomed Life Sci. 2007 Aug. 30, and Stevens K A, Jaykus L A. Bacterial separation and concentration from complex sample matrices: a review. Crit Rev Microbiol. 2004; 30(1):7-24). IMS can be used to capture, concentrate, and then purify specific target antigens, proteins, toxins, nucleic acids, cells, and spores. While IMS as originally used referred to using an antibody, we generalize its usage to include other specific affinity interactions including lectins, DNA-DNA, DNA-RNA, biotin-streptavidin, and other affinity interactions that are coupled to a solid phase. IMS works by binding a specific affinity reagent, typically an antibody or DNA, to paramagnetic beads which are only magnetic in the presence of an external magnetic field. The beads can be added to complex samples such as aerosols, liquids, bodily fluids, or food. After binding of the target to the affinity reagent (which itself is bound to the paramagnetic bead) the bead is captured by application of a magnetic field. Unbound or loosely bound material is removed by washing with compatible buffers, which purifies the target from other, unwanted materials in the original sample. Because beads are small (nm to um) and bind high levels of target, when the beads are concentrated by magnetic force they typically form bead beds of just nL-uL volumes, thus concentrating the target at the same time it is purified. The purified and concentrated targets can be conveniently transported, denatured, lysed or analyzed while on-bead, or eluted off bead for further sample preparation, or analysis.

Immunomagnetic separations are widely used for many applications including the detection of microorganisms in food, bodily fluids, and other matrices. Paramagnetic beads can be mixed and manipulated easily, and are adaptable to microscale and microfluidic applications. This technology provides an excellent solution to the macroscale-to-microscale interface: beads are an almost ideal vehicle to purify samples at the macroscale and then concentrate to the nanoscale (100's of nL) for introduction into microfluidic or nanofluidic platforms. Immunomagnetic separations are commonly used as an upstream purification step before real-time PCR, electrochemiluminescence, and magnetic force discrimination.

The ability to move fluids on microchips is a quite important. This invention describes technologies in sample capture and purification, micro-separations, micro-valves, -pumps, and -routers, nanofluidic control, and nano-scale biochemistry. A key component of the technology is Micro-robotic On-chip Valves (MOVe) technology (an example of which is shown in FIG. 1) and its application to miniaturize and automate complex workflows. Collectively the MOVe valves, pumps, and routers and the instrumentation to operate them can be referred to as a microchip fluid processing platform.

The heart of the microchip fluid processing platform technology are MOVe pumps, valves, and routers that transport, process, and enable analysis of samples. These novel externally actuated, pneumatically-driven, on-chip valves, pumps, and routers, originally developed in the Mathies laboratory at the University of California at Berkeley (U. C. Berkeley) (Grover, W. H. A. M. Skelley, C. N. Liu, E. T. Lagally, and R. M. Mathies. 2003. *Sensors and Actuators* B89:315-323; Richard A. Mathies et al., United States Patent Application, 20040209354 A1 Oct. 21, 2004; all of which are herein incorporated by reference in their entirety) can control fluidic flow at manipulate volumes from 20 nL to 10 µL.

The MOVe valves and pumps (FIG. 1) can combine two glass microfluidic layers with a polydimethyl siloxane (PDMS) deformable membrane layer that opens and closes the valve, and a pneumatic layer to deform the membrane and actuate the valve. The microfluidic channel etched in the top glass fluidic wafer is discontinuous and leads to vias through the "via wafer" and microfluidic channels to a valve seat which is normally closed (FIG. 1A). When a vacuum is applied to the pneumatic displacement chamber by conventional-scale vacuum and pressure sources, the normally closed PDMS membrane lifts from the valve seat to open the valve (FIG. 1B). The bottom panel of FIG. 1 shows a top view of the valve a similar scale as the other panels.

Three microvalves can be used to make a micropump on a microchip to move fluids from the Input area to the Output area on Microchip A. The fluids are moved by three or more valves. The valves can be created actuation of a deformable structure. In some implementations a valve seat is created and in other embodiments no valve seat may be needed. FIG. 2 shows MOVe devices from top to bottom: valve, router, mixer, bead capture. Self-priming MOVe pumps (FIG. 2, top) are made by coordinating the operation of three valves and can create flow in either direction. Routers are made from three or more MOVe valves (FIG. 2, top middle panel). Mixing has been a holy grail for microfluidics: MOVe mixers (FIG. 2, bottom middle panel) rapidly mix samples and reagents. MOVe devices work exquisitely with magnetic beads to pump or trap sets of beads (FIG. 2, bottom panel).

The normally closed MOVe valves, pumps, and routers are durable, easily fabricated at low cost, can operate in dense arrays, and have low dead volumes. Arrays of MOVe valves, pumps, and routers are readily fabricated on microchips. Significantly, all the MOVe valves, pumps, and routers on a microchip are created at the same time in a simple manufacturing process using a single sheet of PDMS membrane—it costs the same to make 5 MOVe micropumps on a microchip as to create 500. This innovative technology offers for the first time the ability to create complex micro- and nanofluidic circuits on microchips.

Patents and applications which discuss the use and design of microchips include U.S. Pat. No. 7,312,611, issued on Dec. 25, 2007; U.S. Pat. No. 6,190,616, issued on Feb. 20, 2001; U.S. Pat. No. 6,423,536, issued on Jul. 23, 2002; U.S. Ser. No. 10/633,171 Mar. 22, 2005; U.S. Pat. No. 6,870,185, issued on Mar. 22, 2005 US Application No. US 2001-0007641, filed on Jan. 25, 2001; US Application US20020110900, filed on Apr. 18, 2002; US patent application 20070248958, filed Sep. 15, 2005; US patent application US 20040209354, filed on Dec. 29, 2003; US patent application US2006/0073484, filed on Dec. 29, 2003; US20050287572, filed on May 25, 2005; US patent application US20070237686, filed on Mar. 21, 2007; US 20050224352 filed on Nov. 24, 2004; US 20070248958, filed on, Sep. 15, 2005; US 20080014576, filed on Feb. 2, 2007; and, US application US20070175756, filed on Jul. 26, 2006; all of which are herein incorporated by reference in their entirety.

SUMMARY OF THE INVENTION

In one aspect this invention provides a device comprising: a microfluidic microchip comprising at least one port aperture fluidically connected to at least one microfluidic channel in the microfluidic microchip, wherein the channel comprises at least one valve that controls movement of a fluid through the channel; and a cartridge mated to the microchip and comprising a chamber, wherein said chamber comprises two chamber apertures that are each aligned with a port aperture of said microfluidic microchip. In one embodiment said cartridge is adapted to receive at least one sample or one reagent. In another embodiment said cartridge is fluidically connected to another cartridge that is mated to another microchip. In another embodiment said cartridge comprises at least two chambers. In another embodiment at least one of said at least two chambers is adjacent to a movable magnet. In another embodiment at least one of said at least two chambers is temperature controlled. In another embodiment at least one of said at least two chambers comprises a filter. In another embodiment said at least one chamber comprises a fluidic volume greater than or equal to 5 µL. In another embodiment said at least one chamber comprises a fluidic volume greater than or equal to 10 µL. In another embodiment the fluidic volume of said cartridge is a 100× of the fluidic volume of said microfluidic microchip. In another embodiment one of said at least one chambers further comprises a filter. In another embodiment said device further comprises a magnet for applying a magnetic field to the cartridge or the microfluidic microchip. In another embodiment the valve is pneumatically actuated. In another embodiment said cartridge is adapted to be connected to at least one pressure source for the delivery of said at least one reagent or said at least one sample. In another embodiment said pressure source provides a positive or negative pressure to the cartridge. In another embodiment said at least one pressure source is controlled by a pneumatic solenoid. In another embodiment said at least one pressure source is a pneumatic manifold. In another embodiment the microfluidic microchip comprises a fluidic layer, an elastomeric layer, and a pneumatic layer. In another embodiment said cartridge further comprises at least one input port, wherein said at least one input port is adapted to mate with a delivery device, wherein said delivery device is fluidically connected to the fluidic layer of said microfluidic microchip; and wherein one of said at least one chamber is a closed reaction chamber fluidically connected to the fluidic layer of said microfluidic microchip. In another embodiment said delivery device is thermally coupled to a temperature modulator. In another embodiment said delivery device is a syringe. In another embodiment said cartridge is designed to enrich at least one component from said sample and comprises at least one sample input port, wherein said at least one chamber is a closed reaction chamber comprising beads, and wherein said beads bind to said at least one component. In another embodiment the cartridge further comprises at least one reagent reservoir comprising reagents for amplifying a nucleic acid, wherein the at least one reagent reservoir is fluidically connected to the chamber through the microchip. In another embodiment the cartridge further comprises at least one bead reservoir comprising beads for binding an amplified nucleic acid, wherein the at least one bead reservoir is fluidically connected to the chamber through the microchip. In another embodiment said beads are paramagnetic beads or glass beads. In another embodiment said binding of at least one component to a bead is reversible. In another embodiment said beads are paramagnetic beads, and wherein said device further comprises a movable magnet that can attract said paramagnetic beads to the wall of said closed reaction chamber. In another embodiment said cartridge is designed to enrich at least one component from a sample, wherein said at least one component is DNA, RNA, microRNA, siRNA, protein, lipid, or polysaccharide.

In another aspect this invention provides a method for performing biochemical reactions comprising: (a) providing the device comprising a microfluidic microchip comprising at least one port aperture fluidically connected to at least one microfluidic channel in the microfluidic microchip, wherein the channel comprises at least one valve that controls movement of a fluid through the channel; and a cartridge mated to the microchip and comprising a chamber, wherein said chamber comprises two chamber apertures that are each aligned with a port aperture of said microfluidic microchip, and (b) performing at least one enzymatic reaction within said chamber. In one embodiment said at least one enzymatic reaction comprises ligating, blunting, nick repairing, denaturing, polymerizing, hydrolyzing, phosphorylation or any combination thereof. In another embodiment the method further comprises separating a product of said enzymatic reaction using solid-phase particles.

In another aspect this invention provides a method for enriching at least one component from a sample comprising: (a) mating a delivery device to an input port of a device comprising: a microfluidic microchip comprising at least one port aperture fluidically connected to at least one microfluidic channel in the microfluidic microchip, wherein the channel comprises at least one valve that controls movement of a fluid through the channel; and a cartridge mated to the microchip and comprising a chamber, wherein said chamber comprises two chamber apertures that are each aligned with a port aperture of said microfluidic microchip wherein said cartridge further comprises at least one input port, wherein said at least one input port is adapted to mate with a delivery device, wherein said delivery device is fluidically connected to the fluidic layer of said microfluidic microchip; and wherein one of said at least one chamber is a closed reaction chamber fluidically connected to the fluidic layer of said microfluidic microchip, (b) treating said sample with at least one reagent to increase the availability of said at least one component for enrichment, (c) delivering said at least one component to said at least one reaction chamber of said cartridge, (d) binding said component to one or more particles in said at least one closed reaction chamber, (e) washing said particle bound component to remove waste, and (f) eluting said particle bound component. In one embodiment said delivering comprises pumping said at least one component to said at least one reaction chamber through said at least one valve of the microfluidic microchip. In another embodiment said binding comprises pumping said particles from a reagent port in the cartridge to said at least one reaction chamber through said at least one valve of the microfluidic microchip. In another embodiment said particle is a paramagnetic bead, a nanoparticle, a resin, or a solid-phase particle. In another embodiment said at least one component is DNA, RNA, microRNA, siRNA, protein, lipid, or polysaccharide. In another embodiment step (b) further comprises thermally modulating said delivery device. In another embodiment step (b) further comprises delivering a lysis reagent or a component isolation reagent from a reagent port on said cartridge into said delivery device to increase the availability of said at least one component for enrichment. In another embodiment the beads of step (d) are paramagnetic beads. In another embodiment said washing step (e) comprises attracting said paramagnetic beads with a movable magnet. In another embodiment said microfluidic microchip directs the flow of said waste in a second direction. In another embodiment step (c) comprises using pneumatically actuated valves in the microfluidic microchip or an external pressure source to deliver said at least one component to said at least one closed reaction chamber of said cartridge. In another embodiment the external pressure source provides a positive or negative pressure to the microfluidic microchip. In another embodiment said sample delivery device is a syringe.

In another aspect this invention provides a device comprising: (a) a first fluid manipulation module comprising: (i) a first microfluidic microchip comprising a port aperture fluidically connected to a microfluidic channel in the microfluidic microchip, wherein the channel comprises at least one valve that controls movement of a fluid through the channel; and (ii) a cartridge mated to the microfluidic microchip and comprising at least one sample input port, at least one chamber, an exit port, wherein the sample input port is connected to the port aperture, wherein at least one of said at least one exit ports is aligned with an exit port aperture of said first microfluidic microchip, and wherein said at least one chamber is fluidically connected to the fluidic layer of said first microfluidic microchip; (b) a reaction channel, wherein said reaction channel is not contained within said first microchip; (c) a temperature modulator, wherein said reaction channel is fluidically connected to a port on said cartridge that is fluidically connected to said exit port and at least a portion of said reaction channel is in thermal contact with said temperature modulator; and (d) a magnet for applying a magnetic field to the microfluidic microchip, the cartridge, or the reaction channel. In one embodiment said magnet is adjacent to said reaction channel. In another embodiment the device further comprises a second microfluidic microchip that is fluidically connected to said first microfluidic microchip through said reaction channel. In another embodiment said temperature modulator is a Peltier device. In another embodiment the device further comprises a paramagnetic bead.

In another aspect this invention provides a method comprising: delivering a sample containing a nucleic acid to a device comprising: (a) a first fluid manipulation module comprising: (i) a first microfluidic microchip comprising a port aperture fluidically connected to a microfluidic channel in the microfluidic microchip, wherein the channel comprises at least one valve that controls movement of a fluid through the channel; and (ii) a cartridge mated to the microfluidic microchip and comprising at least one sample input port, at least one chamber, an exit port, wherein the sample input port is connected to the port aperture, wherein at least one of said at least one exit ports is aligned with an exit port aperture of said first microfluidic microchip, and wherein said at least one chamber is fluidically connected to the fluidic layer of said first microfluidic microchip; (b) a reaction channel, wherein said reaction channel is not contained within said first microchip; (c) a temperature modulator, wherein said reaction channel is fluidically connected to a port on said cartridge that is fluidically connected to said exit port and at least a portion of said reaction channel is in thermal contact with said temperature modulator; and (d) a magnet for applying a magnetic field to the microfluidic microchip, the cartridge, or the reaction channel; transporting the nucleic acid and an effective amount of reagents through the portion of the reaction channel in thermal contact with the temperature modulator one or more times; and amplifying the nucleic acid; and analyzing the amplified nucleic acid. In one embodiment the method further comprises using the temperature modulator to perform thermocycling. In another embodiment said reagents are reagents for polymerase chain reaction or cycle sequencing.

In another aspect this invention provides a device comprising: (a) a first microfluidic microchip comprising a fluidics layer, an actuation layer, and a pneumatic layer, wherein the fluidics layer comprises one or more microfluidic channels, wherein at least one of said one or more microfluidic channels comprises an exit aperture, (b) a flexible connector fluidically connected to the exit aperture at a first end of the flexible connector; (c) a capillary fluidically connected to said flexible connector; and (d) a first electrode and a second electrode, wherein the first electrode and second electrode are configured to produce an electric field along a path of the capillary. In one embodiment the flexible connector is surgical, poly(tetrafluoroethylene) or silicon tubing. In another embodiment the flexible connector is elastic tubing. In another embodiment the flexible connector has an outer diameter of about 1.5 to 3 mm and an inner diameter of about 0.25 to 0.5 mm. In another embodiment the flexible connector is also fluidically connected to a second microfluidic microchip or the first microfluidic microchip at a second end of the flexible connector. In another embodiment the flexible connector is fluidically connected to the exit aperture by a cannula, an upfit tubing, a microtubing fitting, or an upchurch tubing adapter. In another embodiment the capillary has an outer diameter of about 150-500 microns and an inner diameter of about 10-100 microns. In another embodiment the capillary is polyamide or poly(tetrafluoroethylene) coated. In another embodiment the capillary comprises a separation gel. In another embodiment the capillary is about 10 to 100 cm long. In another embodiment the first electrode is a forked electrode. In another embodiment said forked electrode comprises one or more conductive channels or one or more metallic conductors. In another embodiment the first electrode and the second electrode produce an electric field that is about 25 to 500 V/cm.

In another aspect this invention provides a method comprising: providing the composition to a microfluidic microchip, wherein the microfluidic microchip comprises a fluidics layer, a elastomeric layer, and a pneumatic layer; delivering the composition to a flexible connector that is fluidically connected to the microfluidic microchip; providing a electric field to move the composition into a capillary; and performing capillary electrophoresis on the composition to separate a component based on size or charge. In one embodiment the electric field is about 25 to 500 V/cm. In another embodiment said composition in said tube is adjacent to a first and second bolus of gas, wherein said first bolus of gas is upstream of said composition and said second bolus of gas is downstream of said composition in said tube. In another embodiment said first and second boluses of gas isolates said composition from other compositions. In another embodiment the composition comprises at least one component that is a nucleic acid, protein, fatty acids, or polysaccharides. In another embodiment the nucleic acid is microRNA, DNA, RNA, or siRNA.

In another aspect this invention provides a device comprising: (a) a separation channel fluidically connected to a loading channel; (b) a forked electrode comprising at least two electrodes that are electrically connected to the loading channel and the separation channel through the loading channel, wherein the fluidic connection between the separation channel and the loading channel is located between the electrical connections of the two electrodes to the loading channel; and (c) a pneumatically actuated valve fluidically connected to the loading channel. In one embodiment the device further comprises a cannular electrode in electrical contact with said forked electrode, wherein the inner diameter of said cannular electrode is at least about 0.2 mm. In another embodiment said cannular electrode is configured to reduce injection of gas into said separation channel. In another embodiment the separation channel is a capillary, and wherein the capillary is fluidically connected to the pneumatically actuated valve using a flexible connection. In another embodiment the separation channel is a microchannel. In another embodiment the separation channel and pneumatically actuated valve are integrated on a microfluidic microchip. In another embodiment the loading channel comprises a loading channel solution and the separation channel comprises a separation channel solution, and wherein the sample solution has a lower electrical conductivity than the separation channel solution. In another embodiment the at least two electrodes comprise at least two microchannels that are on one end fluidically connected to the loading channel on either side of the fluidic connection between the separation channel and the loading channel and on the other end fluidically connected to a base channel. In another embodiment each of the at least two electrodes is a metallic conductors that is electrically connected to a voltage source and the loading channel.

In another aspect this invention provides a device comprising: a first, a second, and a third microfluidic channel that are joined to form a three-way junction; wherein the first microfluidic channel is electrically connected to a first electrode of a forked electrode, wherein the second microfluidic channel is electrically connected to a second electrode of the forked electrode, and wherein the first, the second, and the third microfluidic channel are each fluidically connected to a pneumatically actuated valve.

In another aspect this invention provides a method for performing capillary electrophoresis comprising: providing a device comprising: (1) a separation channel fluidically connected to a loading channel; (2) a forked electrode comprising at least two electrodes that are electrically connected to the loading channel and the separation channel through the loading channel, wherein the fluidic connection between the separation channel and the loading channel is located between the electrical connections of the two electrodes to the loading channel; and (3) a pneumatically actuated valve fluidically connected to the loading channel; providing a separation channel solution to the separation channel; delivering a composition to the loading channel, wherein the pneumatically actuated valve is used to control the delivery of the composition to the loading channel; and applying an electric field along the separation channel using the forked electrode; performing capillary electrophoresis on the composition to separate the component based on size or charge. In another embodiment the composition has a lower electrical conductivity than the separation channel solution. In another embodiment the composition is concentrated by said applying the electric field.

In another aspect this invention provides a microfluidic device comprising: (a) a microfluidic microchip comprising: (1) a first channel comprising a first valve; (2) a second channel that intersects the first channel on one side of the first valve; (3) a third channel that intersects the first channel on the other side of the first valve; wherein at least one of the second or third channel intersect the first channel at a T-valve or at least one of the second or third channel comprise a second valve, and wherein the second and third channel each connect to a port; and (b) a fluid loop that is removably attached to the ports such that fluid can flow from the first channel to the fluid loop.

In another aspect this invention provides a microfluidic device comprising: (a) a microchip comprising one or more pneumatically actuated valves; and (b) a sample loop, wherein the sample loop is fluidically connected to the one or more pneumatically actuated valves through ports in the microfluidic microchip, and wherein the sample loop has a fixed volume and the sample loop is removable. In one embodiment said pneumatically actuated valves are actuated by one or more pneumatic channels in the microfluidic device. In another embodiment the sample loop comprises a capillary tube. In another embodiment the sample loop is fluidically connected to a pass-through microfluidic channel at a first junction and a second junction, and wherein a pass-through microfluidic pneumatically actuated valve is positioned in the pass-through microfluidic channel between the first and second junctions. In another embodiment at least one junction comprises a T-valve, wherein closure of the T-valve does not prevent passage of fluid through the pass-through microfluidic channel. In another embodiment the sample loop is connected to the pass-through microfluidic channel through first and second channels, and wherein at least one of the first and the second channel comprise a sample loop valve.

In another aspect this invention provides a method for delivering a fixed volume of fluid to a microfluidic device comprising: configuring a device with a sample loop comprising a desired volume, wherein the sample loop is removable; using one or more pneumatically actuated valves on a microfluidic device to fill the sample loop with the fixed volume of the fluid; and delivering the fluid to the microfluidic device. In one embodiment the sample loop and a pass-through microfluidic channel are fluidically connected at a first junction and a second junction, and wherein at least one junction comprises a T-valve. In another embodiment the pass-through microfluidic channel comprises a pass-through microfluidic valve positioned between the first junction and the second junction.

In one aspect, this invention provides a device comprising: (a) a cartridge; (b) a microfluidic microchip having one or more microfluidic diaphragm valves, fluidically interfaced with the cartridge; and (c) a pneumatic manifold interfaced with the microfluidic microchip on a surface of the microfluidic microchip, wherein the pneumatic manifold covers all or only a portion of the surface of the microfluidic microchip. In one embodiment the device further comprises a magnet configured to generate a magnetic field in a chamber of the microfluidic microchip. In one embodiment wherein the pneumatic manifold has an annular space for the magnetic component. In another embodiment the microfluidic microchip comprises a fluidics layer comprising fluidics channels, a pneumatics layer comprising pneumatics channels, and an activation layer sandwiched there between, wherein the cartridge comprises a chamber with an opening, wherein the opening mates with an opening in the fluidics layer that connects to a fluidics channel, and the pneumatic manifold comprises an opening that mates with an opening in the pneumatics layer of the microfluidic microchip that connects with a pneumatic channel.

In another aspect this invention provides a device comprising: (a) a cartridge; (b) a microfluidic microchip having one or more microfluidic diaphragm valves and interfaced with the cartridge; (c) a pneumatic manifold interfaced with the microfluidic microchip on a surface of the microfluidic microchip; and (d) a temperature controlling block in thermal contact with the cartridge. In one embodiment the microfluidic microchip comprises a fluidics layer comprising fluidics channels, a pneumatics layer comprising pneumatics channels, and an activation layer sandwiched there between, wherein the cartridge comprises a chamber with an opening, wherein the opening mates with an opening in the fluidics layer that connects to a fluidics channel, and the pneumatic manifold comprises an opening that mates with an opening in the pneumatics layer of the microfluidic microchip that connects with a pneumatic channel.

In another aspect this invention provides a device comprising a microfluidic microchip having one or more microfluidic diaphragm valves and interfaced with a cartridge; wherein the microfluidic microchip has a bead rail and a reagent rail.

In another aspect this invention provides a method for amplifying mRNA and purifying amplified RNA comprising: (a) providing device comprising: (i) a cartridge; (ii) a microfluidic microchip having one or more microfluidic diaphragm valves, fluidically interfaced with the cartridge; (iii) a pneumatic manifold interfaced with the microfluidic microchip on a surface of the microfluidic microchip, wherein the pneumatic manifold covers all or only a portion of the surface of the microfluidic microchip and (iv) a magnet configured to generate a magnetic field in a chamber of the microfluidic microchip, wherein the pneumatic manifold has an annular space for the magnetic component; (b) supplying a sample containing mRNA and reagents to the cartridge; (c) mixing the sample and reagents in a well of the microfluidic microchip; (d) amplifying the mRNA to form amplified RNA; (e) capturing the amplified RNA using magnetic beads; and (f) positioning the magnet in the annular space to capture magnetic beads in a reservoir of the microfluidic microchip.

In another aspect this invention provides a method for amplifying mRNA comprising: (a) providing a device comprising: (i) a cartridge; (ii) a microfluidic microchip having one or more microfluidic diaphragm valves and interfaced with the cartridge; (iii) a pneumatic manifold interfaced with the microfluidic microchip on a surface of the microfluidic microchip; and (iv) a temperature controlling block in thermal contact with the cartridge; (b) supplying a sample containing mRNA and reagents to the cartridge; (c) mixing the sample and reagents in a well of the microfluidic microchip to form a mixture; (d) heating the mixture using the temperature controlling block; and (e) amplifying the mRNA.

In another aspect this invention provides a method for amplifying mRNA and purifying amplified RNA comprising: (a) providing a device comprising a microfluidic microchip having one or more microfluidic diaphragm valves and interfaced with a cartridge; wherein the microfluidic microchip has a bead rail and a reagent rail; (b) supplying reagents to one or more reagent rail wells; (c) supplying magnetic bead slurry to a bead rail well; (d) supplying a sample containing mRNA to a sample well; (e) pumping the sample and the reagents to an output well of the microfluidic microchip to form a mixture; (f) amplifying the mRNA to form amplified RNA; (g) pumping the magnetic bead slurry to a purification well; (h) contacting the magnetic bead slurry with amplified RNA by pumping the amplified RNA to the purification well; and (i) purifying the amplified RNA.

In another aspect this invention provides a method for pumping a fluid in a microfluidic device comprising: (a) providing a microfluidic device comprising a pumping valve, a source well, and a mixing well, wherein the pumping valve, the source well, and the mixing well are fluidically connected by a channel; (b) pumping the fluid in a first direction through the channel from the source well to the pumping valve; and (c) pumping the fluid in a second direction through the channel from the pumping valve to the mixing well, wherein the second direction is opposite of the first direction.

Sample preparation is a challenging area of the bioanalytical process. In one aspect, a method is disclosed for the preparation of samples from many different sample types. In another aspect, an apparatus is disclosed that can prepare samples from many different sample types. In one embodiment, the apparatus operates a cartridge with microscale valves that direct fluid flow in a microchip component that can be fabricated separately or as an integral part of the cartridge. In another embodiment, the apparatus can move samples into the cartridge using pressure-driven flow or vacuum modulated by the microvalves on the cartridge. In another embodiment, the apparatus can manipulate paramagnetic beads for magnetic separation of components of the sample to purify desired analytes with fluid flow directed by the microvalves.

In one embodiment, the apparatus is a universal sample preparation system that can process biological or chemical samples. Samples can be loaded in liquid, swabs, swipes, solids, gases, or other matrices into the cartridge. The apparatus is controlled by electronics which may include a computer to select the proper reagents and direct the fluids using the microscale valves to open and close circuitry that is formed by the cartridge and by the microchip component. The sample can be processed to extract nucleic acids, including DNA, RNA, microRNAs, proteins, lipids, polysaccharides, cell walls, small molecules, and all other biological components of a sample. Similarly the sample can also be processed to extract or purify chemical components. For example, DNA can be processed onto microbeads.

In one embodiment, a sample can be moved into a reaction chamber in a cartridge comprising one or more chambers, channels, tubing, or capillaries that may be permanently attached to the cartridge or may be reversibly joined to the cartridge. Samples may be reproducibly positioned in the channels, tubing or capillaries using vacuum or pressure modulated or created by micropumps that may be located on the cartridge, on the apparatus, on an external device, or other configurations.

In one embodiment, for DNA, the processed sample can be amplified by PCR, rolling circle, branched DNA, EXPAR, LAMP, and other DNA amplification methods well known to one skilled in the art or analyzed by mass spectroscopy or single molecule detection methods. RNA may be processed by Reverse Transcriptase real time-PCR, or samples prepared for DNA microarrays, or other analytical methods. Real time or end point analyzes can be performed with the apparatus.

For proteins, assays may be performed in the cartridge including enzymatic assays, sandwich immunoassays, antibody precipitation, protein digestion, protein and peptide labeling, and other commonly used protein analysis methods. Similarly, other cellular components or chemicals can be extracted or purified using standard methods in the apparatus. Molecular biology methods are readily adapted to the apparatus. Samples can be completely analyzed on the apparatus in a single cartridge, moved to a separate cartridge, or analyzed or further processed in a separate instrument comprising a capillary electrophoresis system or microchip capillary electrophoresis; multidimensional gel and capillary electrophoresis; mass spectroscopy, multidimensional mass spectroscopy with HPLC, ICP, Raman spectroscopy, particle, nanoparticles, and bead based detection, imaging, comprising fluorescence, IR, optical, or any other analytical systems well know to one in the art.

In one embodiment, the integration of a complete sample-to-answer instrument incorporating the cartridge to prepare DNA samples from many inputs and sample types and a microchip-based capillary electrophoresis device for separation of DNA fragments is used for analysis, such as DNA sequencing, fragment sizing, and forensics.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

This invention includes devices that incorporate valves, such as microvalves (including but not limited to pneumatically actuated valves and microscale on-chip valves), into their design in order to control the movement of fluid. These devices can be used for the enrichment of a component, for sample preparation, and/or for analysis of one or more components in or from a sample.

Figure 40:
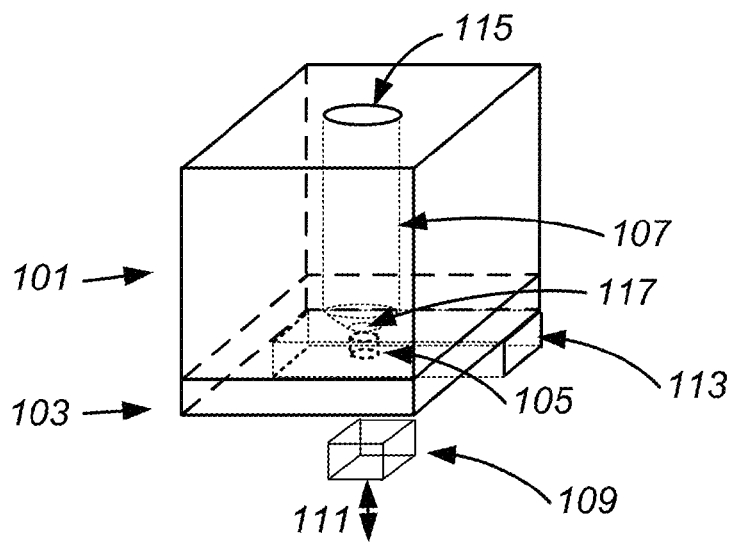
FIG. 40 depicts a device with a cartridge, microfluidic microchip, and a magnet.

The invention also provides devices for fluid and analyte processing and methods of use thereof. The devices of the invention can be used to perform a variety of actions on the fluid and analyte. These actions can include moving, mixing, separating, heating, cooling, and analyzing. The devices can include multiple components, such as a cartridge, a microfluidic microchip, and a pneumatic manifold. FIG. 40 shows an exemplary device having a cartridge (101), microfluidic microchip (103), and pneumatic manifold (113).

I. Sample Preparation Device

Figure 16:
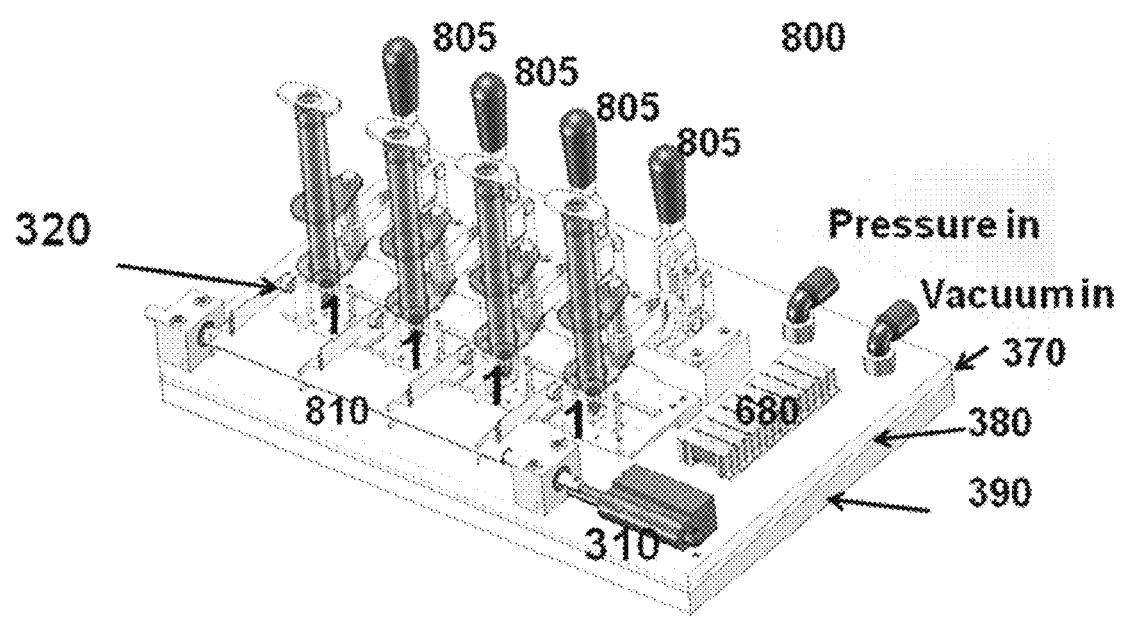
FIG. 16 shows a four cartridge assembly.
Figure 21:
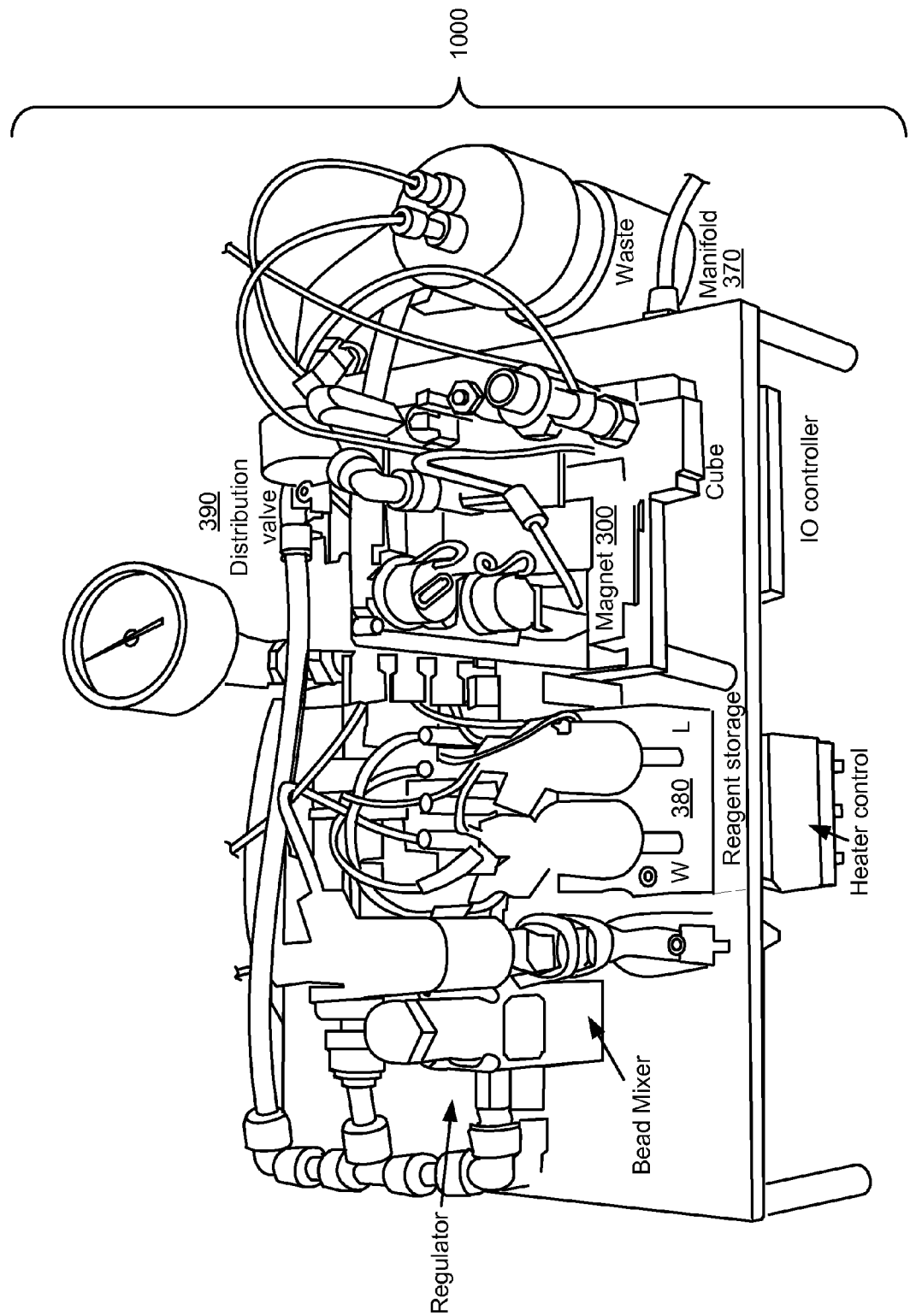
FIG. 21 shows a cartridge mounted on a computer controlled apparatus.
Figure 22:
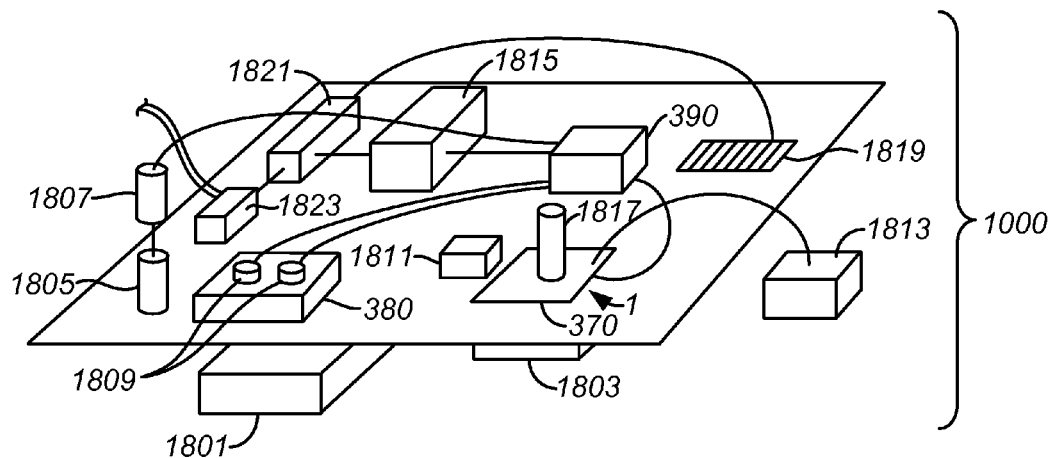
FIG. 22 shows a cartridge mounted on a computer controlled apparatus.
Figure 68:
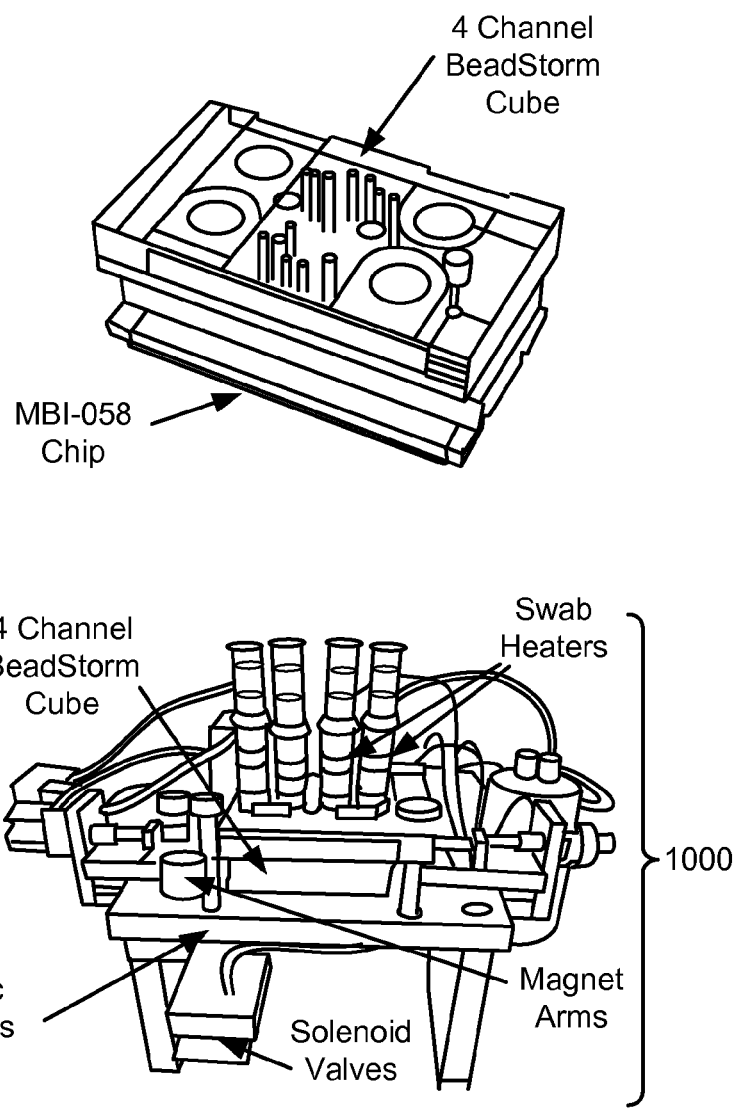
FIG. 68 shows a four-channel sample preparation device on the left and a four-channel sample preparation device mounted on a monolithic pneumatic manifold on the right.

In one aspect a sample preparation device as shown in device 800 in FIG. 16, device 1000 in FIG. 21 and FIG. 22, and device 1000 in FIG. 68 comprises a cartridge integrated with a microfluidic microchip that controls movement of the fluid in the cartridge through microvalves and the components to operate the cartridge. The cartridge and/or the compartments therein can be of sufficient size to process one or more milliliter of an input sample in an automated device. The cartridge can process a sample to output a component that can be moved using pressure-driven flow or vacuum modulated by microvalves. The cartridge can provide an interface with a delivery device comprising macroscale samples, such as blood, aerosol liquids, swabs, bodily fluids, swipes, and other liquid, solid, and gas samples. The cartridge can process macroscale sample volumes using microscale sample preparation and analysis. The cartridge can allow for processing of macroscale or large volume samples using microfluidic devices and components have reduced void volumes that allow for reduced loss of materials.

A. Cartridges

A cartridge, also referred to as a fluidic manifold herein, can be used for a number of purposes. In general, a cartridge can have ports that are sized to interface with large scale devices as well as microfluidic devices. Cartridges or fluidic manifolds have been described in U.S. Patent Application No. 61/022,722, which is hereby incorporated by reference in its entirety. The cartridge can be used to receive materials, such as samples, reagents, or solid particles, from a source and deliver them to the microfluidic microchip. The materials can be transferred between the cartridge and the microfluidic microchip through mated openings of the cartridge and the microfluidic microchip. For example, a pipette can be used to transfer materials to the cartridge, which in turn, can then deliver the materials to the microfluidic device. In another embodiment, tubing can transfer the materials to the cartridge. In another embodiment, a syringe can transfer material to the cartridge. In addition, a cartridge can have reservoirs with volumes capable of holding nanoliters, microliters, milliliters, or liters of fluid. The reservoirs can be used as holding chambers, reaction chambers (e.g., that comprise reagents for carrying out a reaction), chambers for providing heating or cooling (e.g., that contain thermal control elements or that are thermally connected to thermal control devices), or separation chambers (e.g. paramagnetic bead separations, affinity capture matrices, and chromatography). Any type of chamber can be used in the devices described herein, e.g. those described in U.S. Patent Publication Number 2007/0248958, which is hereby incorporated by reference. A reservoir can be used to provide heating or cooling by having inlets and outlets for the movement of temperature controlled fluids in and out of the cartridge, which then can provide temperature control to the microfluidic microchip. Alternatively, a reservoir can house Peltier elements, or any other heating or cooling elements known to those skilled in the art, that provide a heat sink or heat source. A cartridge reservoir or chamber can have a volume of at least about 0.1, 0.5, 1, 5, 10, 50, 100, 150, 200, 250, 300, 400, 500, 750, 1000, 2000, 3000, 4000, 5000 or more μL. The relative volume of a chamber or reservoir can be about 1, 2, 5, 10, 20, 50, 100, 200, 500, 1000, 2000, 5000, 10000 or more greater than a channel or valve within the microfluidic microchip. The size of the chambers and reservoirs of the cartridge, which can be mated to the microfluidic microchip, can be chosen such that a large volume of sample, such as a sample greater than about 1, 5, 10, 50, 100, 500, 1000, 5000, 10000, 50000 or more μL, can be processed, wherein the flow of fluids for processing the sample is controlled by valves in the microfluidic microchip. This can allow for a reduced amount of sample and reagent loss due to the reduced void volumes in the microfluidic microchip compared to other flow control devices, such as pipettes and large scale valves. The void volume within a microfluidic microchip can be less than 1000, 500, 100, 50, 10, 5, 1, 0.5, 0.1, or 0.05 μL. This can allow for the amount of sample or reagent loss during processing of a sample to be less than 20, 15, 10, 7, 5, 3, 2, 1, 0.5, 0.05 percent.

For example, FIG. 40 shows cartridge (101) with a reservoir with a port (115) opening to a side of the cartridge that can be used to receive materials from a pipette or any other large scale device. The port can also be adapted with fitting to receive tubing or a capillary to connect the cartridge to upstream fluidics. The reservoir can taper down to form a cartridge reservoir opening (117) that interfaces, aligns, or mates with an opening 105 in the fluidics layer of the microfluidic microchip.

A cartridge can be constructed of any material known to those skilled in the art. For example, the cartridge can be constructed of a plastic, glass, or metal. A plastic material may include any plastic known to those skilled in the art, such as polypropylene, polystyrene, polyethylene, polyethylene terephthalate, polyester, polyamide, poly(vinylchloride), polycarbonate, polyurethane, polyvinyldiene chloride, cyclic olefin copolymer, or any combination thereof. The cartridge can be formed using any technique known to those skilled in the art, such as soft-lithography, hard-lithography, milling, embossing, ablating, drilling, etching, injection molding, or any combination thereof.

Figure 3:
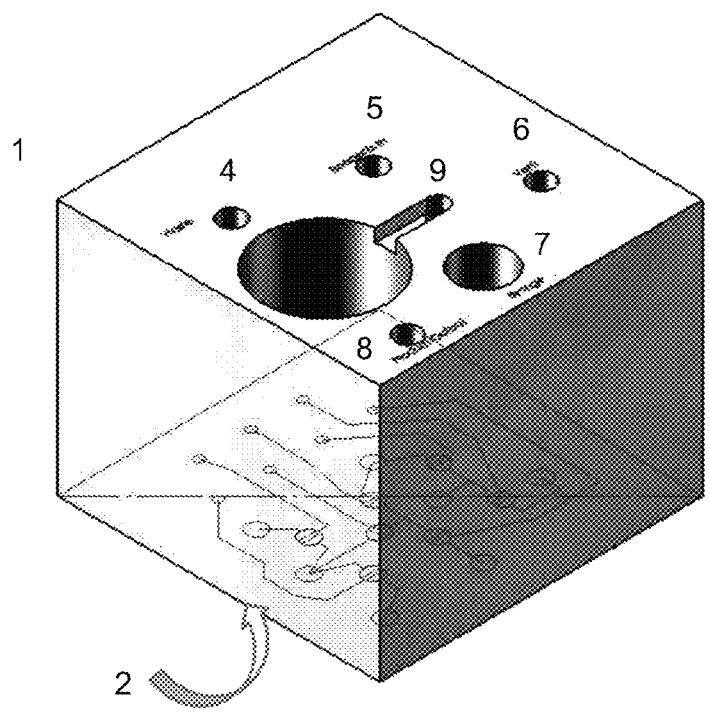
FIG. 3 shows a fluidic cartridge with MOVe microvalves.
Figure 4:
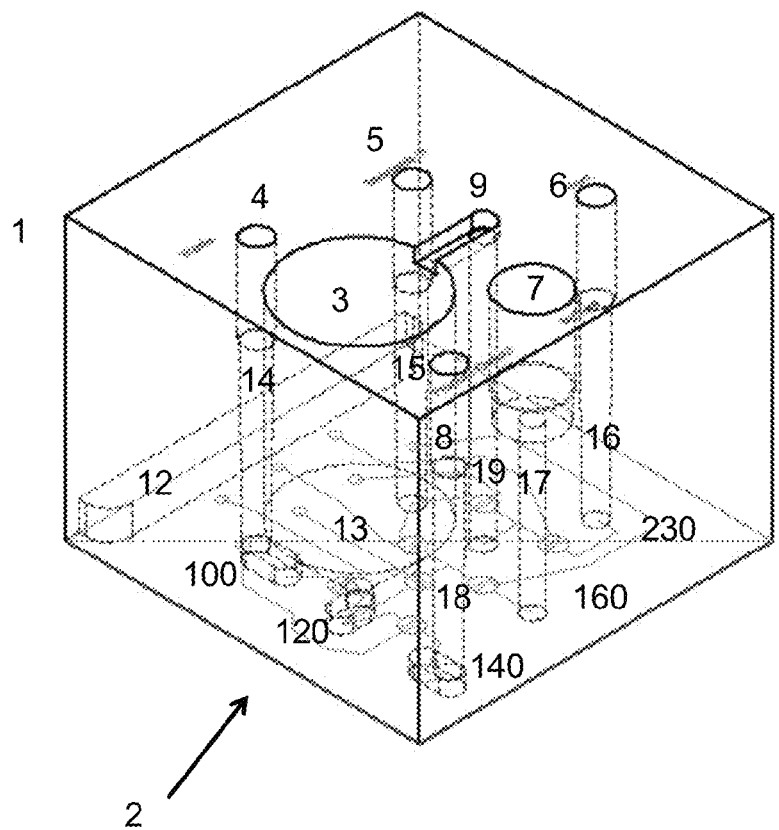
FIG. 4 shows a fluidic cartridge with ports to a microfluidic microchip with microvalves.
Figure 59:
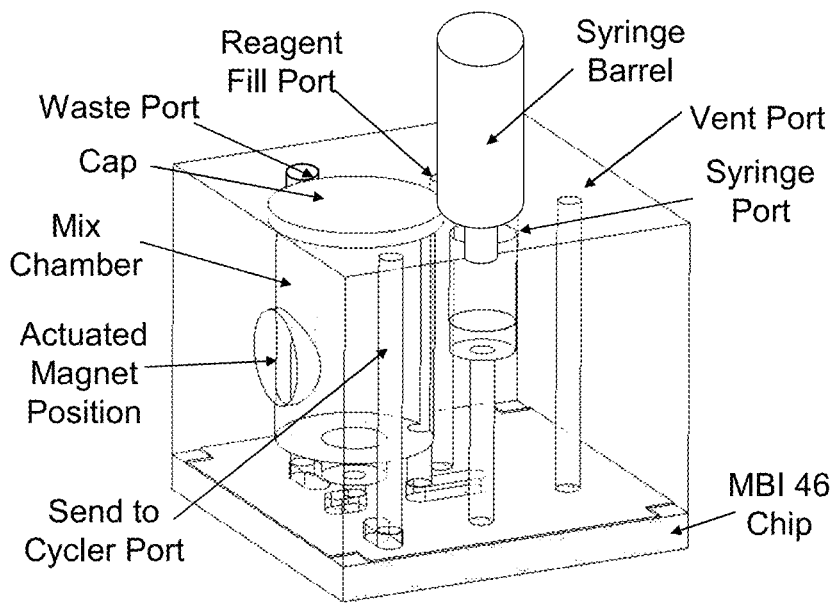
FIG. 59 shows a microfluidic microchip with MOVe valves that controls flows in a cartridge.

As exemplified in FIG. 3 and FIG. 4, a cartridge (1) can comprise a rectilinear, configuration with flat sides. In another embodiment, a cartridge comprises a surface that is curved, rounded, indented or comprises a protrusion. In one embodiment a cartridge has at least one substantially flat surface which is adjacent to a microfluidic microchip. The cartridge is adapted to be fluidically connected with ports in the microchip. For example, openings in the surface of the cartridge can be aligned with ports in the microchip. When the cartridge and microchip are mated to one another, the openings align to create the fluidic connections allowing liquids to pass from the cartridge into the ports of the microchip, which are connected to channels typically having valves that form fluidic circuits. Another embodiment of a cartridge is shown in FIG. 59. FIG. 59 shows a cartridge with multiple ports that mate with a microchip and external components, such as syringes. The compartment in the cartridge can be shaped to allow insertion of the syringe and its protrusion. The cartridge can also include a vent port to vent gases in chambers of the cartridge or chambers of the microchip. As well, FIG. 59 shows the position where an actuated magnet can be used to apply a magnetic field to a mix chamber. Additionally, FIG. 59 shows a cap that can be used to close the mix chamber.

In one embodiment a cartridge contains one or more features, including but not limited to a chamber, a port, a channel or a magnet. In one embodiment, microvalves, such as pneumatically actuated valves are combined with the microfluidic cartridge. In some embodiments the microvalves are active mechanical microvalves (such as magnetic, electrical, or piezoelectric thermal microvalves), non-mechanical microvalves (such as bistable electromechanical phase change or rheological microvalves), external microvalves (such as modular or pneumatic), passive mechanical (such as check microvalves or passive non-mechanical (such as capillary microvalves) (Oh et al., A review of microvalves, J. Micromech Microeng. 16 (2006) R13-R39, herein incorporated by reference in its entirety)).

In another embodiment, pneumatically actuated valves, such as MOVe valves modulate the flow of air pressure, vacuum, or fluids in a microfluidic microchip 2 or multiple microfluidic microchips. MOVe valves can be microscale on-chip valves, microfluidic on-chip valves or micro-robotic on-chip valves. In one embodiment the flow of air pressure, vacuum, or fluids is regulated by one or more variable pressure pumps, such as solenoid valves or solenoid pumps. In one embodiment, a microfluidic microchip is a structure that contains microchannels and/or microtrenches, where a microchannel is a closed structure and a microtrench is an open structure. In one embodiment a microfluidic microchip is a planarr structure. In a related embodiment a microfluidic device comprises a microfluidic microchip with microvalves clustered on one side of a cartridge. In one embodiment (FIG. 3 and FIG. 4) the cartridge (1) can comprise one or more ports (4, 5, 6, 7, 8, 9) to external fluids, air, or vacuum. Functions of the ports can be for waste (4), reagent entry (5), vent (6), sample input (7), product output (8). The cartridge (1) can contain one or more sample input or reaction chambers, (7) and (3).

A single chamber within the cartridge, such as a reaction chamber, can have one or more, or at least one, two, or three fluidic connections to a microchip. For example, reaction chamber (3) can have a fluidic connection to the microchip through connection 120, which is at the base of the chamber, and another fluidic connection to the microchip through port (9), which is connected to chamber (3) through a passageway located at the top of the chamber. The top of chamber (3), port (9), and the passageway between chamber (3) and port (9) can be closed from the exterior environment such that fluids in chamber (3) necessarily are pumped into port (9) when chamber (3) is full and vice versa. Such a chamber or combination or chamber and port can be referred to as a closed chamber. The positioning of the fluidic connections need not necessarily be at the base and top of the chamber, however, fluidic connections at the base and top positions of the chamber allow for reduced trapping of gas in the chamber. Alternatively, reaction chamber (3) can be viewed as a combination of two chambers that are fluidically connected to each other at a top position, which can be within the cartridge, and, where each chamber also has an opening at a base location. The openings at the base locations, also called chamber apertures, can be fluidically connected to port apertures on the microchip. The two fluidic connections can allow for fluids to be directed into and out of the chamber through the microfluidic microchip.

In another embodiment a device comprises a cartridge comprising at least one pneumatically actuated valve, such as a MOVe valve, located on one or more surfaces or structures in a non-linear manner. A cartridge can comprise one or more pneumatically actuated valves that are located within the cartridge, in a location other than the base of the cartridge.

Functional elements of a cartridge can include ports, channels, chambers, filters, magnets, or vents, chambers can be collectively referred to as functional elements. In one embodiment, FIG. 4, the functional elements connect to the microfluidic microchip containing microvalves at junctions 100, 120, 140, 160, and 230. The functional elements can connect with tubing or capillaries inserted into the ports, by a flush connection, or by fittings. In one embodiment a flush connection can comprise a port of a cartridge aligned directly with an aperture of a microfluidic microchip. In one embodiment the cartridge and microfluidic microchip form an integrated module. In another embodiment the cartridge and microfluidic microchip are two separate pieces which are attached together, prior to use.

A cartridge can comprise at least one chamber, a sample input port, a reagent port, an exit port, a waste port and a magnet. The magnet can be located adjacent to the chamber, so that the magnet force generated by the magnet can attract paramagnetic particles in said chamber to a wall of the chamber. In one embodiment the paramagnetic particles are beads or cells rendered magnetically responsive (e.g., cells comprising hemoglobin that are treated with sodium nitrate). The magnet can be an electric magnet or a permanent magnet, such as a rare earth metal magnet.

In one embodiment, FIG. 4, connections or ports (4, 5, 6, 7, 8, and 9) lead to channels in the cartridge (14, 15, 16, 17, 18, and 19) respectively. Ports (4, 5, 6, 7, and 8) show indents to reliably attach a connector or tubing to the indent, such as the indent shown for connection (7) (see the difference in diameter of connection (7) with channel (17)). In one embodiment, the ports or ports can interface with a variety of connector or tubes, such as the capillaries as described in U.S. Pat. No. 6,190,616, U.S. Pat. No. 6,423,536, U.S. application Ser. No. 09/770,412, Jan. 25, 2001, U.S. Application No. 60/402,959 or one or more microchips with modular microfluidic ports as described in U.S. Pat. No. 6,870,185 and U.S. application Ser. No. 11/229,065; all of which are herein incorporated by reference in their entirety. In one embodiment, the modular microfluidic ports enable microchips or capillaries to be reversibly joined without dead volumes or leakage.

In another embodiment chamber (3) is connected to passageway (9) and to cone (13), leading to junction (120). Chamber (3) can be used for reactions as may any of the channels. In FIG. 4 the cartridge channels lead directly to the apertures of ports on the microchip (2). The channels of the cartridge can interconnect with each other as needed. In some embodiments, at least one channel in a cartridge does not physically connect to a microfluidic microchip. In another embodiment at least one channel in a cartridge is fluidically connected to at least one microchannel in a microfluidic microchip. The connection may or may not utilize an aperture on the microfluidic microchip. An aperture can be an opening or a fitting designed to mate between the microchip and the cartridge. In some embodiments of the invention, the fitting comprises a seal such as a gasket or an o-ring.

B. Microchips

In one embodiment a cartridge and a microfluidic microchip are integrated together to form a single modular device. The cartridge and a microfluidic microchip can be attached by a fluid or solid adhesive or mechanically. In one embodiment the adhesive is a polyacrylate, adhesive tape, double-sided tape, or any other adhesive known to one skilled in the art. A cartridge can comprise a feature (12) that is capable of wicking a fluid-based adhesive into the junction between a microfluidic microchip and a cartridge. In another embodiment a cartridge is attached to a microfluidic microchip with a non-fluidic adhesive layer. Alternatively, the cartridge and microchip can be held together by clips, clamps, or another holding device. The cartridge and microchip can be aligned prior to integration by visual cues, with or without a microscope, or by physical guiding features. Visual cues can include lines or features that are drawn, etched, or otherwise present on the cartridge, the microchip, or both. Physical guiding features include indentations, protrusions, and edges that can be 'keyed' to aid or insure proper assembly.

In some instances, the microfluidic microchip has diaphragm valves for the control of fluid flow. Microfluidic devices with diaphragm valves that control fluid flow have been described in U.S. Pat. No. 7,445,926, U.S. Patent Publication Nos. 2006/0073484, 2006/0073484, 2007/0248958, and 2008/0014576, and PCT Publication No. WO 2008/115626, which are hereby incorporated by reference in their entirety. The valves can be controlled by applying positive or negative pressure to a pneumatics layer of the microchip through a pneumatic manifold.

In one embodiment, the microchip is a "MOVe" microchip. Such microchips comprise three functional layers—a fluidics layer that comprises microfluidic channels; a pneumatics layer that comprises pneumatics channels and an actuation layer sandwiched between the two other layers. In certain embodiments, the fluidics layer is comprised of two layers. One layer can comprise grooves that provide the microfluidics channels, and vias, or holes that pass from the outside surface to a fluidics channel. A second layer can comprise vias that pass from a surface that is in contact with the actuation layer to the surface in contact with the pneumatic channels on the other layer. When contacted together, these two layers from a single fluidics layer that comprises internal channels and vias that open out to connect a channel with the fluidics manifold or in to connect a channel with the activation layer, to form a valve, chamber or other functional item. The actuation layer typically is formed of a deformable substance, e.g., an elastomeric substance, that can deform when vacuum or pressure is exerted on it. At points where the fluidic channels or pneumatic channels open onto or are otherwise in contact with the actuation layer, functional devices such as valves can be formed. Such a valve is depicted in cross section in FIG. 1. Both the fluidics layer and the pneumatics layer can comprise ports that connect channels to the outside surface as ports. Such ports can be adapted to engage fluidics manifolds, e.g., cartridges, or pneumatics manifolds.

As shown in FIG. 40, the microfluidic microchip (103) can be interfaced with the cartridge (101). The microfluidic microchip can have a chamber (105) with an opening that is mated to an opening (117) of the cartridge (101). The chamber can be used for a variety of purposes. For example, the chamber can be used as a reaction chamber, a mixing chamber, or a capture chamber. The chamber can be used to capture magnetic particles such as magnetic beads, paramagnetic beads, solid phase extraction material, monoliths, or chromatography matrices.

A magnetic component (109) can be positioned such that magnetic particles in the cartridge reservoir (107) and/or the microfluidic chamber (105) are captured against a surface of the microfluidic chamber (105). The magnetic component can generate a magnetic and/or electromagnetic field using a permanent magnet and/or an electromagnet. If a permanent magnet is used, the magnet can be actuated in one or more directions to bring the magnet into proximity of the microfluidic microchip to apply a magnetic field to the microfluidic chamber. In some embodiments of the invention, the magnet is actuated in the direction (111) indicated in FIG. 40.

Alternatively, any of a variety of devices can be interfaced with the microfluidic microchip. For example detectors, separation devices (e.g. gas chromatographs, liquid chromatographs, capillary electrophoresis, mass spectrometers, etc), light sources, or temperature control devices can be positioned next to the microfluidic microchip or used in conjunction with the microfluidic microchip. These devices can allow for detection of analytes by detecting resistance, capacitance, light absorbance or emission, fluorescence, or temperature or other chemical or physical measurements. Alternatively, these devices can allow for light to be introduced to a region or area of the microfluidic microchip.

A microfluidic device can be designed with multiple chambers that are configured for capture of magnetic particles. The multiple chambers and magnetic component can be arranged such that a magnetic field can be applied simultaneously to all chambers, or be applied to each or some chambers independent of other chambers. The arrangement of chambers and magnetic components can facilitate faster or more efficient recovery of magnetic particles. In particular, the arrangement can facilitate recovery of magnetic particles in multiple chambers.

Figure 41:
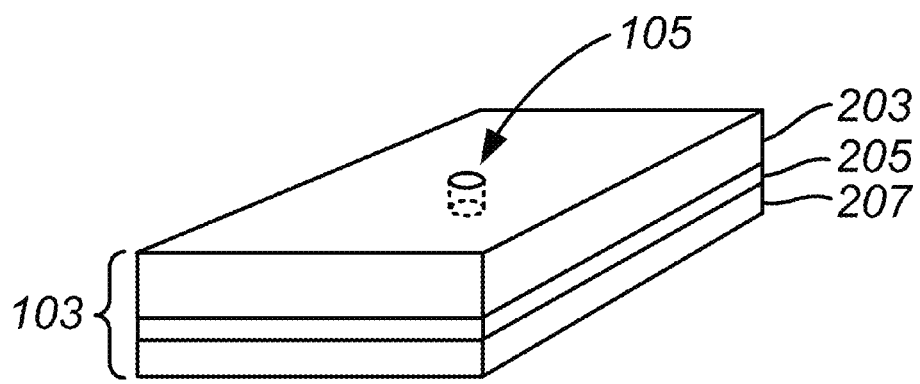
FIG. 41 depicts a microfluidic microchip with a fluidics layer, an elastomeric layer, and a pneumatics layer.

As shown in FIG. 41, the microfluidic microchip (103) can be formed of a fluidics layer (203), an elastomeric layer (205), and a pneumatic layer (207). The fluidics layer can contain features such as a chamber (105), as well as channels, valves, and ports. The channels can be microfluidic channels used for the transfer of fluids between chambers and/or ports. The valves can be any type of valve used in microfluidic devices. In preferred embodiments of the invention, a valve includes a microscale on-chip valve (MOVe), also referred to as a microfluidic diaphragm valve herein. A series of three MOVes can form a MOVe pump. The MOVes and MOVe pumps can be actuated using pneumatics. Pneumatic sources can be internal or external to the microfluidic microchip.

Figure 1:
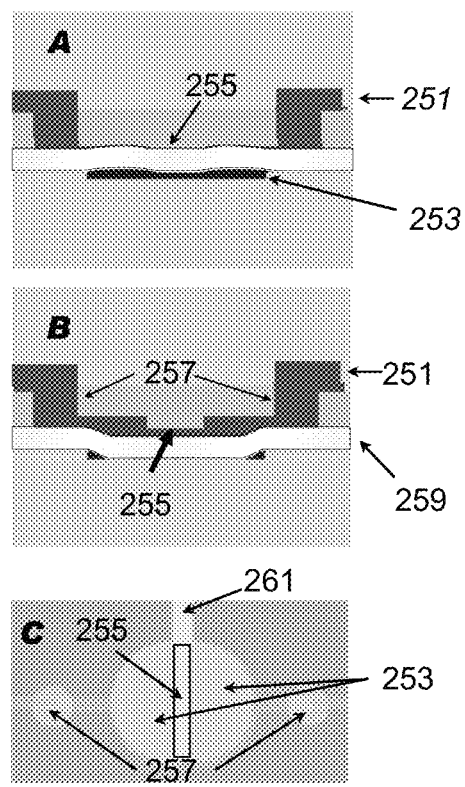
FIG. 1 depicts an example of a microscale on-chip valve (MOVe).
Figure 2:
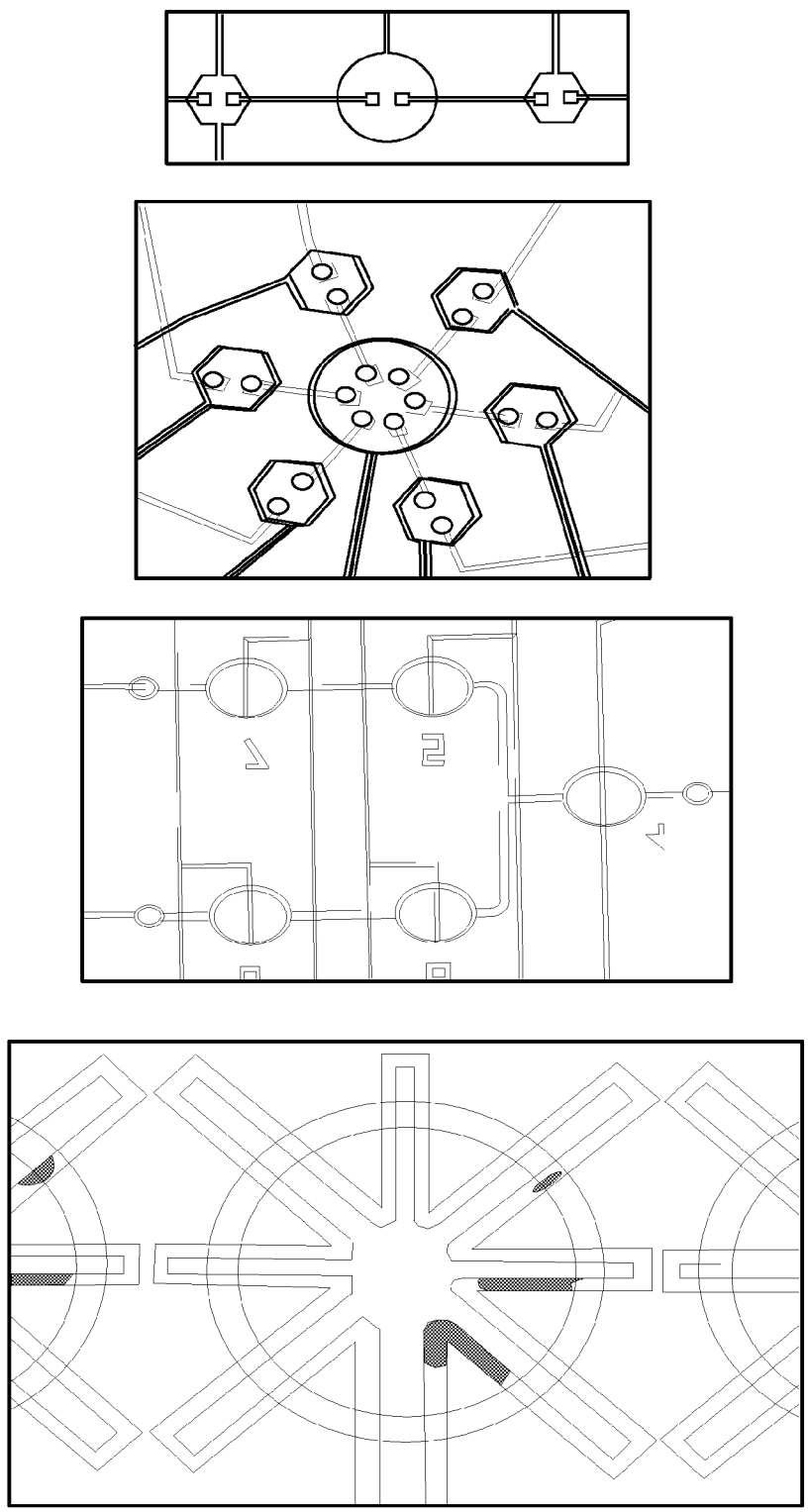
FIG. 2 shows a MOVe microvalve, a microrouter, a MOVe mixer, and bead capture on microchips.

An example of a MOVe valve is shown in FIG. 1. A cross-sectional view of a closed MOVe valve is shown in FIG. 1A. A cross-sectional view of an open MOVe valve is shown in FIG. 1B. FIG. 1C shows a top-down view of the MOVe valve. A channel (251) that originates from a fluidic layer can interface with an elastomeric layer (259) by one or more vias (257). The channel can have one or more seats (255) to obstruct flow through the channel when the elastomeric layer (259) is in contact with the seat (255). The elastomeric layer can either be normally in contact with the seat, or normally not in contact with the seat. Application of positive or negative pressure through a pneumatic line (261) to increase or decrease the pressure in a pneumatic chamber (253) relative to the fluidic channel (251) can deform the elastomeric layer, such that the elastomeric layer is pushed against the seat or pulled away from the seat. In some embodiments of the invention, a MOVe does not have a seat, and fluid flow through the fluidic channel is not completely obstructed under application of positive or negative pressure. The vacuum that can be applied include extremely high vacuum, medium vacuum, low vacuum, house vacuum, and pressures such as 5 psi, 10 psi, 15 psi, 25 psi, 30 psi, 40 psi, 45 psi, and 50 psi.

Three MOVe valves in series can form a pump through the use of a first MOVe as an inlet valve, a second MOVe as a pumping valve, and a third MOVe as an outlet valve. Fluid can be moved through the series of MOVes by sequential opening and closing of the MOVes. For a fluid being supplied to an inlet valve, an exemplary sequence can include, starting from a state where all three MOVes are closed, (a) opening the inlet valve, (b) opening the pumping valve, (c) closing the inlet valve and opening the outlet valve, (d) closing the pumping valve, and (e) closing the outlet valve. Since the inlet and outlet valve can have the same structure, a MOVe pump can move fluids in either direction by reprogramming of the sequence of opening inlet or outlet valves.

Figure 42:
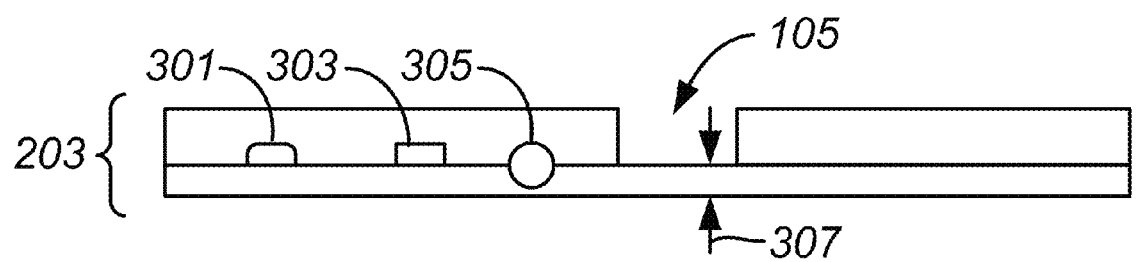
FIG. 42 depicts a fluidics layer made of two layers of material.

The fluidic layer (203) can be constructed of one or more layers of material. As shown in FIG. 42, the fluidic layer (203) can be constructed of two layers of material. Channels (301, 303, 305) can be formed at the interface between the two layers of material, and a chamber (105) can be formed by complete removal of a portion of one layer of material. The channels can have any shape, e.g., rounded and on one side (301), rectangular (303), or circular (305). The channel can be formed by recesses in only one layer (301, 303) or by recesses in both layers (305). The channels and chambers can be connected by fluidic channels that traverse the channels and chambers shown. Multidimensional microchips are also within the scope of the instant invention where fluidic channels and connections are made between multiple fluidic layers.

The thickness (307) of the second layer of material can be of any thickness. In some embodiments of the invention, the second layer has a thickness that minimizes reduction of a magnetic field in the chamber (105) that is applied across the second layer from an external magnetic component or minimizes reductions in heat transfer.

Figure 43:
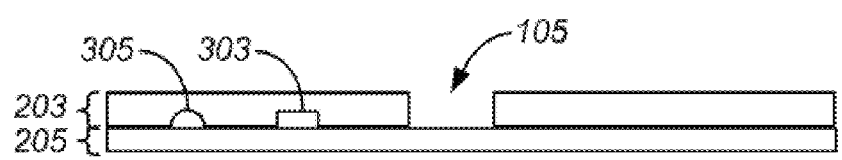
FIG. 43 depicts a fluidics layer made of a single layer of material.

As shown in FIG. 43, the fluidic layer (203) can be constructed of a single layer of material. The single layer is then interfaced with an elastomeric layer, such that channels (305, 303) and chambers (305) are formed between the fluidic layer and the elastomeric layer (205).

The microfluidic microchip can be constructed from any material known to those skilled in the art. In some embodiments of the invention, the fluidics and pneumatic layer are constructed from glass and the elastomeric layer is formed from PDMS. In alternative embodiments, the elastomer can be replaced by a thin membrane of deformable material such as Teflon (PTFE), silicon, or other membrane. The features of the fluidics and pneumatic layer can be formed using any microfabrication technique known to those skilled in the art, such as patterning, etching, milling, molding, embossing, screen printing, laser ablation, substrate deposition, chemical vapor deposition, or any combination thereof.

Figure 5:
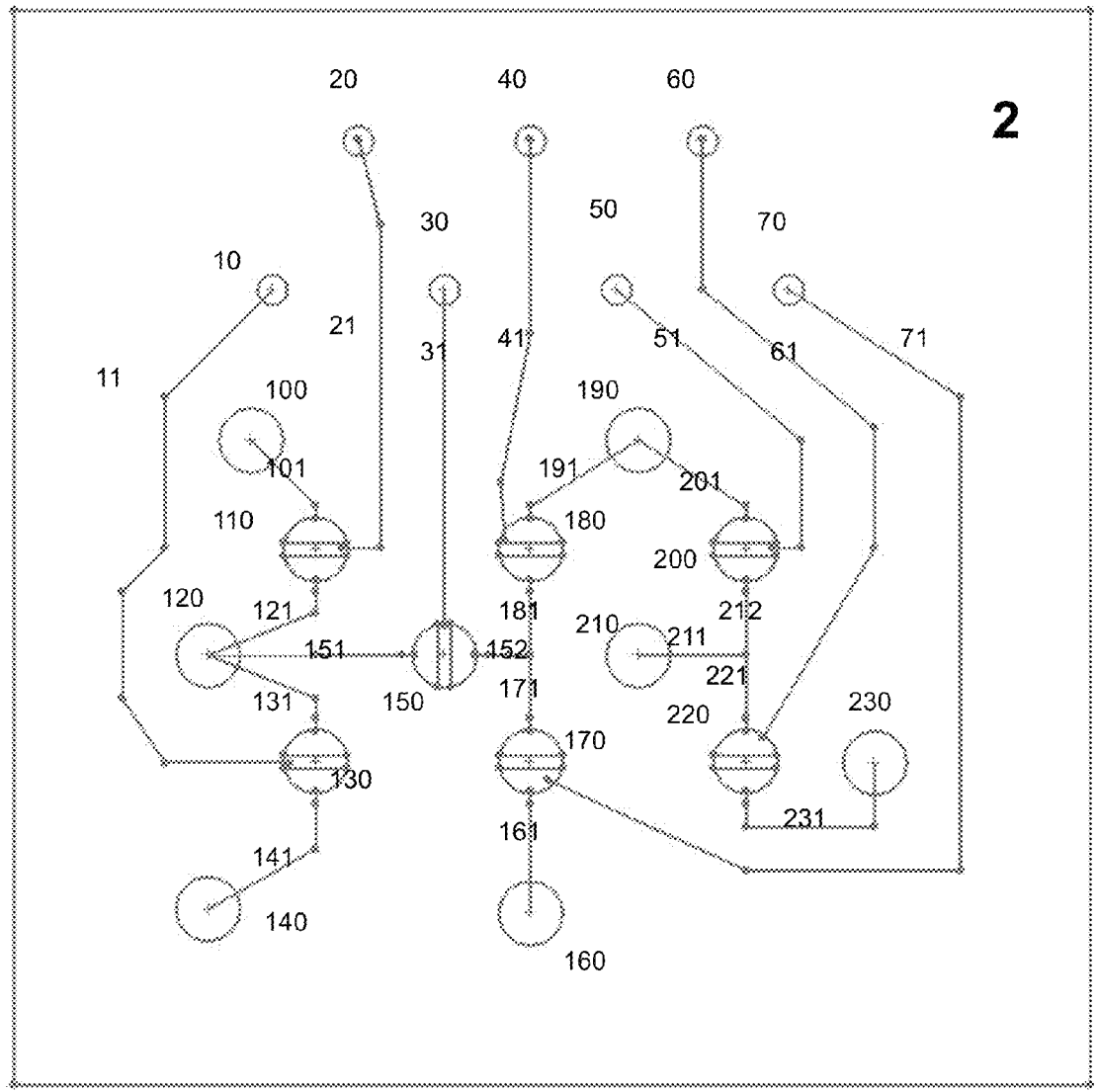
FIG. 5 shows a microfluidic microchip with MOVe valves that controls flows in a cartridge.

In one embodiment, microchannel circuits are formed on a microfluidic microchip 2, as shown in FIG. 5, linking sets of microvalves with microchannels. In one embodiment the microvalves are pneumatically actuated valves. In one embodiment the pneumatically actuated valves are MOVe microvalves. In one embodiment, the fluidic path between a cartridge and a microfluidic microchip, such as between chambers, ports, channels, microchannels, and other functional elements can be controlled by opening or closing at least one microvalve. In one embodiment the microvalve is controlled by a microprocessor control such as a computer. A computer can include an input/output controller, or any other components known to one skilled in the art such as memory storage and a processor. In one embodiment, a microvalve is a MOVe valve that is actuated by a pneumatic source, such as through pneumatic ports 10, 20, 30, 40, 50, 60, or 70. In one embodiment the pneumatic source is controlled by at least one solenoid. In one embodiment the solenoid is miniaturized and can be connected to vacuum or pressure sources. In one embodiment the pneumatic source is connected to a pneumatic port using a force such as clamping, springs, pneumatics, or a screw force, optionally with sealing provided by an o-ring.

In one embodiment FIG. 5 shows a view of the top of a microfluidic microchip (2), this side makes contact with the bottom of cartridge (1). A microvalve 110 controls the fluidic path between microchannels 101 and 121. A microvalve 130 controls the fluidic path between microchannels 131 and 141. Microvalve (150) controls the fluidic path between microchannels 151 and 152. Microvalve 180 controls the fluidic path between microchannels 181 and 191. Microvalve 200 controls the fluidic path between microchannels 201 and 212. Microvalve 220 controls the fluidic path between microchannels 221 and 231.

In one embodiment junctions can connect one or more microchannels. FIG. 5 shows the schematic for a microchip that can be mated with the cartridge shown in FIG. 4. In FIG. 5, junction 100 connects to single microchannel 101, junction 140 connects to single microchannel 141, junction 160 connects to single microchannel 161, and junction 230 connects to single microchannel 231. Junction 190 connects to two microchannels 191 and 201. Junction 120 connects to three microchannels 121, 131, and 151. In one embodiment more than three microchannels can be connected to a single junction.

The microchannels can be fabricated by one or more techniques such as photolithography, molding, embossing, casting, or milling. The microchannels can be manufactured in a material such as glass, plastic, polymer, ceramic, gel, metal, or another suitable solid.

Figure 28:
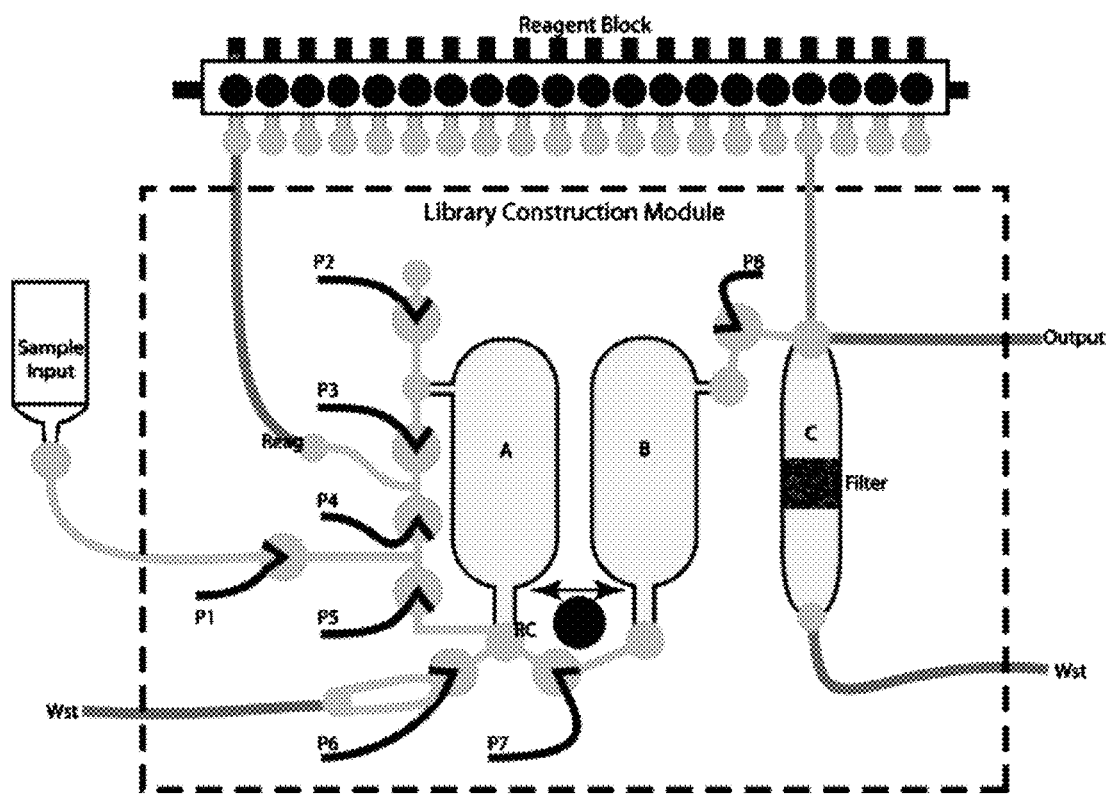
FIG. 28 shows application of a cartridge with three chambers that can be used to construct genomic libraries and other applications.

In another embodiment a device comprises a cartridge comprising at least three chambers, more than one input port and more than one output port (FIG. 28). The cartridge can be adapted to process a nucleic acid sample for analysis. The cartridge can be adapted to receive one or more reagents from an external reagent source. The reagents can be a paramagnetic bead, a non-paramagnetic bead, an enzyme, a dNTP, a buffer solution, a salt solution, an alcohol solution, an solution comprising EDTA or an oligonucleotide or other reagents. The enzymes can be a ligase, a restriction enzyme, a polymerase, or a kinase or any other enzyme or catalytic biomaterials including RNAs. The device can comprise a magnet which can attract paramagnetic beads to a wall of one or more chambers. In another embodiment at least one chamber comprises a filter to capture beads, such as non-paramagnetic beads.

In one embodiment the cartridge is used in a method of sample enrichment comprising: delivery of a sample to a chamber by a sample port and delivery of paramagnetic particles to a chamber by a reagent port. The paramagnetic particles (e.g. paramagnetic beads) bind to at least one component in the sample (such as DNA, RNA, micro RNA, a protein, a lipid, a polysaccharide or other ligand). The paramagnetic particles are attracted to a wall of a chamber by virtue of the Magnetic force exerted by a magnet located outside the chamber. The paramagnetic particles are washed with a wash solution delivered to the chamber comprising the paramagnetic particles by a reagent port, and the wash solution is removed by a waste port. A reagent can be added to elute the component of the sample from the paramagnetic particles and output the sample component to another device for further processing or analysis. A preferred embodiment is to output the component of the sample on the paramagnetic particles.

In one embodiment a device comprising a microfluidic microchip is used in a method of diagnosis. In one embodiment the diagnosis comprises the detection of an infectious agent in a sample. In one embodiment the infectious agent is a bacteria, virus, fungi, mycoplasm or prion. In another embodiment a device comprising a microfluidic microchip is used in a method of diagnosis of a hereditary disease. In one embodiment the hereditary disease is caused by one or more DNA mutations, such mutations include but are not limited, triplet base expansions, base substitution mutations, deletion mutations, addition mutations, nonsense mutations, premature stop codons, chromosomal deletions, chromosomal duplications, aneuploidy, partial aneuploidy or monosomy. In another embodiment a device comprising a microfluidic microchip is used in a method to diagnose cancer or a predisposition to cancer. In another embodiment a device comprising a microfluidic microchip is used in a method to diagnose a hereditary disease such as autism, downs syndrome, trisomy, Tay-sachs, or other hereditary diseases. In some embodiments a sample used for diagnosis in a device comprising a microfluidic microchip is a blood sample, a mucus sample, a lung lavage sample, a urine sample, a fecal sample, a skin sample, a hair sample, a semen sample, a vaginal sample, or an amniotic sample.

In another embodiment a device comprising a microfluidic microchip is used to identify the presence of environmental contamination of an agent. In one embodiment the agent is a biological agent such as bacteria, virus, fungi, or mycoplasm in an environmental sample. In another embodiment the agent is a contaminant agent, such as a pesticide, an herbicide, or a fertilizer. In one embodiment the environmental sample is a soil sample, a water sample, an air sample, a meat sample, a vegetable sample or a fruit sample. In another embodiment, the agent is a genetically modified organism.

In another embodiment a device comprising a microfluidic microchip is used for genotyping, identification of an individual mammal (such as a human), forensics, gene expression, gene modification, microRNA analysis, or ribotyping.

In another embodiment a microfluidic microchip is used in a method comprising molecular biological analysis, including but not limited to polymerase chain reaction (PCR) amplification of nucleic acids in a sample (such as Allele-specific PCR, Assembly PCR, Asymmetric PCR, Colony PCR, Helicase-dependent amplification, Hot-start PCR, Intersequence-specific (ISSR) PCR, Inverse PCR, Ligation-mediated PCR, Methylation-specific PCR Multiplex Ligation-dependent Probe Amplification, Multiplex-PCR, Nested PCR, Overlap-extension PCR, Quantitative PCR Reverse Transcription PCR-PCR, Thermal asymmetric interlaced-PCR, Touchdown PCR, or PAN-AC PCR), isothermal nucleic acid amplifications, (such as Loop-mediated Isothermal Amplification (LAMP); nick displacement amplification; Helicase Dependant Amplification platform (HDA); and the primase-based Whole Genome Amplification platform (pWGA); single primer isothermal amplification (SPIA) and Ribo-SPIA for RNA; strand displacement amplification (SDA); EXPAR [Van Ness J, Van Ness L K, Galas D J. (2003) Isothermal reactions for the amplification of oligonucleotides. Proc Natl Acad Sci USA. 100:4504-9.]; rolling circle amplification (RCA); transcription-based amplification system (TAS) and its derivatives include self-sustaining sequence replication (3SR), isothermal nucleic acid sequence-based amplification (NASBA), and transcription-mediated amplification (TMA); ligase chain reaction (LCR)), sequencing reactions of DNA or RNA (such as Maxam-Gilbert sequencing, Sanger chain-termination method, Dye-terminator sequencing Emulsion PCR sequencing, massively parallel sequencing, polony sequencing, sequencing by ligation, sequencing by synthesis, or sequencing by hybridization), restriction fragment length polymorphism (RFLP) analysis, single nucleotide polymorphism (SNP) analysis, short tandem repeat (STR) analysis, microsatellite analysis, DNA fingerprint analysis, DNA footprint analysis, or DNA methylation analysis.

In one embodiment a cartridge employs beads coupled to a binding moiety, including but not limited to a binding receptor, transferrin, an antibody or a fragment thereof (such as an Fc fragment or an Fab fragment), a lectin, or a DNA or RNA sequence. In another embodiment a cartridge comprises a reagent such as an anti-coagulant, a fixative, a stabilization reagent, a preservative or precipitation reagent.

C. Pneumatic Manifold

A pneumatic manifold can be integrated with any microchip and/or cartridge described herein to facilitate distribution of air pressure or vacuum. The air pressure or vacuum can be used to actuate valves on the microchip. Alternatively, air pressure or vacuum can be supplied to a cartridge such that air pressure or vacuum is provided to microchannels within the fluidics layer of a microchip which can be used to move fluids or gases within the fluidics layer. A pneumatic manifold provides the air pressure or vacuum to operate microvalves on microchip (2) on cartridge (1) of FIG. 3 or operate microvalves in other devices.

A pneumatic manifold can be used to mate the pneumatic lines of a microfluidic microchip to external pressure sources. The pneumatic manifold can have ports that align with ports on the pneumatics layer of the microfluidic microchip and ports that can be connected to tubing that connect to the external pressure sources. The ports can be connected by one or more channels that allow for fluid communication of a liquid or gas, or other material between the ports.

The pneumatic manifold can be interfaced with the microfluidic microchip on any surface of the microchip. The pneumatic manifold can be on the same or different side of the microfluidic microchip as the cartridge. As shown in FIG. 40, a pneumatic manifold (113) can be placed on a surface of the microfluidic microchip opposite to the cartridge. As well, the pneumatic manifold can be designed such that it only occupies a portion of the surface of microfluidic microchip. The positioning, design, and/or shape of the pneumatic manifold can allow access of other components to the microfluidic microchip. The pneumatic manifold can have a cut-out or annular space that allows other components to be positioned adjacent or proximal to the microfluidic microchip. This can allow, for example, a magnetic component (109) to be placed in proximity of a chamber within the microfluidic microchip.

A pneumatic manifold can be constructed of any material known to those skilled in the art. For example, the cartridge can be constructed of a plastic, glass, or metal. A plastic material includes any plastic known to those skilled in the art, such as polypropylene, polystyrene, polyethylene, polyethylene terephthalate, polyester, polyamide, poly(vinylchloride), polycarbonate, polyurethane, polyvinyldiene chloride, cyclic olefin copolymer, or any combination thereof The pneumatic manifold can be formed using any technique known to those skilled in the art, such as soft-lithography, conventional lithography, milling, molding, embossing, drilling, etching, or any combination thereof.

A pneumatic manifold (370) was designed (FIG. 20) that eliminates over twenty tubing ports and provides a robust, reproducible interface between the control system, the pneumatic solenoids and the MOVe input ports. The manifold (370) has a gasket (380) and a bottom plate (390) that are fastened together. The cartridge (1) is held on the plate (370) by a bracket in position to align the pneumatic ports 10, 20, 30, 40, 50, 60, and 70 on microfluidic microchip (2), shown in FIG. 5, with the pneumatic lines shown of the reverse side of 370 in the FIG. 20 insert. The external pneumatics are controlled by a solenoid valve bank that can be miniaturized and can be connected to vacuum or pressure sources.

Figure 20:
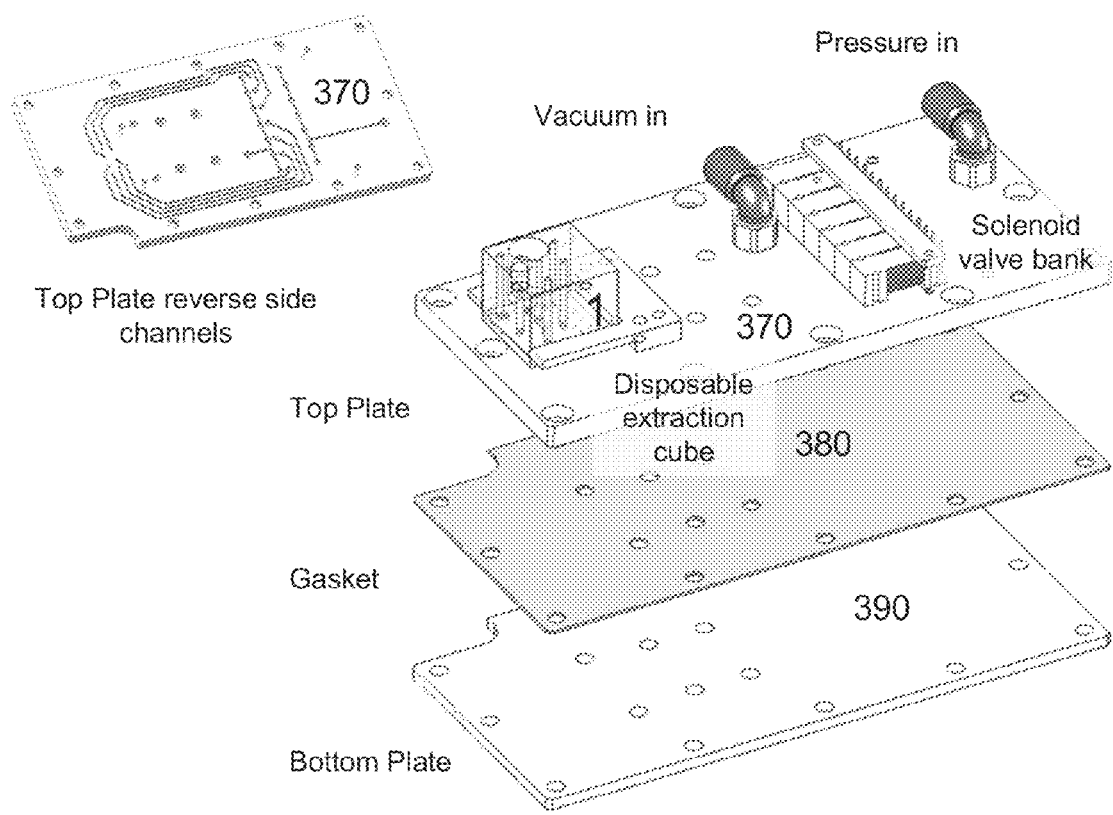
FIG. 20 shows an integrated pneumatic manifold to operate the MOVe microvalves in cartridge.

The apparatus shown in FIG. 21 and FIG. 22 can incorporate the pneumatic manifold shown in FIG. 20. The apparatus can be used for sample preparation, as described herein, and can incorporate a cartridge. Cartridge (1), labeled 'cube', is attached to manifold (370) with solenoids (1819). The assembly of the cartridge and manifold is mounted on a base plate of the apparatus. The pneumatic manifold can be controlled by an IO controller (1803).

A gas supply, such as a reservoir that can be maintained at a desired pressure or vacuum, can supply gas to the manifold. The gas supply can be connected to an outside pressure or vacuum source. The gas supply feeding the gas supply manifold can have a pressure gauge to monitor the inlet pressure. The gas supply can supply gas to multiple components of the system through a gas supply manifold (1821). The gas supply manifold can supply gas to the pneumatic manifold (370) and to individual reagent containers, (1809) and (1807). The line supplying the distribution valve (390) with gas can be regulated by a regulator (1815).

Reagents and/or sample can also be supplied to the cartridge through the reagent distribution valve (390) that is connected to containers (1809) in a reagent storage region (380) and a bead solution container (1807) that is mounted on a bead mixer (1805). Adapter (1817) can be mounted and/or aligned with the cartridge such that a delivery device, such as a syringe, can deliver a material to the cartridge. The adapter (1817) can be thermally regulated by a heater control (1801). The adapter can have a thermal conductor, such as brass, to distribute heat generated by heater coil or a Peltier device. The adapter can maintain temperature between about 20 to 100, 20 to 75, or 50 to 60 degrees Celsius.

A magnet assembly (1811) can be positioned adjacent to the cartridge. A magnet (300) of the magnet assembly can be positioned adjacent to the cartridge (1) and moved by an actuator, such that the magnet can exert a magnetic field within the cartridge, or a microchip integrated, mated, or interfaced with the cartridge. The magnetic field can be used to capture paramagnetic or magnetic particles, such as beads, within the cartridge or microchip and separate material bound to the particles from waste materials. Waste from the cartridge and/or microchip can be delivered to a waste container (1813).

Figure 23:
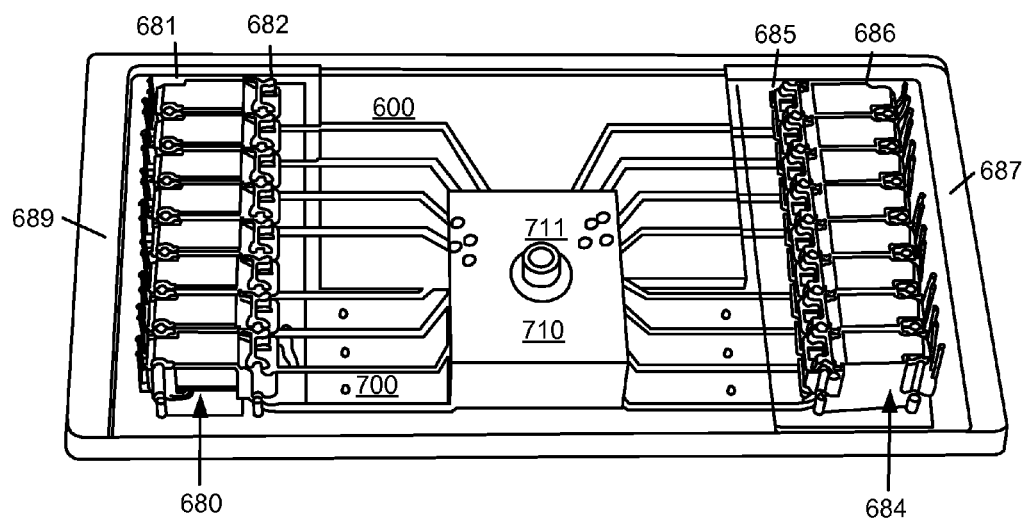
FIG. 23 shows a reagent distribution manifold based on MOVe technology that can distribute five reagents to five extraction/isolation or other devices.
Figure 24:
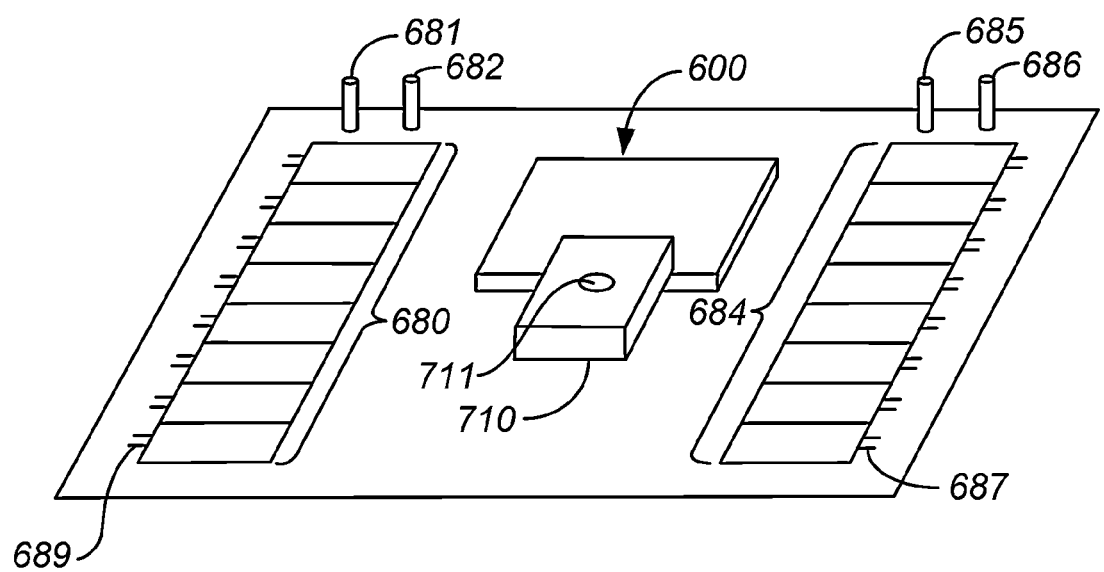
FIG. 24 shows a reagent distribution manifold based on MOVe technology that can distribute five reagents to five extraction/isolation or other devices.

The apparatus shown in FIG. 21 and FIG. 22 can use seven solenoid valves to operate the cartridge (1). The size and complexity of the apparatus can be further reduced with MOVe microvalves. FIG. 23 and FIG. 24 shows a reagent distribution device that contains microfluidic microchip 600, which is approximately two inches wide. Solenoid banks 680 and 684 provide connection to full scale external vacuum and pressure through connectors 681, 682, 685, and 686. The solenoids are controlled through electrical junctions 689 and 687. The microfluidic microchip 600, which has MOVe valves, is held in contact with the manifold 700 by attachment 711 using clamp 710. Other methods known to one skilled in the art can be used to connect the microchip to the pneumatics manifold 700.

Figure 25:
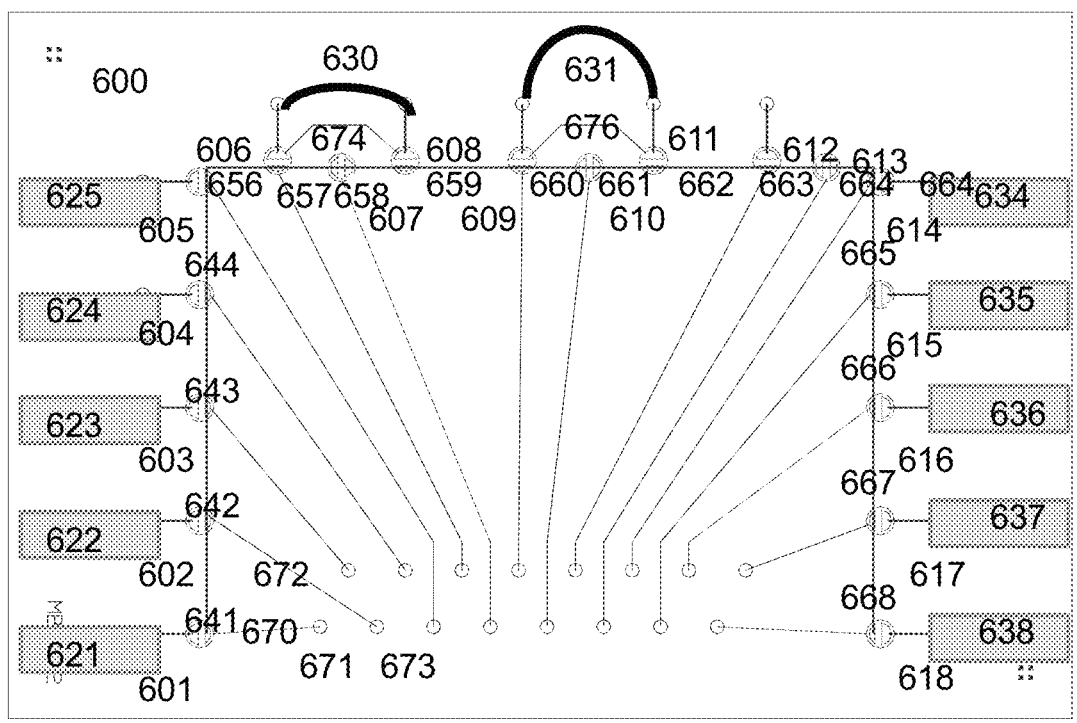
FIG. 25 shows a distribution manifold with sample loops and MOVe microvalves.

As shown in FIG. 25, microchip 600 connects five reagent sources, 621, 622, 623, 624, and 625 with two sample loops 630 and 631 and five devices 634, 635, 636, 637, and 638 which may be microfluidic devices such as cartridge (1). Sample loops 630 and 631 can be configured to have predetermined volumes. The sample loops can have a portion which is removable. Thus, they can be removably connectable to ports in the fluidic manipulation module. The sample loop can be removed to allow for adjustment of the volume of the sample loop. A portion of the sample loop can be capillary tubing, any other type of tubing, or a microfluidic channel. The sample loop can be connected to the microchip using any type of junction described herein. For example, a junction can connect to a cannula, an upfit tubing, a microtubing fitting, an Upchurch tubing adapter, or a FROLC connector [Jovanovich, S. B., G. Ronan, D. Roach and R. Johnston. Capillary valve, connector, and router. Feb. 20, 2001. U. S. Pat. No. 6,190,6161]. It is apparent that the number of reagent sources, microfluidic devices, and sample loops can be increased or decreased. Each microfluidic device can perform the same function, different, or complementary functions. The devices can be connected through modular microfluidic ports.

In an aspect of this invention shown in FIG. 25, a microchip (600) comprises a main microfluidic channel that intersects with two other second microfluidic channels. The main microfluidic channel can be a channel that connects the reagent source 625 with device 634, as shown in FIG. 25. The second channels can be the channel that connect valve 606 to the sample loop 630 and the channel that connects valve 608 to sample 630. At least one, and optionally both, of these second channels connects with the main channel through a flow-through valve (606 and 608) that allow a fluid to flow through the main channel but only into or out of the second channel with the flow through valve is open. The flow-through valve can be redesigned as an in-line valve. The main channel also comprises an intermediate valve (674) between the points of intersection of the two second channels. Each second channel opens from the microchip at an entry port. A sample loop (630) having a channel of defined volume is removably attached to each of the entry ports. Thus, a specific volume of fluid in the sample loop can be injected into the main channel by closing the intermediate valve (674), opening the flow through valves (606 and 608) and applying pressure to the main channel. The sample loop can also be referred to as a fluid loop or reagent loop.

The microchip 600 of the distribution manifold uses eighteen microvalves 601 to 618 to direct flow through the manifold. The microvalves are operated through pneumatic ports with o-rings or other connectors including modular microfluidic ports to pneumatic manifold 700. For example, connection 671 provides pressure or vacuum to microvalve 641 and connection 673 provides pressure or vacuum to microvalve 642. The flow of reagents from reagent sources, 621, 622, 623, 624, and 625 can be directed to fill the sample loops individually or to move samples to devices 634, 635, 636, 637, and 638.

Figure 26:
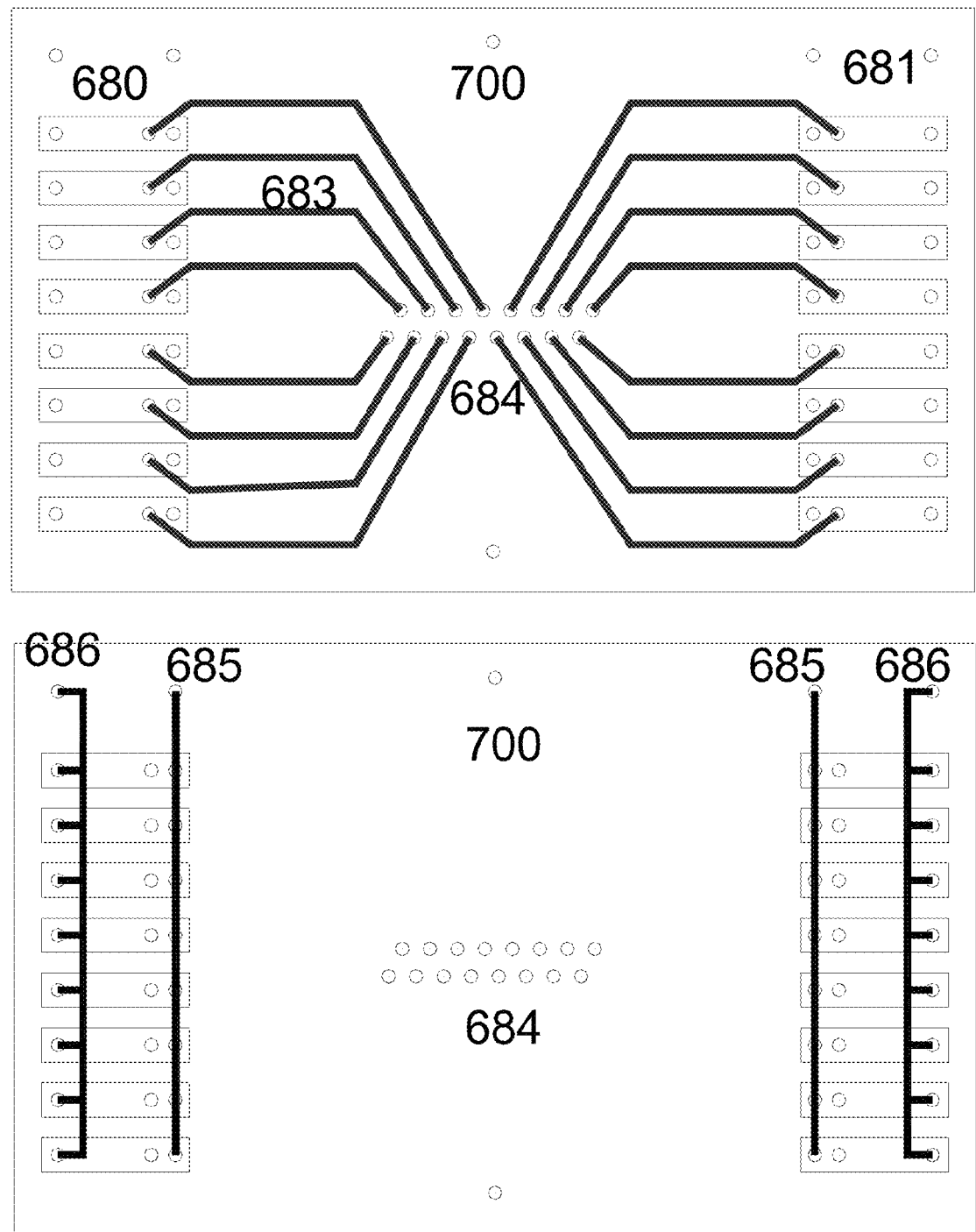
FIG. 26 shows a pneumatic manifold, top panel shows the top side and the lower panel the bottom side.

The pneumatics on manifold 700, as shown in FIG. 26, connects pressure sources 685 and vacuum sources 686 through solenoid banks 680 and 681 to pneumatic channels 683 leading to the array of ports 684 that includes ports 671 and 673. The top portion of FIG. 26 shows the pneumatic lines of the pneumatic manifold that lead into the pneumatic layer of a microchip from the solenoids. The bottom portion of FIG. 26 shows the solenoids and vacuum (685) and pressure source (686) that are connected to each solenoid. The solenoid banks are controlled by electronics to open and close each individual solenoid to the common vacuum or pressure sources. The individual vacuum or pressure control is also envisioned.

The pneumatic manifold 700, shown in FIG. 23, can operate the microvalves 601 to 618 on microfluidic microchip

600, shown in FIG. 25. For example, to move a reagent from reagent source 622 to sample loop 630, microvalves 602, 606, and 608 are opened and pass-through valve 658 is closed. Alternatively, reagent can by-pass sample loop 630 by closure of T-valves 606 and 608 and opening pass-through valve 658. The valves can be controlled by pneumatic lines that are fluidically connected to the pneumatic manifold. For example, pneumatic line 672 is controlled by a solenoid on pneumatic manifold 700, shown in FIG. 23, to open or close the microvalve 642. Valves 603, 604, 605, 609, 610, are always open to flow through the microfluidic circuit containing microchannels 641 to 644 and 656 to 668. The reagent is moved into sample loop 630.

The circuit between 622 and 612 can be overfilled if desired or precisely controlled by MOVe microvalves to modulate flow or control of timing. Once the sample loop 630 is filled, a defined volume has been selected. The microfluidic circuit can be cleaned by flushing cleaning solutions or air or gas through the main channel to further define the reagent volume. If reagent source 621 was a compressed air or gas source (pressure and vacuum are types of reagents in a pressurized flow system), opening microvalve 601 and microvalves 606, 610, and 616 creates the circuit to move the measured reagent in sample loop 630 to device 636. In one embodiment a means to connect any number of reagent sources to a microdevice such as cartridge (1) is provided.

II. Parallel Processing of Samples

In some embodiments of the invention, one or more cartridges can be operated simultaneously to allow for parallel processing of samples. FIG. 16 illustrates parallel or ganged operation of multiple cartridges with microvalves on a single pneumatic manifold in swab extraction assembly (800). The manifold (370) distributes regulated vacuum and pressure to operate four cartridges (1), indicated in the figure, using solenoids (680). Solenoids (680) control pressure to the pneumatic layer of a microchip integrated with each cartridge through the pneumatic manifold (370, 380, 390). The pneumatic manifold is formed by a top plate (370), a gasket (380) and a bottom plate (390). The top plate can have channels etched into it. The channels can be sealed by the gasket, which is sandwiched against the top plate by the bottom plate (390). Actuator 310 moves rod 810 to move magnets (320) close to or away from the cartridges (1). Clamps 805 hold cartridges (1) in place.

Figure 14:
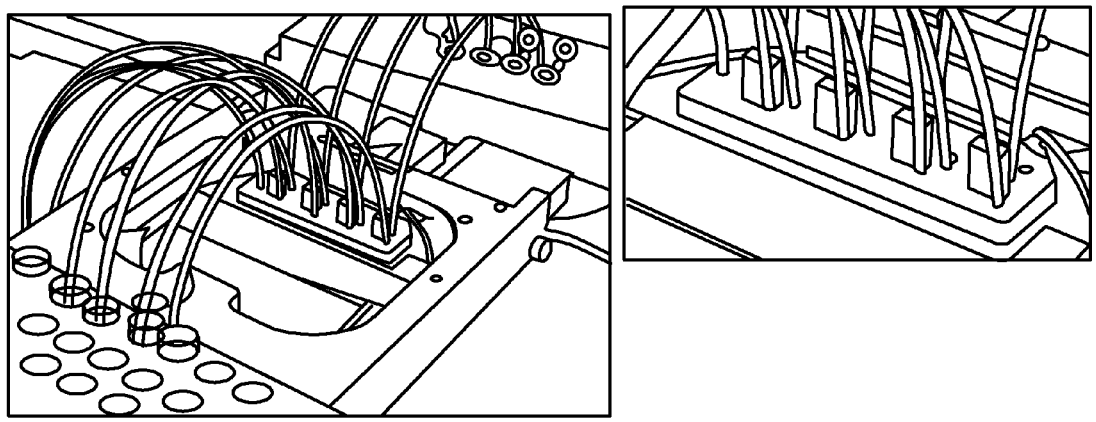
FIG. 14 shows a capture and reaction microchip using MOVe microvalves.
Figure 15:
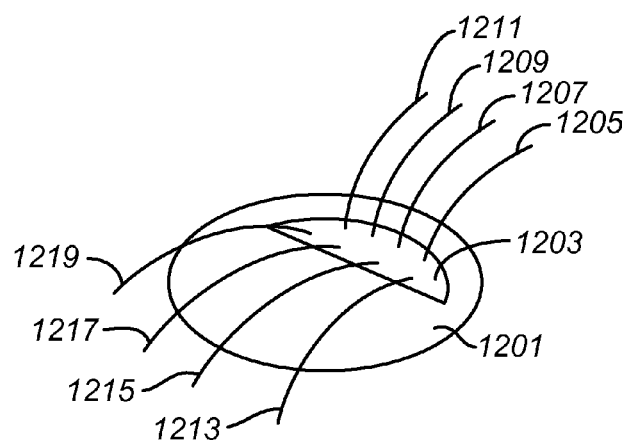
FIG. 15 shows a capture and reaction microchip using MOVe microvalves.

In other embodiments of the invention, a single cartridge integrated with a microchip can process multiple samples at one time using parallel channels. FIG. 14 and FIG. 15 shows an assembled capture and reaction microchip with capillary feed and magnets. This microchip can capture bead solutions and perform four STR-PCR reactions simultaneously. FIG. 14 shows a microchip (1201) with a cartridge (1203) adhered to the microchip and tubes (1205, 1207, 1209, 1211, 1213, 1215, 1217, and 1219) leading into and out of the microchip. A total of eight tubes are shown and two tubes are used per parallel reaction. For example, one unit of the parallel processing device is served by tubes 1205 and 1213.

Figure 66:
FIG. 66 shows a diagram indicating movement of reagents between components of a four channel parallel processing device.
Figure 67:
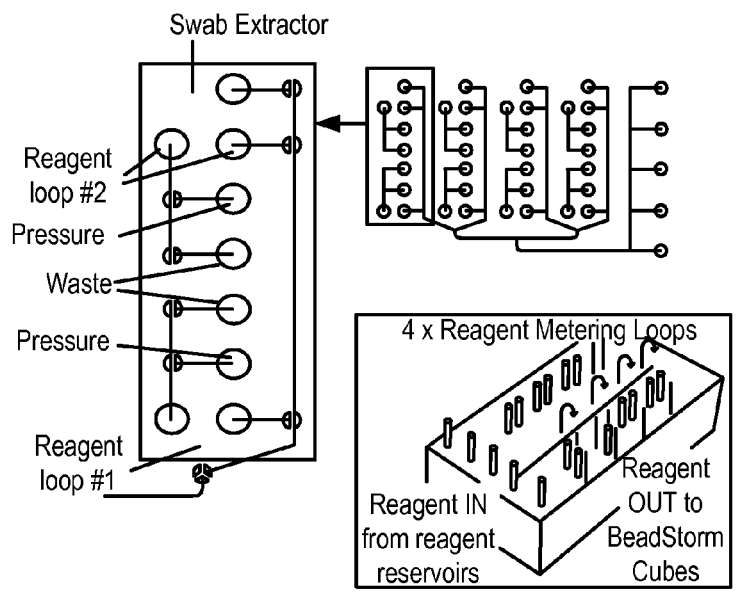
FIG. 67 shows a four-channel parallel reagent delivery device: the Chip C microchip design is shown on the top left, a fluidic manifold is shown on the bottom left, and the fabricated and assembled device is shown on the right.
Figure 67:
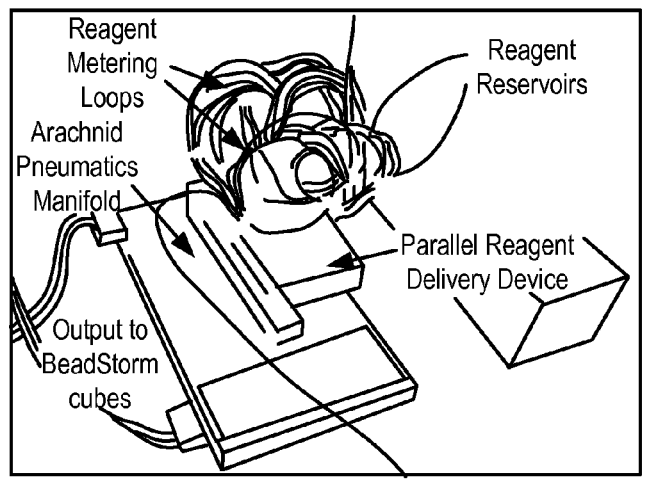

In another embodiment, a four-channel sample preparation device (FIG. 66) combines a four-channel parallel reagent delivery device (FIG. 67) that meters and delivers reagents simultaneously to all four channels of a single integrated cartridge (FIG. 68) enabling four samples to be processed simultaneously and rapidly.

The four-channel parallel reagent delivery device combines an Chip C microchip (see FIG. 67) with a fluidics manifold mounted on a pneumatics control manifold. Reagents are metered, using one of the two different size reagent loops, which can be similar to the sample loops described herein, for each channel, and delivered in parallel to all four channels of the sample preparation device. Delivering reagents simultaneously to all four channels of the sample preparation device using the parallel reagent delivery device can takes <4 minutes, representing a process time saving of >11 minutes as compared to the first generation serial reagent delivery device that took ~15 minutes per four samples processed.

Bonded pneumatics manifolds can be used to control both the reagent delivery and sample preparation devices by fabricating the manifolds using an adhesive bonding approach; however, these may be prone to delamination over time due to the pneumatic pressures used in the subsystem, and the size and complexity of the manifold. Thermally bonded manifolds can mitigate delamination issues, but may only be a viable approach for relatively small and low complexity manifold designs such as the reagent delivery device. A monolithic manifold made from a single piece of polycarbonate with tubing connecting pneumatic ports to the solenoid control valves can operate the four-channel sample preparation cartridge and has proved to be a viable alternative to bonded pneumatic manifolds, see FIG. 45 and FIG. 46 for examples. This pneumatic manifold design concept is also being utilized for control of the Chip A microchip on the Post-amplification STR (Single Tandem Repeat) clean-up subsystem.

Assembly processes for the microchip and fluidic manifold of the four-channel sample preparation cartridge have also been improved. Historically, silicon epoxy can be used to attach the cartridge to its associated MOVe microchip by wicking the adhesive between the microchip and the cube. An inherent lack of control of the movement of the epoxy can allow it to occasionally wick into the ports on either the microchip or the cube creating a blockage in the fluidic pathway rendering the device unusable. This process has been improved by using a double-sided adhesive tape (Adhesives Research ARcare90106) to assemble the fluidic cubes and microchips; this is now the preferred assembly method used for the four-channel reagent delivery cartridge, the sample preparation device, and the post amplification device in the Post-amplification STR clean-up subsystem described below.

Figure 69:
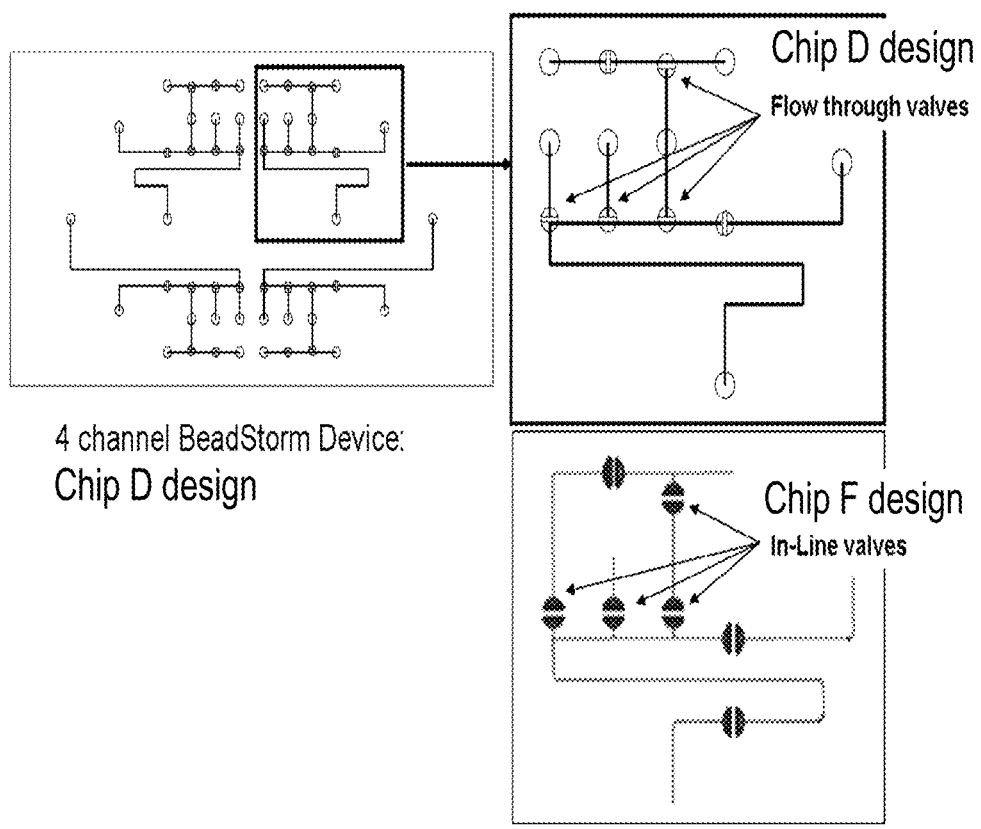
FIG. 69 shows MOVe microchip designs of the four-channel sample preparation device: the Chip D microchip design is shown on the left with flow through valves that form a T-junction between two bisecting channels shown in top panel; the Chip D microchip design with flow-through valves is shown on the right top; the Chip F microchip design with in-line valves that have only one channel passing through the middle of the valve is shown on the right bottom.

The integrated four-channel sample preparation cartridge with the Chip D microchip (see FIG. 69) was tested. The Chip D microchip, shown in FIG. 69 on the left panel, highlighted an issue with the design wherein the PDMS membrane inadvertently closed off fluidic channels adjacent to flow through valves on the MOVe microchip. Without being limited to theory or conjecture, it is thought that this effect is due to a combination of variables including minor differences in alignment during microchip assembly, the etch depth of the microchip's fluidic layer, and the pneumatic pressure used to operate the microchip on the sample preparation device. A microchip, Chip E, shown in FIG. 69 right panel, was been designed to convert all flow through valves that form a T-junction between two bisecting channels in the Chip D microchip, to in-line channel that have only one channel passing through the middle of the channel. The Chip E microchip can reduce the occurrence of inadvertent channel closure during valve closure. In FIG. 69, left panel, the four circles in that are positioned along the middle of the microchip can be operated independently and are each fluidically connected to a swab extraction device that can be used to extract analytes from a swab. Other ports in the microchip can connect to chambers in a cartridge (similar to the ports and chambers described for FIG. 3 and FIG. 4) that are mated to the microchip (shown in FIG. 68) for performing reactions, such as nucleotide binding. Operation of the integrated four-channel sample preparation cartridge with microchip is similar to the operation of the device shown in FIG. 3 and FIG. 4.

Microchip blockages due to the inadvertent introduction of fibers into the systems and devices described herein can be problematic in microfluidics. To minimize blockages, all reagents with the exception of paramagnetic bead solutions, can be filtered prior to loading and in-line filters used to minimize microchip blockages.

Figure 70:
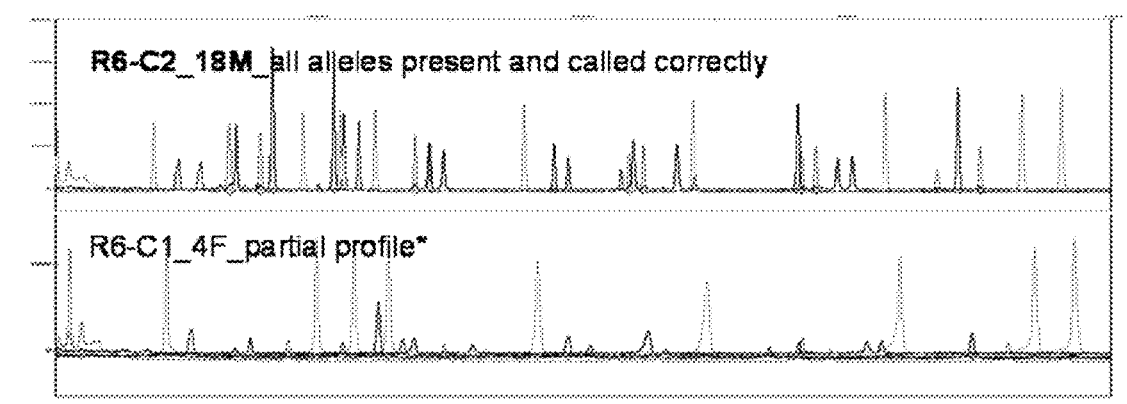
FIG. 70 shows IdentiFiler STR profiles of DNA samples prepared on the four-channel sample preparation device, where STR amplifications were performed using fast protocols (1.5 hrs) on a STR Reaction subsystem thermocycler.

Subsystem testing of the second-generation sample preparation device focused on characterization of system reproducibility and failure modes. A total of 80 samples were processed on the subsystem with a success rate of 63%. Failure modes included Reagents line accidentally becoming disconnected (2.5%), chip blockages (3.75%), no STR profiling observed (9%), and DNA yield <0.08 ng (22%), which is the limit of detection of the downstream system. The average yield of purified DNA yield was found to be 0.26 ng. Approximately half of the samples tested in STR reactions gave full profiles and half gave partial profiles (see FIG. 70). A number of blank samples were processed on the system using cleaned and recycled cartridges, and run-to-run cross contamination was found to be negligible.

III. Integrated Sample Preparation and Polymerase Chain Reaction

Figure 6:
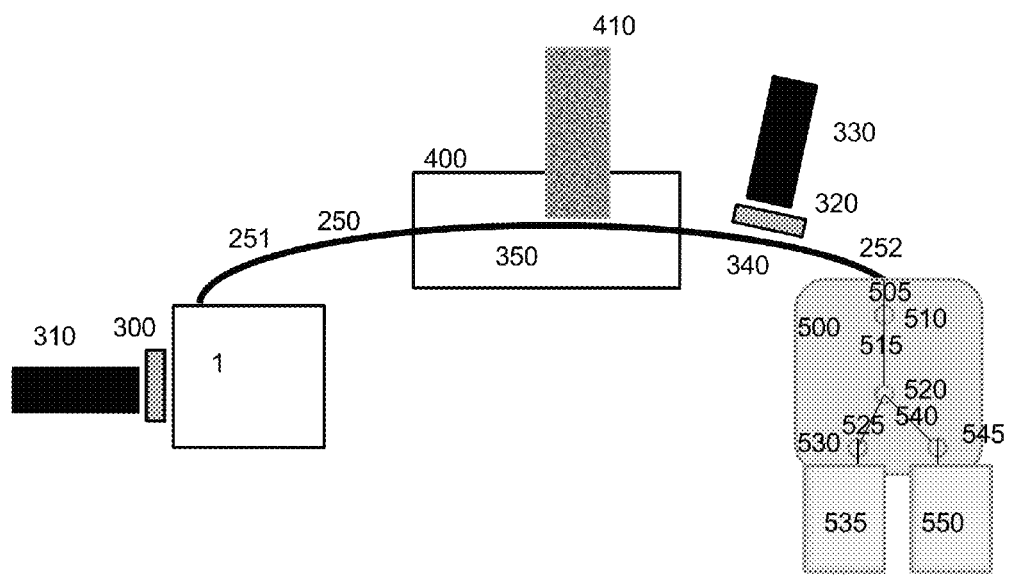
FIG. 6 shows a cartridge connected to reaction chamber and detector with downstream MOVe pumps and reagents.

In some embodiments of the invention, a cartridge can be integrated with devices for performing polymerase chain reaction and product analysis. Such a device is shown in FIG. 6. FIG. 6 shows a cartridge with integrated microchip (1), temperature modulating device (400), and downstream analysis device (500). In certain embodiments the device comprises a fluid preparation module comprising a cartridge mated or otherwise fluidically connected to a microchip; an off-chip thermal modulation module connected to the fluid preparation module through a fluid transporter with a fluidic channel, such as a tube, through the cartridge, and configured to modulate the temperature in the fluid transporter, wherein the fluid transporter is further fluidically connected to a second microchip with valves and fluidic channels that can selectively route fluid to one or more subsequent devices. This device can be used for thermal cycling or isothermal reactions.

The cartridge with integrated microchip can be formed of any cartridge and microchip described herein. For example, the cartridge and microchip shown in FIG. 3, FIG. 4, and FIG. 5. A movable magnet (300) can be positioned adjacent to the cartridge. The movable magnet can be moved by an actuator (310). The movable magnet can be used to apply a magnetic field within the cartridge or the microchip. In some embodiments, the movable magnet can be used to facilitate gathering or collecting of beads against a wall of a chamber within the cartridge or the microchip.

Figure 7:
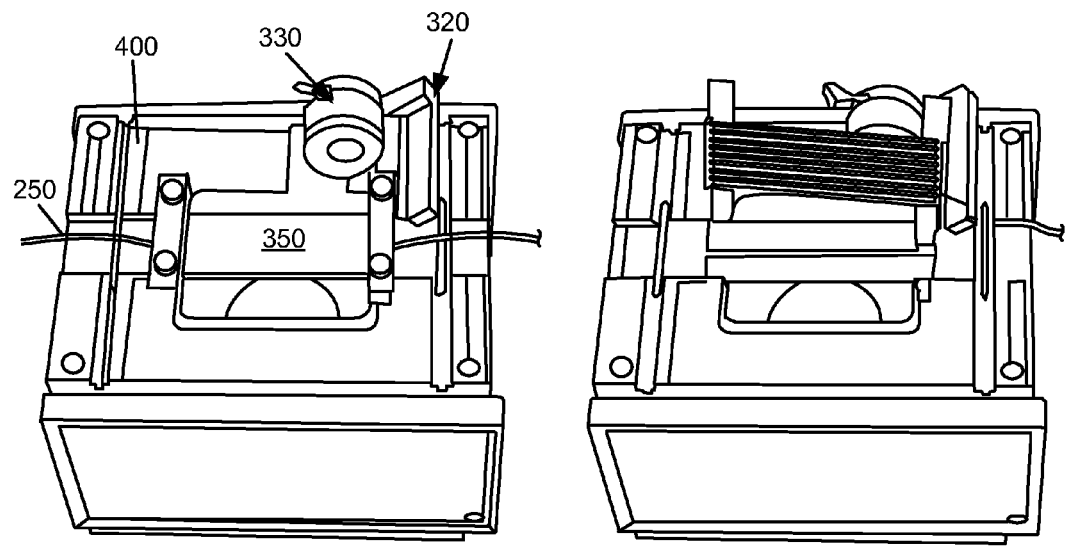
FIG. 7 shows a temperature control device that can thermal cycle and incorporates magnetic capture, pinch clamps and the capability of cycling seven reactions simultaneously.
Figure 8:
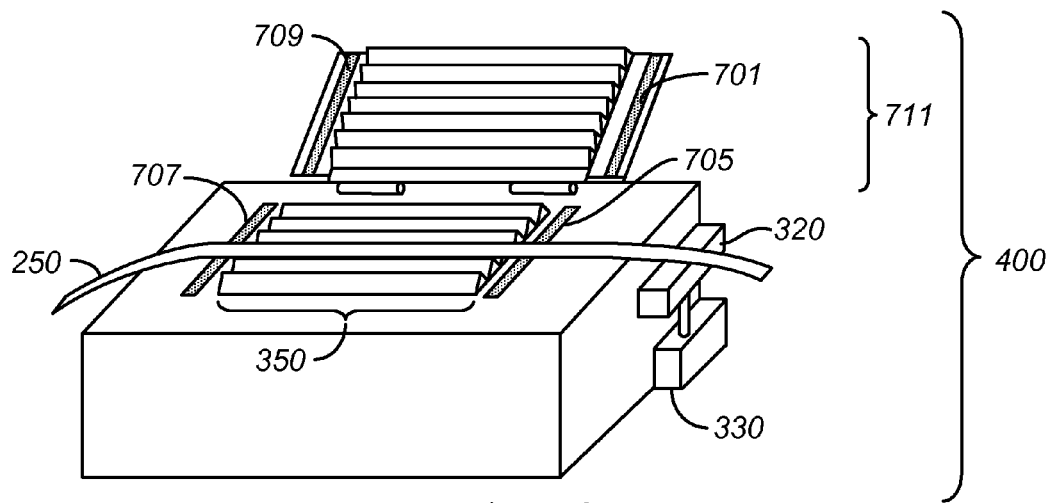
FIG. 8 shows a temperature control device that can thermal cycle and incorporates magnetic capture, pinch clamps and the capability of cycling seven reactions simultaneously.

A temperature modulator can be fluidically connected to the cartridge and microchip through reaction channel (250). The reaction chamber (250) can be connected at an end (251) to the cartridge. The temperature modulator can be used for thermal cycling the temperature of a reaction channel (250) containing a reaction mixture and a nucleic acid enriched from a sample (collectively referred to as the PCR reaction sample). A control mechanism can be used for controlling the operation of the temperature modulator. An optical assembly can be used to monitor or control the reaction. The optical assembly can introduce or detect light. For example, an optical assembly 410 can be used for performing Real-time PCR or other real-time or end point measurements. In certain embodiments the temperature modulator employs a thermocoupled Peltier thermoelectric module, a conventional thermoelectric module, hot air, infrared light or microwave. In one embodiment the temperature modulator uses a Peltier thermoelectric module external to the reaction channel to heat and cool the PCR reaction sample as desired. The heating and cooling of the thermoelectric module can be distributed over a region 350. Additional views of the temperature modulator 400 are shown in FIG. 7 and FIG. 8. FIG. 7 shows the reaction channel 250 in contact with a temperature controlled region 350. The temperature modulator can also include a movable magnet 320 that is positioned by an actuator 330. The movable magnet can be used to capture magnetic particles at position 340, as shown in FIG. 6. In some embodiments of the invention, the temperature controlled region comprises two parts. The two parts can be parts of a clamshell that are clamped, locked, or held together to maintain thermal contact with the reaction channel 250. One portion of the temperature controlled region, portion 711 of FIG. 8, can be hinged to the second portion of the temperature controlled region. The temperature controlled regions can have grooved channels for positioning of one or more reaction channels, as shown on the right side of FIG. 7 and in FIG. 8. The left side of FIG. 7 shows the temperature controlled region in a closed configuration. Additionally, the temperature controlled region can comprise one or more constriction components, shown as 709 and 701 in FIG. 8. The constricting points can pinch the reaction channel such that a portion of the reaction channel is isolated from another portion of the reaction channel. In some embodiments of the invention, the reaction channel is pinched in two locations such that a body of fluid, such as a reaction mixture, is isolated. Constriction components 709 and 701 can mate with additional constriction components 707 and 705 to facilitate pinching of the reaction channel.

Figure 65:
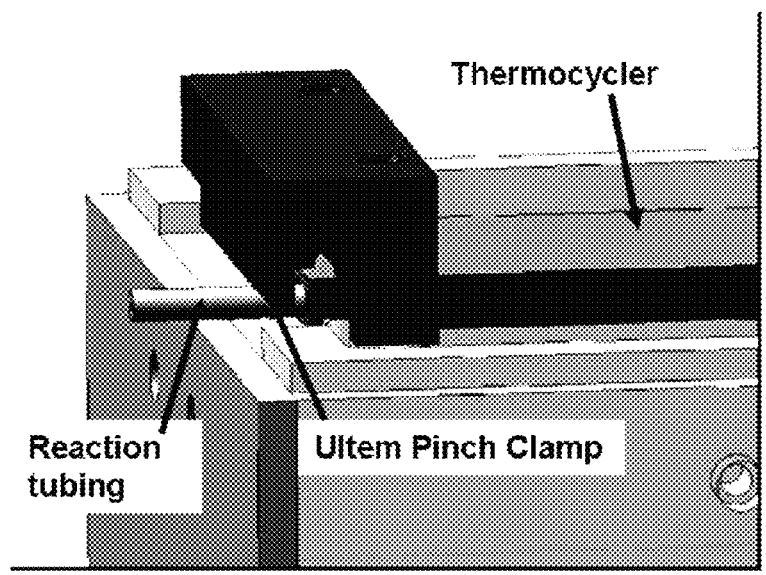
FIG. 65 shows a thermocycler with an Ultem pinch clamp.

Alternatively the temperature modulator can constrict the reaction tubing using an pinch clamp, as shown in FIG. 65. Use of the pinch clamp, which can be formed of a plastic such as Ultem, can reduce heat transfer to the reaction channel. The reduction in heat transfer can reduce the likelihood that the reaction channel has for being welded closed during thermocycling or temperature regulation. Alternatively, different material tubing can be used as the reaction channel to ensure that the reaction channel can maintains its shape before and after the thermocycling or temperature regulation process. Different material tubing can also be used to reduce rate of evaporation during the temperature modulating process. Example materials include ethylvinyl acetate, silicone, and silanized c-flex tubing.

The temperature modulating device can modulate temperatures at a rate of 0.5 to over 3 degrees Celsius per second. The heater can utilize about 25 to 100 Watts and a fan, which can be used to cool the temperature modulating device, can produce an air flow rate of at least about 75, 100, 130, 150, 200, 250, or 300 cfm.

In one embodiment a sample preparation device comprising a cartridge integrated with a microfluidic microchip 1, which can be used to control the movement of fluid in the cartridge, can be used in conjunction with a temperature modulator 400 as a flow-through PCR thermal cycler. Driving force for moving the fluid can be an external pressure source or an internal pressure source, such as a MOVe valves within the microchip. A flow-through PCR thermal cycler can be used when highly sensitive or high throughput PCR is desired. There are many situations in which one might want to sample air, blood, water, saliva, a cellular sample, or other medium in a sensitive PCR assay. This can be used to look for a variety of biological contaminants including influenza, bacterial pathogens, and any number of viral or bacterial pathogens. Flow-through PCR can allow PCR to be practiced in an automated manner without the need for human interaction. A flow-through PCR system can also serve as an early warning system in HVAC systems of buildings, airplanes, busses, and other vehicles, and can be used in the monitoring of blood, water, or other sample sources for the presence of an infectious agent or a contaminant.

As shown in FIG. 6, the flow-through PCR device takes a sample from a collection device, such as a buccal swab, a syringe, an air sampler, fluid sampler or other sampler and delivers it to a sample preparation device 1. FIG. 6 is not necessarily drawn to scale. The sample is prepared in the preparation device 1, which in some embodiments may include cell lysis, DNA, RNA, or micro RNA enrichment or purification, filtration, or reverse transcription. In one embodiment at least one nucleic acid is enriched. In another embodiment at least one enriched nucleic acid is prepared for PCR by adding the nucleic acid to PCR reagents (such as at least one DNA polymerase, RNA polymerase, dNTPs, buffer or a salt) and primers, (such as assay-specific primers or broadly applicable primer sets for multiple target pathogens). These primers may be chosen to selectively amplify at least one nucleic acid isolated from a specific pathogen (such as a mold, virus, bacteria, parasite or amoeba), gene, other desired nucleic acid, or any combination thereof. The composition comprising at least one nucleic acid enriched from a sample, PCR reagents and primers is called a PCR reaction sample. In one embodiment, the flowthrough PCR can be used as a continuous flow device while in other embodiments samples are moved into the thermal cycling region and stopped.

The PCR reaction sample then flows through a reaction channel (250) to a temperature controlled device or region (350). In some embodiments the reaction channel is clear or transparent. In another embodiment the reaction channel is opaque. In one embodiment the reaction channel is a cylinder. In another embodiment the reaction channel's cross section comprises one or more planes forming a shape such as a triangle, square, rectangle, pentagon, hexagon, heptagon, octagon, nonagon, decagon, or other polygon. In one embodiment the volume of PCR reaction sample is such that it takes up a small discrete length of space in the reaction channel, the rest of which is occupied by air, gas, or a non-reactive liquid, such as mineral oil. Air, gas, or a non-reactive liquid can be used to separate individual PCR reaction samples from each other. In one embodiment the temperature controlled region (350) is thermally modulated by one or more modules, including but not limited to thermo-coupled Peltier thermoelectric module, a conventional thermoelectric module, hot air, microwave, or infrared light. In one embodiment the thermal cycler uses Peltier thermoelectric modules external to the tube to heat and cool the sample as desired. In one embodiment a detection module (410) measures fluorescence, luminescence, absorbance or other optical properties to detect a signal emitted from a PCR reaction sample while it is located with a temperature control region, or after it has left a temperature control region. A detection module can comprise a light source (such as a coherent light source or incoherent light source) used to excite a fluorescent dye (such as an intercalating dye, including but not limited to ethidium bromide or Syber green) in a PCR reaction sample, and the excitation light is sensed with a photodetector (such as a CCD, CMOS, PMT, or other optical detector). Detection electronics can evaluate the signal sent from the detection module (410).

In one embodiment, after the desired number of thermal cycles are complete, the PCR reaction sample is pumped or pushed further down the reaction channel, using pressure or vacuum, exiting the temperature controlled region and passing into a second microfluidic microchip (500). The second microchip (500) can be attached at end (252) to the reaction channel (250). Microfluidic microchip (500) can comprise microvalves (510, 520, 530, and 545). Any three microvalves such as 510, 520, and 530 or 510, 520, and 545 can form a pump. Microchannels 505, 515, 525, and 540 can connect the pumps on the microchip. Downstream devices 535 and 550 can be connected to the microchip. Flow of material to devices (535 and 550) can be controlled by the microvalves, for example, by keeping either valve 530 or 545 closed while pumping or moving fluid. In one preferred embodiment, the downstream device are analytical devices that can be used for performing electrophoresis, mass spectroscopy, or other analytical techniques known to one skilled in the art.

In one embodiment the second microfluidic microchip can deliver the PCR reaction sample to a module or region for further processing or analysis. In another embodiment multiple reaction channels may be used in parallel to increase sample throughput. In yet another embodiment the system may alert the user when amplification has occurred (a positive result), indicating that the target sequence is present. In one embodiment a reaction channel is used for a single use only, then disposed of. In an alternative embodiment a reaction channels can be used to amplify and detect the presence or absence of PCR amplification products in multiple samples. More than one PCR reaction samples can be loaded at intervals and interspaced with a barrier bolus of gas or liquid to prevent intermixing. In one embodiment samples are spaced apart in a manner so that as one is undergoing thermal cycling another sample is in the detection region undergoing interrogation. It will be obvious to one skilled in the art that the PCR amplification can be replaced by other nucleic acid amplification technologies which may use thermal cycling or be isothermal reactions.

In other embodiments, the device can perform isothermal reactions such as sandwich assays using affinity reagents such as antibodies or aptamers to determine if cells, proteins, toxins, or other targets are present with the detection module (410) providing a reading of the amount of target present. In these applications, the cartridge 1 may perform an affinity purification such as an IMS purification and then add a secondary antibody that may have a fluorescent label attached. The sample can then move into region 350 where the thermal control is set to optimize the reaction. Detection module (410) can then monitor the reaction. In one embodiment, a plurality of cartridges are ganged to reaction channel (250) and a series of boluses can be readout with detector 410.

IV. Device for Capillary Electrophoresis

In one embodiment a complete sample-to-answer system is used, which can comprises microfluidics, requiring coupling all steps together to match volumes and concentrations. Sample analysis using capillary electrophoresis is a standard analytical method that can be used with microfluidic sample preparation methods as described above. Capillary electrophoresis is readily adaptable to microfluidic microchips. In the instant invention, capillary electrophoresis on microchips is combined with MOVe valves to provide control of samples, process beads to concentrate the samples, and improve the loading and separations.

Figure 30:
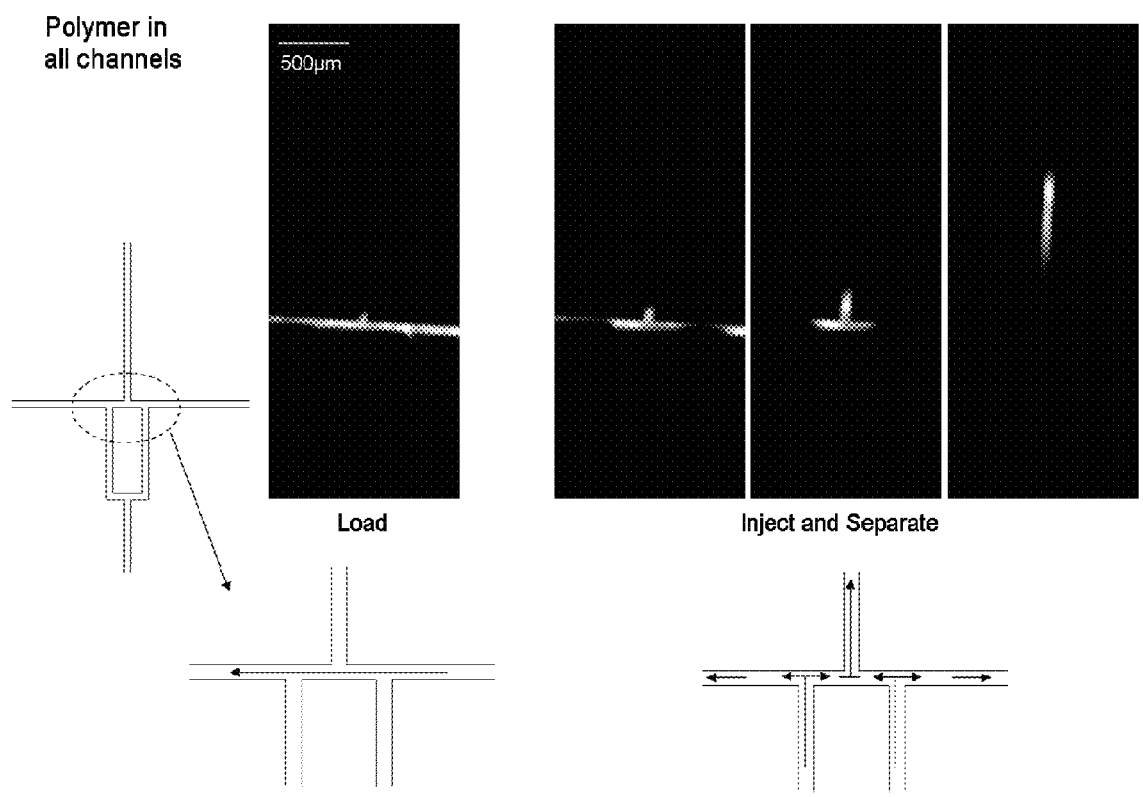
FIG. 30 shows a forked injector for microchip based electrophoresis.

In one embodiment the Twin-T injection system is used in the design of the microfluidic injector for separations. In an alternative embodiment a design is used for the Forked Cathode injector (FIG. 30). The layout is similar to the Twin-T in that the sample plug is described by a section of channel adjacent to the separation channel but key differences exist. First, the cathode channel is divided into two parts, this splits the injection electrically into two parts and thus doubles the quantity of material injected for a given sample plug dimension. Second, the sample channel and separation channel are at right angles to one another. This allows the sample channel to be straight and filled with buffer (rather than separation polymer), which facilitates manipulating the contents of this channel with pumps and fluid flows, and allows the separation polymer interface to be sharp. Lastly, the injector can be run in a mode that allows Field Amplified Sample Stacking (FASS).

FIG. 30 shows an example of a forked cathode injector that utilizes microchannels as the forked cathode. As shown in FIG. 30, a sample is moved electrokinetically across a sample loading channel (shown in the drawing on the lower left with the arrow through it). Then the sample is driven into the separation channel (the vertical channel) by applying a field between it and the cathode arms (the two channel dropping down) while pull back is applied to the sample and waste. The initial sample plug dimension is defined by the distance between the cathode arms. The configuration of the channels allows for a more reproducible plug and better integration with MOVe microfluidic systems.

In an aspect of the invention shown in FIG. 30, fluidic channel 3003 is in electrical contact with forked electrodes 3001 and 3002. The points of contact of the electrodes with the channel are spaced apart, thereby creating a segment in the channel in which there is an electric field. Separation channel 3004 intersects fluidic channel 3003 at a point in the segment between the points of contact of the forked electrodes. Another electrode of opposite charge is put in electrical contact with the separation channel. In this way, a voltage is applied through the separation channel.

Figure 62:
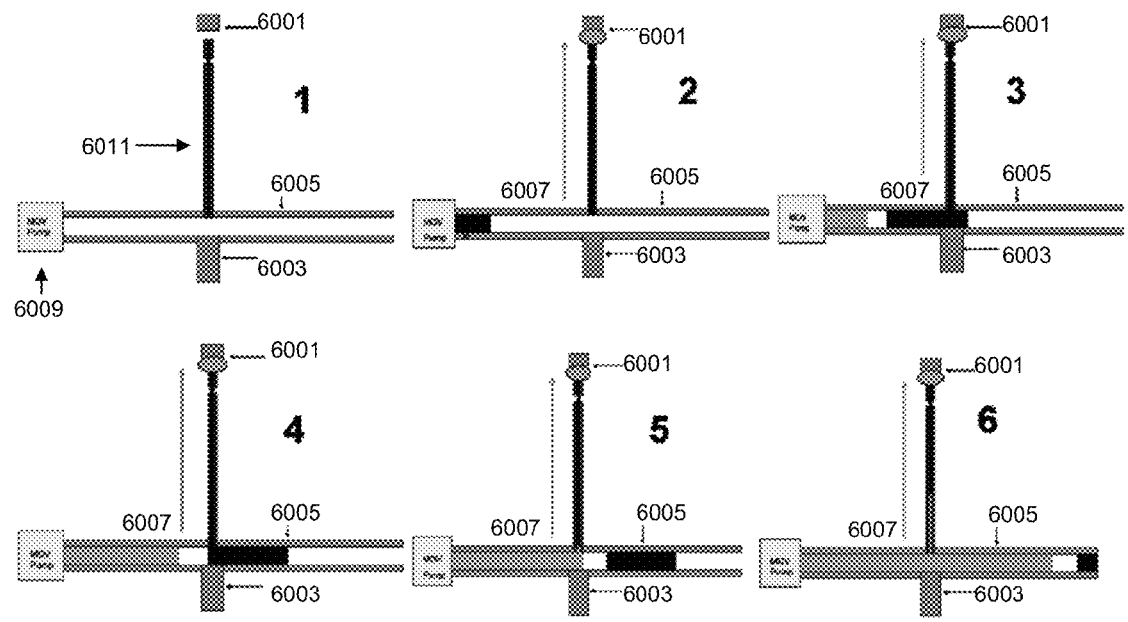
FIG. 62 shows sample injection into a separation channel.

FIG. 62 show a sample source 6009 connected to a sample channel 6005, also referred to as a loading channel, that is mated with a separation channel 6011. Two electrodes, 6003 and 6001, can be used to apply an electric field to the separation channel. In some embodiments of the invention, the sample source can pass through a MOVe pump in a microchip used to drive fluid flow within the sample channel. The sample channel can be a microfluidic channel or an injection tubing. The injection tubing can be flexible tubing or another flexible connector. Examples of flexible tubing include polytetrafluoroethylene tubing or silicon tubing. The flexible connector can also connect to another cartridge interfaced with a microchip. Alternatively, the flexible connector can return to the cartridge that it originated from. The separation channel can be a microfluidic channel, capillary tubing, or capillary electrophoresis tubing. The capillary tubing can have an outer diameter of about 150 to 500 microns and an inner diameter of about 10 to 100 microns. The capillary can be polyimide or polytetrafluoroethylene clad. The capillary can be about 2 to 100 cm long. The capillary can be mated to the injection tubing or flexible tubing by first drilling a hole into the injection tubing and then inserting the capillary into the flexible tubing. Alternatively, the capillary can be inserted into the flexible tubing without having to pre-drill the flexible tubing.

One of the two electrodes, for example electrode 6003, can be a cathode and the other electrode, for example 6001, can be an anode. The cathode can be any cathode, such as a forked cathode, described herein. The anode can be connected to the separation channel using any devices known to those skilled in the art. For example, the separation channel can be joined to a reservoir by an Upchurch fitting, which is in electrical contact with the anode, which can be a metallic electrode.

Figure 63:
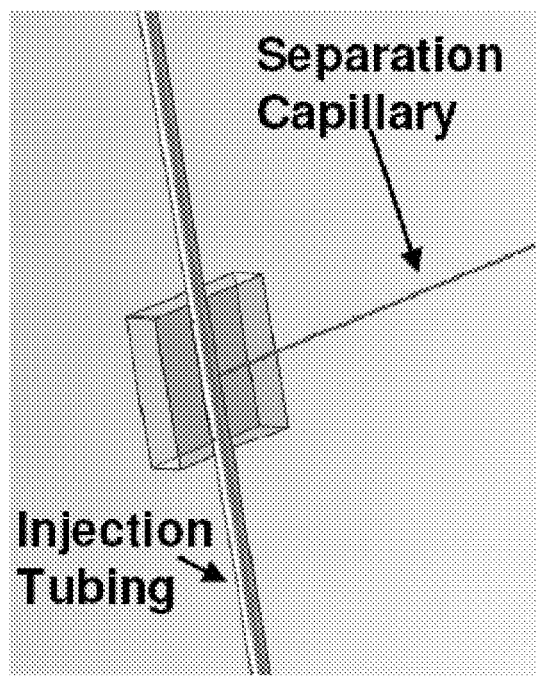
FIG. 63 shows a device for mating a separation capillary with an injection tubing.
Figure 64:
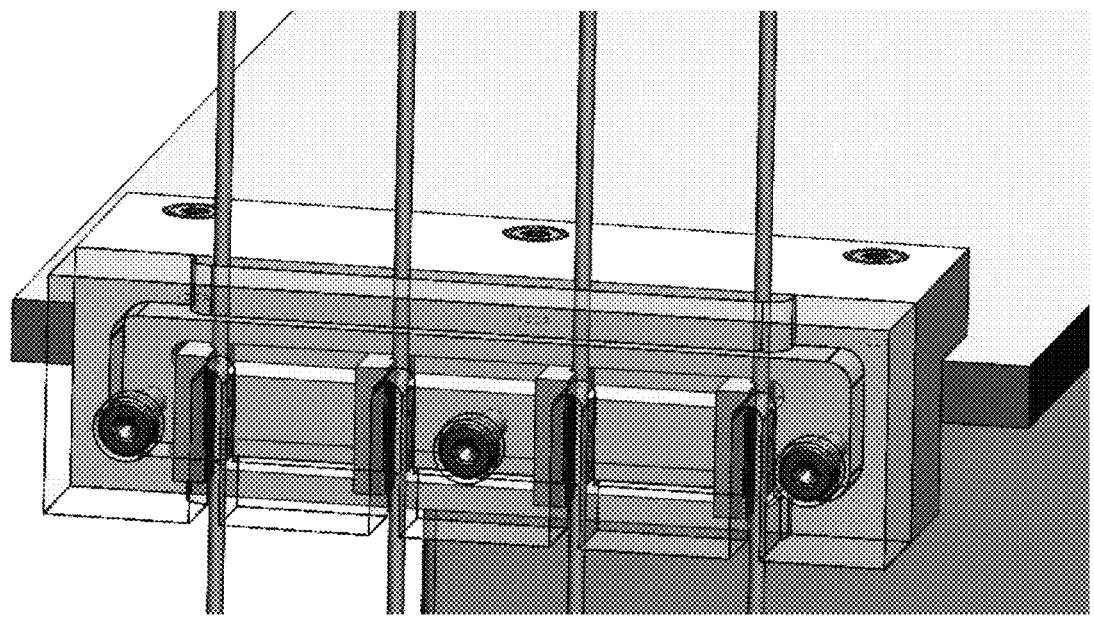
FIG. 64 shows a device for mating separation capillaries with four injection tubings.

In some embodiments of the invention, a stabilizing component, shown at the intersection of a separation capillary and injection tubing in FIG. 63, can be used to align, seal, and/or protect the connection between the separation capillary and the injection tubing. In some embodiments of the invention, multiple injection tubings are aligned with multiple separation capillaries using a stabilizing component. As shown in FIG. 64, the stabilizing component can hold four injection tubings, shown as the vertical tubings in the figure, and stabilize the connection with four separation capillaries (not shown).

Panels 1-6 of FIG. 62 show a process for injecting a sample into a separation channel. In panel 1, no sample is present in the sample channel 6005. In panel 2, sample entering the sample channel from the sample source (6009) is shown. As sample is moved down the sample channel, the sample intersects the separation capillary, as shown in panel 3. The sample can be isolated by boluses of gas upstream and downstream to the sample. Once sample is adjacent to the separation channel, an electric field, which can be between 25 and 500 V/cm, is applied between a first electrode 6003, which can be a cathode or a forked cathode, and a second electrode 6001, which can be an anode. Electrophoresis buffer, shown entering into the sample channel from the sample source, can also enter the sample channel, as shown in panel 3. The voltage potential and/or current between the anode and cathode can drop when an air bolus passes by the junction between the sample channel and the separation channel, reducing or preventing the injection of air into the separation channel. The voltage potential and/or current drop can be detected to ascertain when the sample and/or electrophoresis buffer is adjacent to the separation channel. Once the electrophoresis buffer is adjacent to the separation channel, as shown in panel 5, the current and/or voltage drop between the anode and cathode can be increased. This can allow for the separation of the analyte in the separation channel, as shown in panel 6, as the electrophoresis buffer provides ions for a high performance separation.

Figure 31:
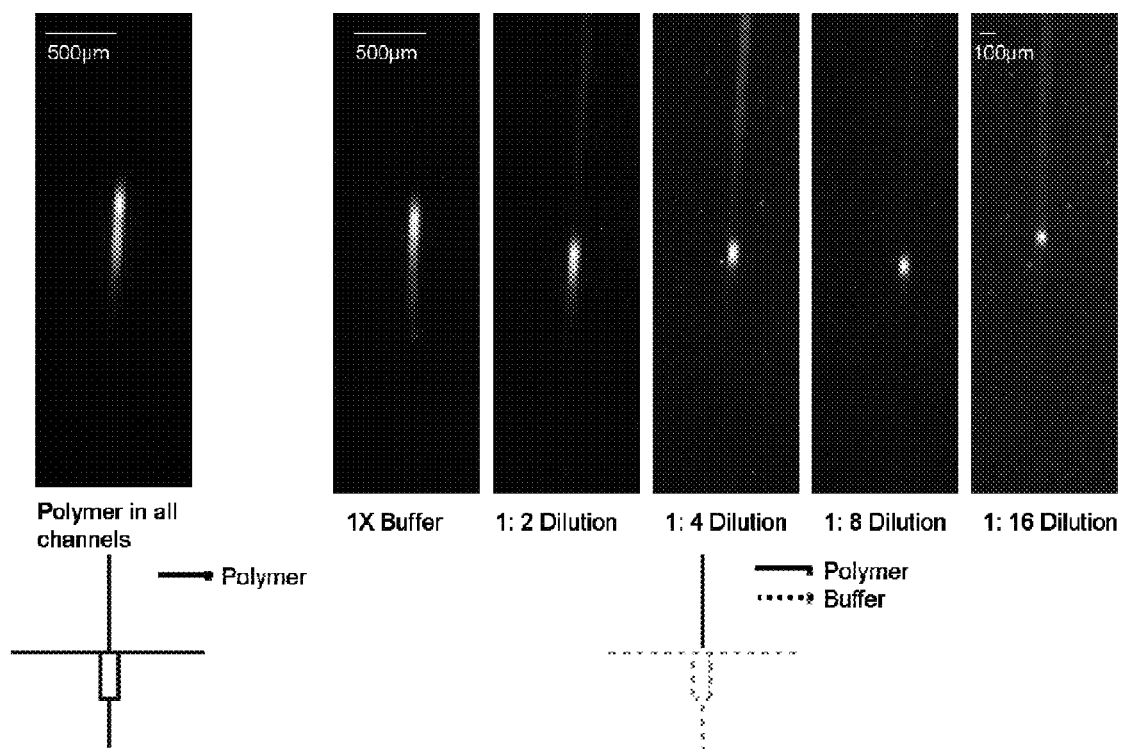
FIG. 31 shows sample stacking with a forked injector.

FASS is a chromatographic technique that uses the increase in the electric field caused by areas of low conductivity to increase analyte mobility in the sample area and concentrate the analyte at an interface of an area of lower mobility, i.e., at the separation matrix. The net effect of running the injector in this manner can be seen in FIG. 31. Significant decrease of the sample plug length, herein referred to as stacking, can be observed.

The injector is filled with buffer (dashed line) then the separation polymer is loaded (solid line) while the interface is swept. The sample channel (horizontal channel) is filled with sample reaction products in low ionic strength media. This allows sample stacking and significantly decreases the sample injection plug size. This is shown in the five frames on the right of FIG. 31 versus the all polymer injection in the left panel. The effect of ionic strength and stacking is seen in the images from second left to right as the buffer dilution increases and the ionic strength decreases. The sample plug narrows from approximately 300 microns to less than 100 microns.

In one embodiment for STR analysis the injection process is as follows:

The microfluidic channels can be filled with buffer.

The separation channel can be filled with gel while buffer is pulled across the sample channel, thus sweeping the separation polymer from the cross section formed by the separation and sample channels.

The STR amplified sample (desalted and captured on beads) can be captured on microchip 500, eluted in a low conductivity fluid (water) containing the size standard, and pumped into the sample channel with MOVe technology.

A field can be applied across the cathode and anode, with "pull back" voltage on the sample and waste arms, to drive the sample into the separation channel where it stacks at the head of the separation polymer.

As the sample is injected the conductivity of the sample channel can quickly equilibrate with the buffer in the cathode arms providing a single step injection.

The MOVe controlled Forked Cathode injector design (FIG. 32) can be optimized for DNA separations in microchip channels. In addition to the FASS described above, the unique integrated injector design also incorporates the MOVe pumping system which facilitates the use of magnetic bead technology to desalt and concentrate samples.

Figure 33:
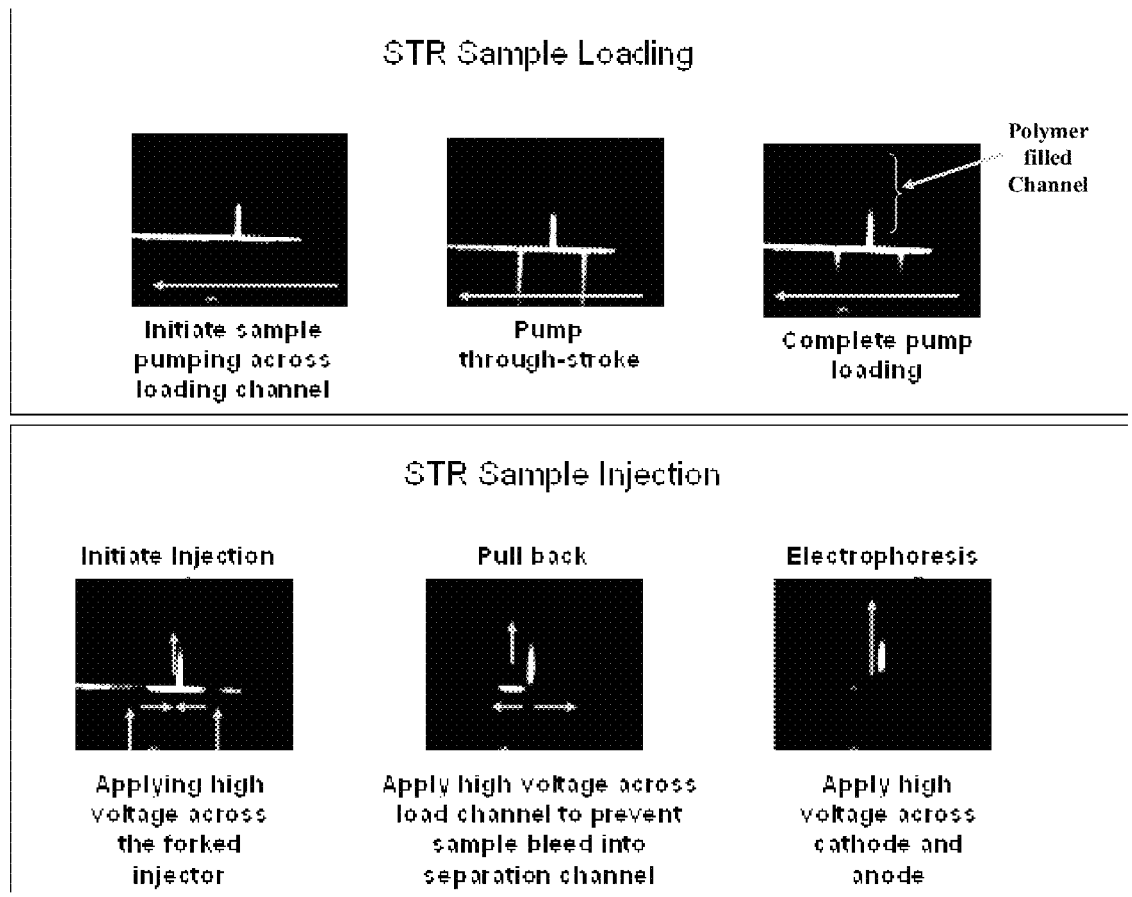
FIG. 33 shows a forked cathode injector coupled with a MOVe microchip.

Purified STR amplification products are eluted from magnetic beads, heat denatured and pumped through the loading channel of the Forked Cathode injector. A voltage regime is applied to facilitate an FASS injection at the head of the polymer column, and DNA separation is performed in a polymer filled micro-channel (FIG. 33). In FIG. 33, the photos show the movement of dye in the injector in order to illustrate the STR sample injection mechanism. Field amplified stacking occurs at the polymer head when injection is initiated.

Figure 60:
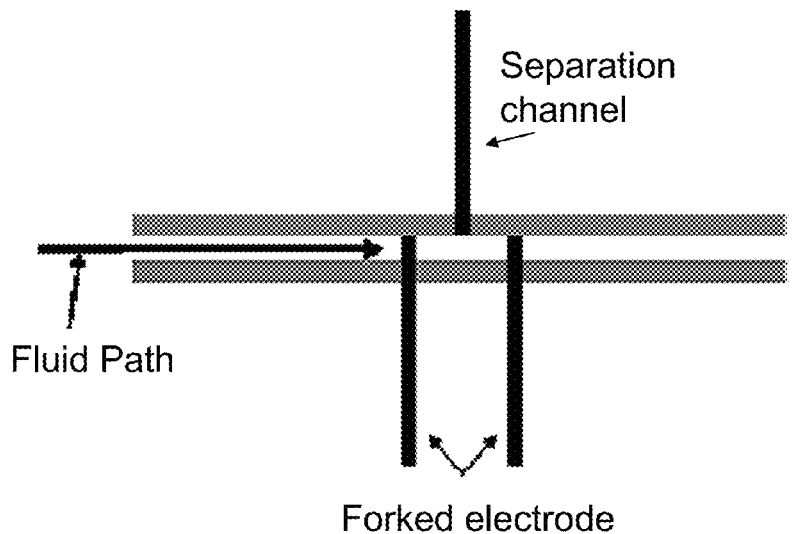
FIG. 60 shows a forked electrode.

Alternatively, the forked electrode or cathode can be two metallic conductors, as shown in FIG. 60. The fluid path for a sample to be analyzed, as shown in FIG. 60, can be along a loading channel. When the location of the sample is adjacent to the separation channel, the forked electrode can be used to inject the sample into the separation channel, as described herein. The conductance of the material in the sample channel can be lower than the conductance of the material in the separation channel, which can be a separation polymer. The difference in conductance can cause sample stacking when an electric field is applied through the forked electrode, which can be a cathode, and a downstream electrode, which can be an anode. The polarity of the forked electrode and the downstream electrode can be reversed such that the forked cathode is the anode and the downstream electrode is the cathode.

Figure 61:
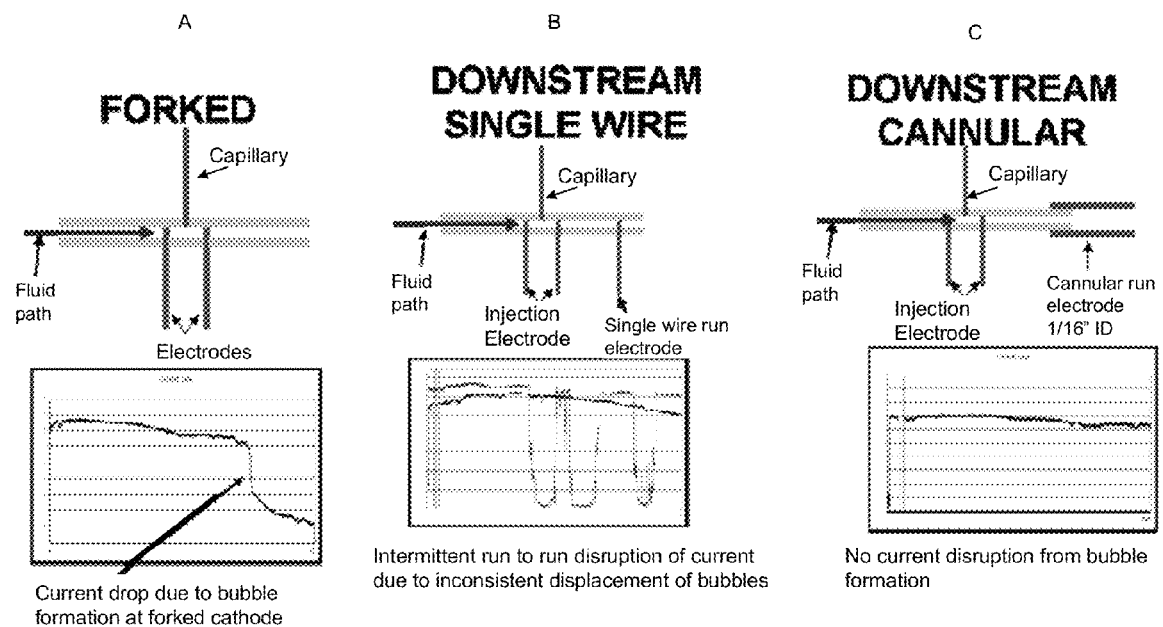
FIG. 61 shows a forked electrode, a forked electrode with a wire run electrode, and a forked electrode with a cannular electrode.

In some embodiments of the invention, an additional electrode can be used to reduce injection of gas into the separation channel or formation of bubbles within the sample loading channel which can lead to loss of the applied field on the separation channel. Injection of gas into the separation channel or formation of bubbles within the sample loading channel can cause inconsistent separation of analytes and can be detected by inconsistent current between the anode and cathode used to apply an electric field to the separation channel. Use of an additional electrode to circumvent or reduce injection of gas or bubbles into the separation channel is shown in FIG. 61. The additional electrode can be a single wire run electrode or a cannular run electrode. The increased surface area and/or larger internal diameter of the cannular run electrode can allow for a significant reduction in bubble formation or blockage and/or injection into the separation channel. In some embodiments of the invention, the cannula used for the cannular run electrode and has an inner diameter of at least about 1/64, 1/32, 1/16, 1/8, or 1/4 inches.

V. mRNA Amplification

The devices of the invention can be utilized for microarray sample preparation processes. Gene expression microarrays monitor cellular messenger RNA (mRNA) levels. However, mRNA can constitute only 1-3% of cellular total RNA. The vast majority of cellular RNA is ribosomal RNA (rRNA), and these molecules may interfere with mRNA analysis by competing with mRNA for hybridization to microarray probes. Any mRNA amplification method can be performed by the devices described herein, for example LAMP, TLAD (Eberwine), and MDA. In some embodiments of the invention, isothermal mRNA amplification methods can be performed using the devices described herein. In other embodiments, thermal cycling can be performed to accomplish PCR or cycle sequencing.

The Eberwine mRNA amplification procedure specifically targets polyadenylated mRNA (polyA+mRNA) for amplification, virtually eliminating rRNA interference. This characteristic removes any need to pre-purify mRNA from total RNA, which can be an inefficient, time-consuming, and expensive process. In addition, by greatly increasing the amount of target RNA (that is, amplified mRNA or aRNA) available for microarray hybridization, mRNA amplification can allow much smaller samples (fewer numbers of cells) to be analyzed. This can be helpful because the relatively large amount of target RNA required for microarray analysis (typically 15 ug) is frequently difficult to obtain. Moreover, it can be essential in many important clinical diagnostic applications analyzing samples containing few cells, for example, samples derived from fine needle aspirates (FNA) or laser capture microdissection (LCM).

Any process that alters relative mRNA abundance levels may potentially interfere with accurate gene expression profiling. An important aspect of the Eberwine amplification procedure is that it employs a linear amplification reaction that can be less prone to bias mRNA populations than exponential amplification methods such as PCR.

Figure 44:
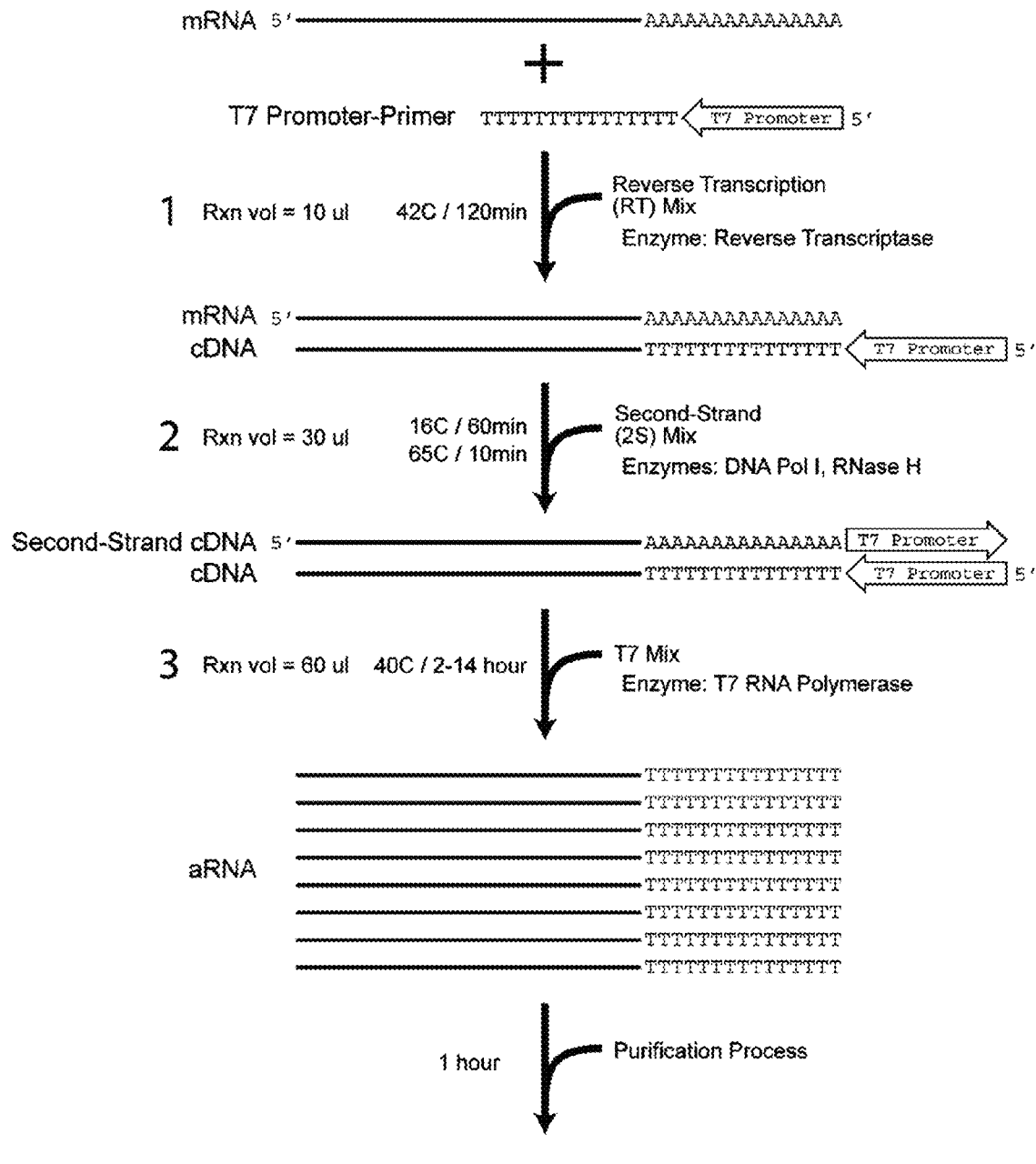
FIG. 44 depicts a reaction scheme for amplifying mRNA.

The original Eberwine protocol has been streamlined and simplified by commercial vendors such as Ambion. As shown in FIG. 44, the Ambion procedure comprises three binary (two component) additions followed by an RNA purification process. Each binary addition can be followed by incubation(s) at specific temperatures, as indicated in FIG. 44. The initial reverse transcription (RT) reaction can have three inputs (primer, total RNA, and reverse transcriptase [RT] Mix); however, total RNA and primer can conveniently be premixed. Typical volumes for this first reaction can be 5 ul RNA+Primer 5 ul RT Mix. Only mRNA hybridizes to the oligo dT primer and is transcribed into DNA. The second-strand reaction can be initiated by addition of 20 ul of a Second-Strand Mix, and the final T7 amplification reaction can be initiated by addition of 30 ul of a T7 Mix. Synthesized RNA can be labeled at this stage by incorporation of biotin-labeled ribonucleotides. Mixes contain buffers (Tris), monovalent and divalent salts (KCl, NaCl, $MgCl_2$), nucleotides, and DTT, along with enzymes as indicated. Typically, enzymes can be premixed with concentrated mixes just prior to use.

After synthesis, aRNA can be purified to remove enzymes, buffers, salts, unincorporated nucleotides, pyrophosphate, etc. Purification typically relies on commercial kits exploiting the association of aRNA with silica membranes or beads in the presence of chaotropic salts such as guanidinium hydrochloride (GuHCl) or thiocyanate (GuSCN). After binding, the silica is washed with 70% ethanol (EtOH), dried, and aRNA is eluted with water.

Each of these steps can be carried out on the devices described herein (See U.S. Provisional Patent Application No. 61/140,602). For example, reagents and sample can be supplied through ports in the cartridge and then delivered to the microfluidic microchip. The on-chip valves can be used to pump the reagents and samples to chambers and reservoirs in the cartridge and the microfluidic microchip through channels. Temperature control can be accomplished using internal or external heating and cooling devices. The reaction products can be moved to product outlet ports of the cartridge for further handling. Alternatively, the reaction products can be purified or separated using the devices of the invention.

VI. Separation and Cleanup

A variety of separations can be performed using the devices described herein. These separations include chromatographic, affinity, electrostatic, hydrophobic, ion-exchange, magnetic, drag-based, and density-based separations. In some embodiments of the invention, affinity or ion-exchange interactions are utilized to bind materials to solid-phase materials, such as beads. The beads can be separated from fluid solutions using any method known to those skilled in the art.

Magnetic separation can be used to capture and concentrate materials in a single step using a mechanistically simplified format that employs paramagnetic beads and a magnetic field. The beads can be used to capture, concentrate, and then purify specific target antigens, proteins, carbohydrates, toxins, nucleic acids, cells, viruses, and spores. The beads can have a specific affinity reagent, typically an antibody, aptamer, or DNA that binds to a target. Alternatively electrostatic or ion-pairing or salt-bridge interactions can bind to a target. The beads can be paramagnetic beads that are only magnetic in the presence of an external magnetic field. Alternatively, the beads can contain permanent magnets. The beads can be added to complex samples such as aerosols, liquids, bodily fluids, extracts, or food. After (or before) binding of a target material, such as DNA, the bead can be captured by application of a magnetic field. Unbound or loosely bound material is removed by washing with compatible buffers, which purifies the target from other, unwanted materials in the original sample. Beads can be small (nm to um) and can bind high amounts of target. When the beads are concentrated by magnetic force they can form bead beds of just nL-μL volumes, thus concentrating the target at the same time it is purified. The purified and concentrated targets can be conveniently transported, denatured, lysed or analyzed while on-bead, or eluted off the bead for further sample preparation, or analysis.

Separations are widely used for many applications including the detection of microorganisms in food, bodily fluids, and other matrices. Paramagnetic beads can be mixed and manipulated easily, and are adaptable to microscale and microfluidic applications. This technology provides an excellent solution to the macroscale-to-microscale interface: beads can purify samples at the macroscale and then concentrate to the nanoscale (100's of nL) for introduction into microfluidic or nanofluidic platforms. Magnetic separations can be used as an upstream purification step before real-time PCR, electrochemiluminescence, magnetic force discrimination, magnetophoretic, capillary electrophoresis, field-flow separations, or other separation methods well known to one skilled in the art.

The devices of the invention can accommodate the use of magnetic beads. For example, beads or bead slurry can be supplied to a port of a cartridge. The beads can be mixed or suspended in solution within the cartridge using pumping, magnetic fields, or external mixers. The beads can then be pumped to desired chambers or reservoirs within the microfluidic device of cartridge. Beads can be captured within a chamber using a magnetic field. Beads in a solution can be captured as the solution travels through the magnetic field, or beads can be captured in a stagnant solution.

To illustrate methods of use of the cartridge, several examples are described below. The first example describes processing of nucleic acid from a buccal swab with paramagnetic beads to purify the sample followed by PCR amplification and bead purification of the PCR products. A second example describes performing immunomagnetic separations to purify cells, proteins, or other antigenic material using a binding moiety coupled to beads. A third example describes performing molecular biology to prepare samples for sequencing technologies such as sequencing by synthesis, sequencing by hybridization, or sequencing by ligation. It would be known to one skilled in the art that many different chemistries and biochemistries can be used with the instant invention. These include, but are not limited to, enzymatic reactions, purifications on gels, monoliths, beads, packed beds, surface reactions, molecular biology, and other chemical and biochemical reactions.

EXAMPLES

Example 1

Operation of a Cartridge for Nucleic Acid Purification

This example refers to the use of a device comprising a cartridge mated to a microchip. The numbers refer to the cartridge of FIG. 3 and FIG. 4 mated to a microchip with the circuit architecture of FIG. 5. This sub-assembly also can be fluidically connected other sub-assemblies in the instrument of FIG. 6. For reference, a cartridge mated with a microchip also is shown in FIG. 40 and FIG. 59.

Nucleic acids can be purified from a wide variety of matrices for many purposes including, but not limited to, genotyping, identification, forensics, gene expression, gene modification, microRNA analysis, ribotyping, diagnostics, or therapeutics. The input sample can be a solid, swab, liquid, slurry, aerosol or a gas.

For molecular diagnostics and forensics, swabs are commonly used. A buccal swab can be taken using a swab with an ejectable tip and the swab ejected into a syringe attached to connection 7 of FIG. 4. Connection 5 of FIG. 4 leads by tubing or capillary to a reagent manifold that can select a single reagent from multiple reagents by opening a full scale valve or by opening a MOVe valve with the reagents either under pressure or moved by vacuum. MOVe or other micropumps on microchip 2 of FIG. 4 can also move the fluids or gases.

In one embodiment, human and other cells in a swab are first lysed using a buffer with a heated chaotrophic agent and/or other commercial-off-the shelf (COTS) chemistries in a syringe inserted into port 7. The lysate is transported to a DNA isolation chamber (FIG. 4 #3) where paramagnetic beads have been added from a reservoir to adsorb nucleic acids onto the beads. A moveable magnet is then actuated to capture the beads onto the side of the isolation chamber where they are washed automatically using a buffer. The purified DNA, still bound to beads, is then pumped through a small diameter tube 250 where multiplexed PCR is performed. Pre-scripted DevLink™ software automates the complete process. The DevLink software defines a set of communication and command protocols in a standardized automation architecture that is simpler, more flexible, and quicker to implement than other software development approaches. The DevLink implementation framework is based on core technologies that span multiple operating systems, development languages, and communication protocols. Software drivers wrap individual smart components of the system, greatly reducing the time needed for typical de novo system software development. This makes it relatively straightforward to integrate the operation of multiple system modules (pumps, valves, temperature controllers, I/O controllers, etc.) that are either COM- or .NET-based. DevLink provides a professional quality software development system for prototyping through product release and maintenance.

While DNA amplification is useful for positive identification of microorganisms, samples can be obtained from a wide variety of substrates and matrices that contain compounds that are inhibitory to DNA amplification reactions. Raw samples are most often complex mixtures that can include inhibitors such as hemes, metal ions, humic and fulvic acids, chelators, DNases, proteases, and molds. While the initial isolation of target organisms and toxins from the sample matrix by IMS should remove most of these inhibitors, lysed cell components and lysis agents can also need to be removed or diluted from nucleic acid samples so that they do not interfere with successful amplification.

In one embodiment, a small volume nucleic acid purification is used. These purification methods can be used with a wide range of samples, such as blood, to aerosols, to buccal swabs. Paramagnetic beads can be used in a disclosed device to purify DNA from various sample sources. In one embodiment a microfluidic microchip can be used to sequence a nucleic acid using magnetic beads and reagents to purify nucleic acid products for sequencing in microscale reactions. In one embodiment, the microfluidic microchip is a 24-channel microfluidic microchip.

In one embodiment, polyethylene glycol (PEG)-based nucleic acid purification is used on carboxylated magnetic beads. This PEG-facilitated process can produce yields of over 80% from upstream immunomagnetic separations (IMS) captured samples. Development of a universal sample preparation module (USPM) can partly involve porting the PEG-based nucleic acid purification onto a device containing a cartridge such as the devices shown in FIG. 21 or FIG. 16. In another embodiment, Agencourt Orapure or Promega DNA IQ chemistries are used in conjunction with a device of the present invention.

Bead Dispensation and Delivery.

To purify nucleic acids, paramagnetic beads with different surface chemistries can be mixed in a reagent container. Pressure is then applied to send the reagents to connection 5. MOVe microvalves or other valves may be closed unless referred to as open. To move the paramagnetic beads into the reaction chamber (3), microvalves 180 and 150 are opened. The beads are moved through connection 5 into channel 15 which leads to junction 190 and microchannel 191. Because microvalves 180 and 150 are open and microvalves 200 and 170, and the other microvalves, are closed, an open microfluidic connection is from microchannel 191 through microvalve 180 to microchannel 181 through microchip 152 to open microvalve 150 and microchip 151 to junction 120. Junction 120 leads to cone 13 and chamber 3, which can be filled with beads. The volume of beads supplied to chamber 3 can be controlled by timing the opening of the reagent valves and the microvalves or by filling and emptying a sample loop connected to the microchip or the cartridge.

Commercial bead based chemistries can be used in the disclosed system, including but not limited to Orapure from Agencourt (Waltham Mass.) and DNA IQ from Promega (Madison, Wis.). Orapure uses a carboxylated bead surface and SPRI chemistry while DNA IQ is an example of a silica bead and chaotrophic chemistry. Other embodiments of paramagnetic beads or chemistries to process nucleic acids can be used in conjunction with the disclosed system, including but not limited to beads with oligonucleotides, locked nucleic acids, degenerate bases, synthetic bases, conformation, nucleic acid structures, or other hybridization and specific capture methods.

Filling Chamber (3) with Beads.

For Orapure or DNA IQ beads, 450 microliters can be moved into chamber (3) using three fills of a 150 microliter sample loop 630 or 631. A movable magnet 300 attached to actuator 310 can then be moved towards cartridge (1) near the side of 3 to pull the beads to the side of chamber (3). Magnet size and orientation can be adjusted to generate magnetic fields appropriate to specific applications. Pressurized air can then be applied through the reagent manifold with microvalve 180, 150, and 110 open. The opening of microvalve 110 connects from junction 190 which connects to the reagent manifold through junction 120 and microchannels 121 and 101 to connection 100 which leads through channel 14 to connection (4) and to waste. The air can move any remaining liquid through the circuit. Air or other gases can also be used to dry beads, volatilize solvents, or for bubble-enabled mixing (described herein).

Bubbling of Gas through Chamber (3).

If microvalves 180, 150, and 220 are open, and all other microvalves closed, the pressure can force air through chamber (3) to channel 9 and down channel 19 to junction 210 through microchannels 211 and 221, through open microvalve 220 and microchannel 231 to junction 230, through channel 16 to connection 6 which can be a vent. This sequence can bubble air or other gases through chamber (3) and can be used to mix reactions in chamber (3) or to change the gas phase.

Moving Liquids and Beads from Chamber (3) to Waste.

Liquids and beads can be moved from reaction chamber (3) or any other location to waste. This can be used to wash beads, flush channels, move liquids or beads to waste. When pressure is applied to connection 6 with microvalves 220 and 110 open, and all other microvalves closed, the pressure can force air through channel 16 to junction 230 to microchannel 23$i$, through open microvalve 220 and microchannels 222 and 221, though junction 210, and channels 19 and 9 into reaction chamber (3) and through junction 120 through microchannel 121, open microvalve 110, microchannel 101, channel 14 and to connection 4.

The equivalent effect can be obtained by applying vacuum to connection (4) if connection 6 is a vent without any additional control of air pressure. The air pressure or vacuum can move any liquids in chamber (3) to the waste connection 4. When magnet 300 is close to chamber (3), paramagnetic beads can remain on the side of chamber (3) and the result is that the liquid is removed. When magnet 300 is far enough from chamber (3), paramagnetic beads can not remain on the side of chamber (3) and the result is that the liquid and beads are removed.

To clean paramagnetic beads, the beads are pulled to the side of chamber (3) with magnet 300 (see FIG. 6) and the liquid removed to waste. 450 microliters of buffer can be dispensed from the reagent manifold and added to chamber (3) by opening microvalves 180 and 150. The beads can be released if desired and then recaptured by moving the magnet 300 and the liquid then removed. This is repeated for a total of three times to produce beads ready to process samples.

Lysis and Extraction of Nucleic Acids from Cells on the Swab.

A swab can be loaded into a syringe barrel inserted into connection 7 and then be lysed by addition of lysis buffer through reagent connection 5 with microvalves 180 and 170 opened. In some embodiments Orapure or DNA IQ chemistries are used.

Movement of the Lysed Cellular Material to Chamber (3) and Mixing with Beads.

The material in the syringe connected to connection 7 can be moved into chamber (3) by applying pressure to the syringe or by applying vacuum to vent 6. When vacuum is used, microvalves 170, 150, and 220 are opened. The vacuum connects through microchannels 231, 221, 211, and channels 9 and 19 through chamber (3), microchannels 151, 152, 171, and 161 to pull material from connection 7 into chamber (3). When paramagnetic beads are loaded and cleaned in chamber (3), the lysed sample material mixes with the beads in chamber (3) with the magnet is the far position.

Purification of Nucleic acids on the Beads.

The paramagnetic beads are then incubated with the lysed sample. Continued air or gas flow can aid mixing. The magnet 300 is then moved to the closed position and the beads are captured on the wall of chamber (3). The sample lysate can then be removed from chamber (3) to waste and multiple volumes of wash solution added according to manufacturers' specifications for the Orapure chemistry or DNA IQ chemistry. The sample components on the beads have now been purified and are ready for reactions in the cartridge or exporting to the sample product connection. In one embodiment the beads are used to enrich a nucleic acid component from a sample.

Exporting Samples through the Sample Product Connection 8.

The purified sample components on the beads can be moved to connection 8 by applying pressures on reagent connection 5 with microvalves 180, 150, and 130 open. In one embodiment, connection 8 is connected with reaction channel 250 such as C-flex tubing (Cole Parmer) and additional reactions are performed in the reaction channel.

Multiplexed PCR Amplification of STR Markers.

DNA amplification can be performed by PCR amplification. The present invention enables PCR reactions as well as many other DNA amplification and modification reactions. The reactions can be performed in chamber (3), in reaction channel 250 attached to connection 8 which can be a tube 250 (FIG. 3, FIG. 4, FIG. 6), or in another device or microdevice connected to tube 250. This demonstrates the utility of the sample preparation for DNA reactions including thermal cycling.

Capture of Nucleic Acid Containing Beads in a Reaction Channel.

The purified DNA output through the sample product connection 8 is moved into a reaction channel 250 at end 251 by applied pressure or alternatively through vacuum applied to end 252. An actuator 330 moves a magnet 320 under software control into a position close to bead capture region 340. Fixed magnets of different sizes and shapes (such as rare earth magnets) as well as electromagnets or superconducting magnets can be used. As the solution containing the beads moves through region 340, the magnetic field attracts the beads to the side of the reaction channel and holds them in place. The fluid is then followed by air pressure through reagent connection 5 leaving the beads region 340 in air.

Addition of Reagents and Movement of Samples into Reaction Region.

Reagents can be added from the reagent manifold as described. In one embodiment, reagents are added from end 252 of reaction channel 250. End 252 is attached to a microfluidic microchip 500 comprising microvalves 510, 520, 530, and 540. Any three microvalves such as 510, 520, and 530 or 510, 520, and 540 can form a pump. Microvalve 530 connects through a microchannel to a downstream device 535, which can connect to tubing leading to a reagent reservoir. Microvalve 540 connects through a microchannel to downstream device 545, which can connect to tubing that leads to a reagent reservoir.

Reaction mixes (such as at least one DNA polymerase, dNTPs, buffer and a salt) including but not limited to master mixes and primers, (such as assay-specific primers or broadly applicable primer sets for multiple target pathogens), or complete PCR master mixes such as PowerPlex 16 from Promega (Madison, Wis.) or IdentiFiler or MiniFiler from Applied Biosystems (Foster City, Calif.) in reagent reservoir 600 can be delivered by a micropump formed by microvalves 530, 520, and 510 through tubing 610 and microchannels 531, 521, 511, and 512, into end 252 of reaction channel 250, as shown in FIG. 6. MOVe microvalves can precisely position fluids and move the fluid to region 340 where the reaction mix encounters the beads comprising nucleic acids. Magnet 320 is moved away from reaction channel 250 by actuator 330 which releases the beads from the inner surface of the reaction channel 250. The MOVe microvalves on microchip 500 pump the beads into device 400 with an area of reaction channel 250 forming temperature controlled region 350. The region 350 can be held at isothermal temperatures or thermal cycled or other varied as is well known to one skilled in the art. The region 350 can be a temperature modulator or thermally coupled to a temperature modulator.

FIG. 7 shows a temperature control device 400 that is capable of thermal modulation using a temperature modulator for heating and cooling to thermocycle the reaction channel. In one embodiment the temperature modulator comprises a Peltier module, infra-red module, microwave module, a hot air module or a light module. In another embodiment a PCR reaction sample is moved inside the reaction channel past one or more constant temperature zones.

Figure 9:
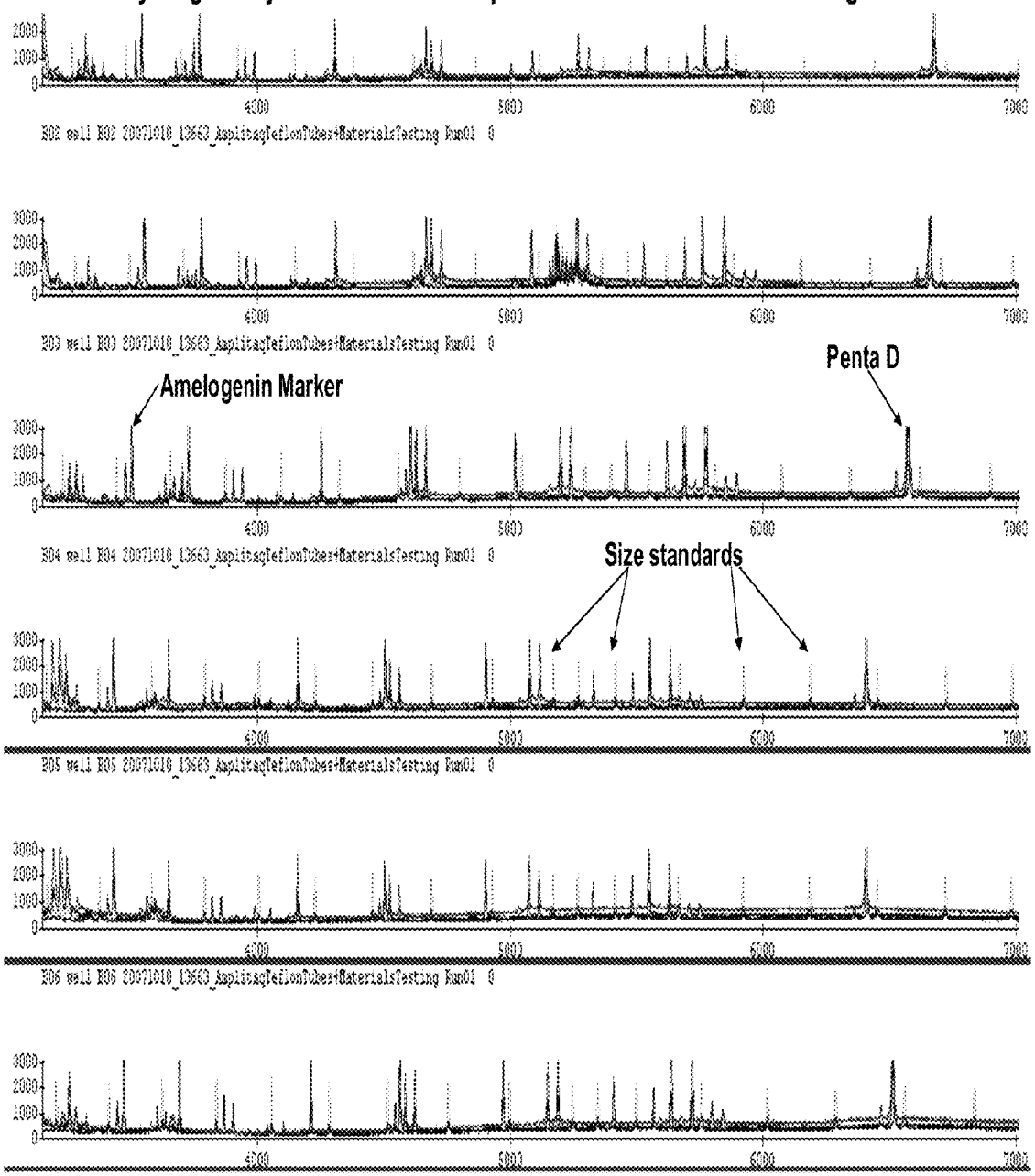
FIG. 9 shows PowerPlex16 STR (Single tandem repeat) amplification reaction performed in a passive, Teflon (PTFE) based Tube reaction chamber.

FIG. 9 shows the amplification of PowerPlex 16 STR reactions that have been prepared in a cartridge (1) from buccal swab samples and processed in reaction channel 250 using the temperature control device 400 in FIG. 7. The STR markers are amplified from standard conditions with Mg optimized for the apparatus 1000.

The temperature control device 400 can also have a detector 410. The detector can detect optical detection such as absorbance, fluorescence, chemiluminescence, imaging, and other modalities well known to one skilled in the art or measurement such as IR, NMR, or Raman spectroscopy. The detector can comprise a light source is used to excite a fluorescent or luminescent dye in the PCR reaction sample, and the excitation light is sensed with a photodetector (such as a CCD, CMOS, PMT, or other optical detector). In one embodiment the light source is a coherent light source, such as a laser or a laser diode. In another embodiment the light source is not a coherent light source, such as a light emitting diode (LED) or a halogen light source or mercury lamp.

For nucleic acid amplification, real-time PCR is one example of a nucleic acid assay method that can be performed in tube 250 in temperature controlled region 350 and detected with detector 410.

On Microchip Reactions

Figure 11:
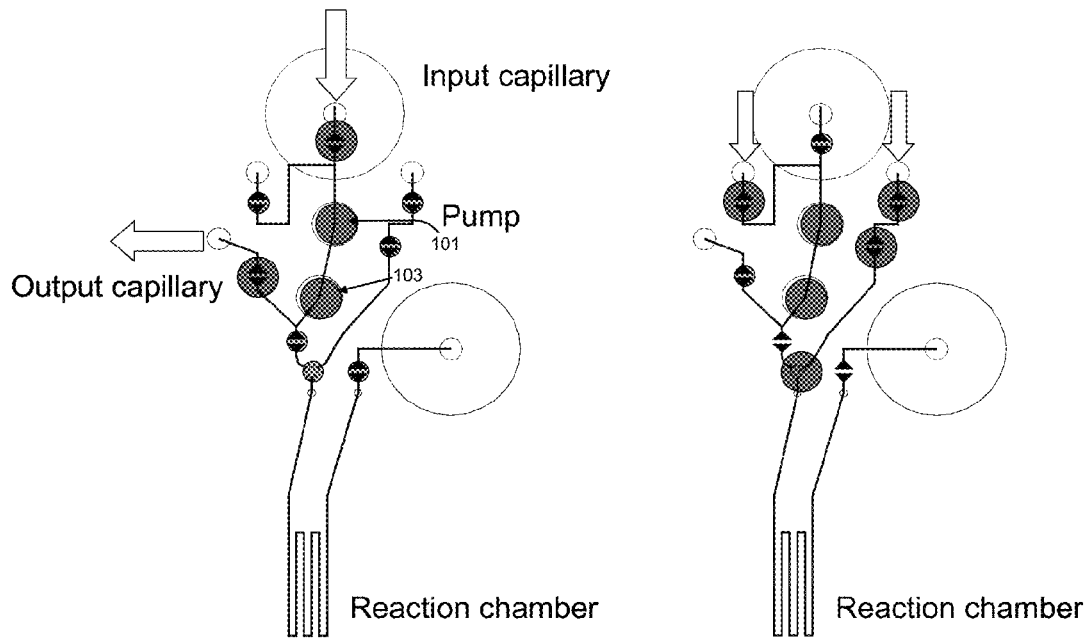
FIG. 11 shows a schematic of using microvalves to capture beads on a microchip.
Figure 12:
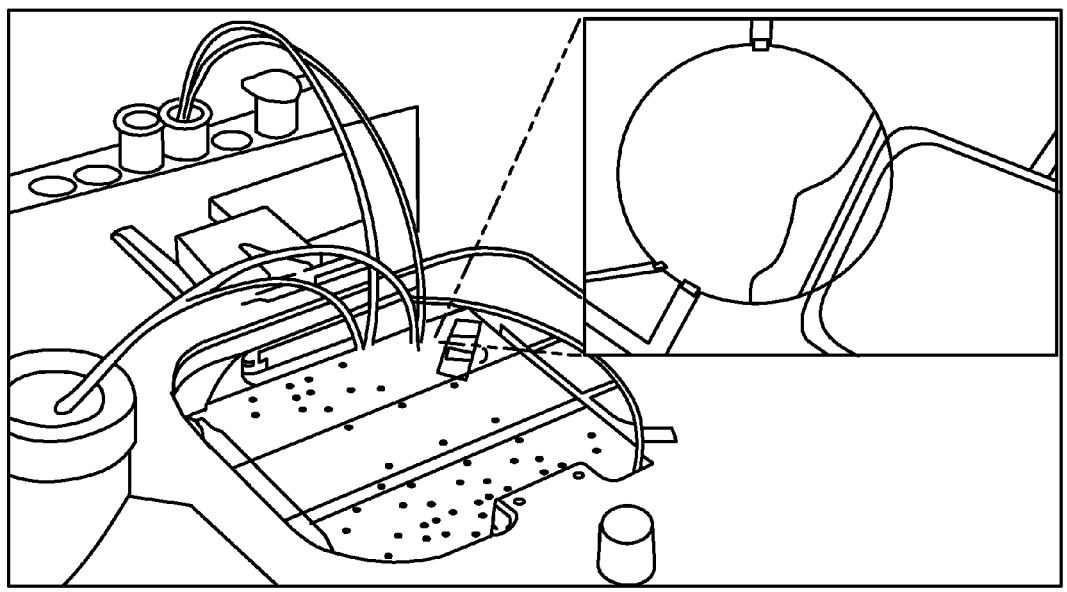
FIG. 12 shows bead capture from a cartridge on a microchip using a MOVe microvalve.

In addition to transfer to tubing, apparatus 1000, as shown in FIG. 6, can transfer material to microchips. To facilitate the movement of this solution onto a microfluidic device for processing a microchip was specifically designed with large MOVe valves for high volume pumping and bead capture, stepped ports for interface with input and output capillaries, side ports for reagent introduction and a 1 μL reaction chamber. Refer to FIG. 11, FIG. 12 and FIG. 14 for microchip details.

FIG. 11 shows a microchip schematic. The left depiction in FIG. 11 diagrams the introduction and capture of beads from the cartridge and apparatus device. The large pump 101 and the magnetic bead capture chamber 103 are fed by a capillary from the cartridge. Input capillary indicates where sample is added through the cartridge. Output capillary indicates where sample is removed through the cartridge. Beads can be placed in the input capillary and then moved into the magnetic bead capture chamber by pumping of valves between the input capillary and the magnetic bead capture chamber 103. Valves are indicated by the dark circles and opposing triangles. A movable magnet can be positioned adjacent to the magnetic bead capture chamber to capture magnetic beads as solution carrying the beads flow through the magnetic bead capture chamber. The diagram on the right illustrates the resuspension of the beads and DNA in the STR pre-mix as the sample is moved into the reaction chamber. The two arrows in the diagram on the right indicate where STR pre-mix and DNA can be added to the microchip. Valves between the location indicated by the arrows and the reaction chamber can be used to pump the DNA or STR pre-mix into the magnetic bead capture chamber for resuspension of beads, and then into the reaction chamber.

Figure 13:
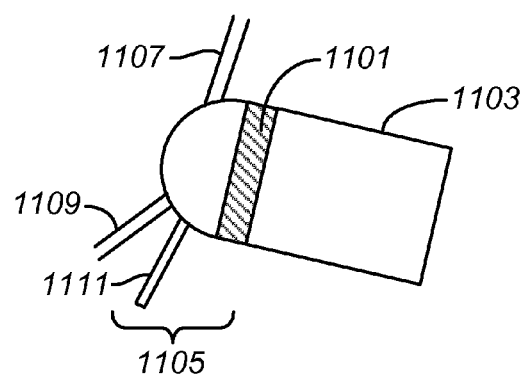
FIG. 13 shows bead capture from a cartridge on a microchip using a MOVe microvalve.

FIG. 12 and FIG. 13 show bead capture on microchip after transfer from cartridge device. The bead capture can be performed by using a magnet positioned adjacent to the microchip such that a magnetic field is applied within a chamber of the microchip. Shown in FIG. 12 and FIG. 13 is a large capacity (500 nL) MOVe valve, which can be utilized for pumping and capture of beads. The capture of beads is shown in the inset with a captured bead bed. As shown in FIG. 13, the magnet 1103 is positioned over valve 1101 of the microchip. Beads, which can flow into or out of the valve through fluidic channels 1111 and 1107, are captured against a wall of the valve due to the magnetic field exerted by the magnet. The valve can be actuated by a pneumatic channel 1109 that can deliver a positive pressure or negative pressure, relative to the fluidic chamber of the valve, causing the elastomeric layer of the valve to raise or lower.

Figure 17:
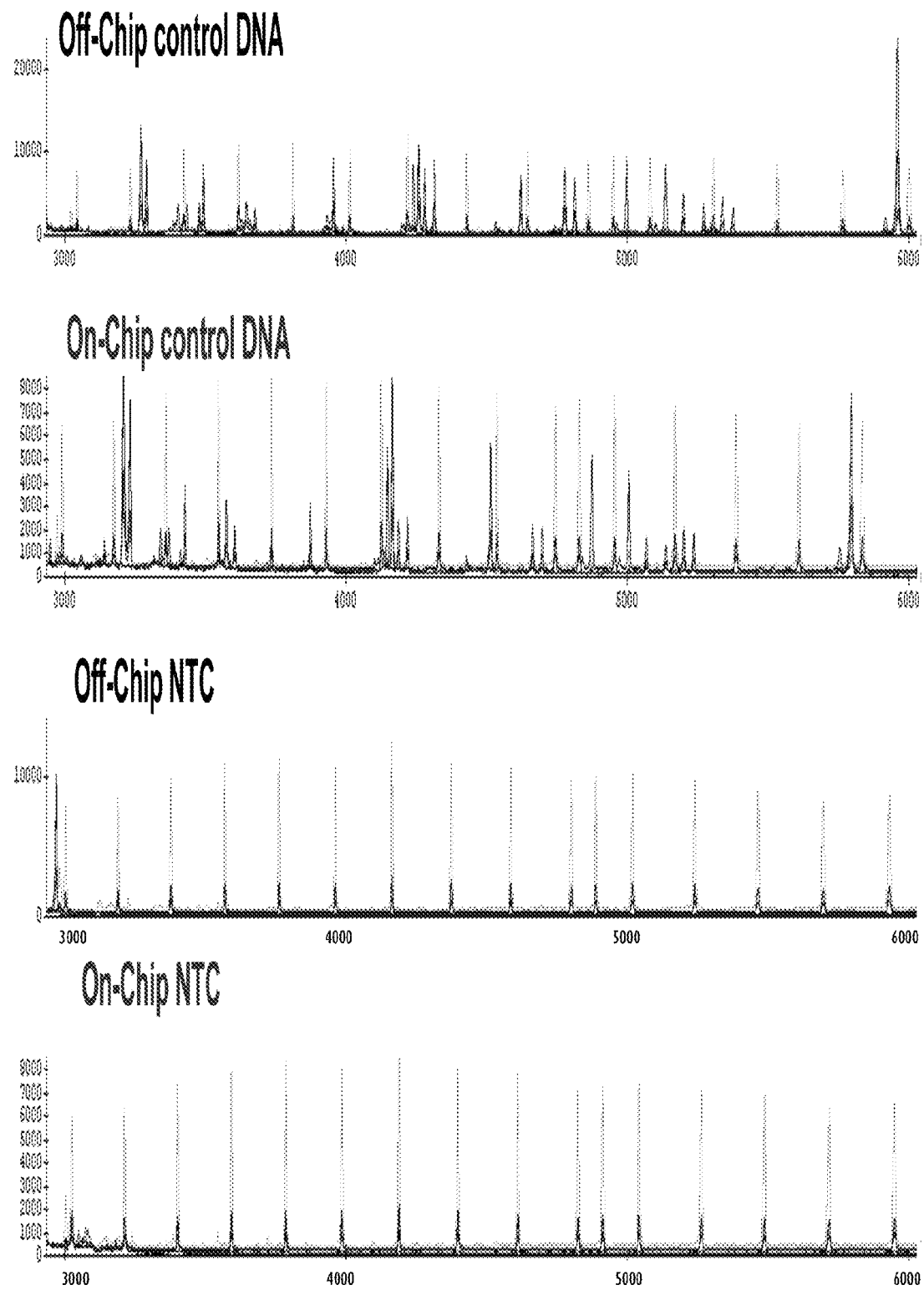
FIG. 17 shows an example of STR reactions on microchips.

One microliter on microchip reactions has been successfully run with good signal strength and relatively good loci balance. FIG. 17 shows the results of reactions with using one microliter on microchip reactions as compared to equivalent off microchip reactions and no template controls (NTC) that contain only size standards. Peaks represent detection of nucleotide base pairs.

Purification of Reaction Products on Beads.

In one embodiment, the reaction products on the beads can then be moved into cartridge (1) using vacuum applied to the reagent connection 5 with microvalves 200 and 130 open with the path connecting through 201, 212, 211, to junction 210 and channel 19 and 9 to chamber (3) through 131, 141, and 140 to reaction channel 250. The microvalves on microchip 500 can modulate the vacuum and flow. The reaction products can be moved into chamber (3) which can be loaded with beads that are cleaned in place as described above.

The beads can capture many types of biomolecules using affinity or other interactions well known to one skilled in the art using bead purifications, immunomagnetic separations, and reactions with beads, nanoparticles, quantum dots or other types of particles.

Continuing the STR example, after STR amplification is complete, the reaction products are transferred back to the cartridge (1) using vacuum. Amplified STR products are purified, desalted and concentrated prior to injection using the same Orapure magnetic bead beads present on the device for the isolation of DNA from the buccal swab. This time the beads are used with only ethanol; no PEG/NaCl solution as described previously for the swab extraction is used.

The beads are loaded into the cube mix chamber, captured and cleaned with 70% ethanol. Then the 5-10 µL of STR reaction is pulled back into the chamber from the cycling zone and into contact with the beads. A 20 µL chase solution of electrophoresis run buffer (chosen because of its availability on the separation subsystem) is pulled through to scavenge any remaining STR reaction solution in the reaction channel and 100% ethanol is added to take the solution up to a 95% total ethanol concentration.

Figure 19:
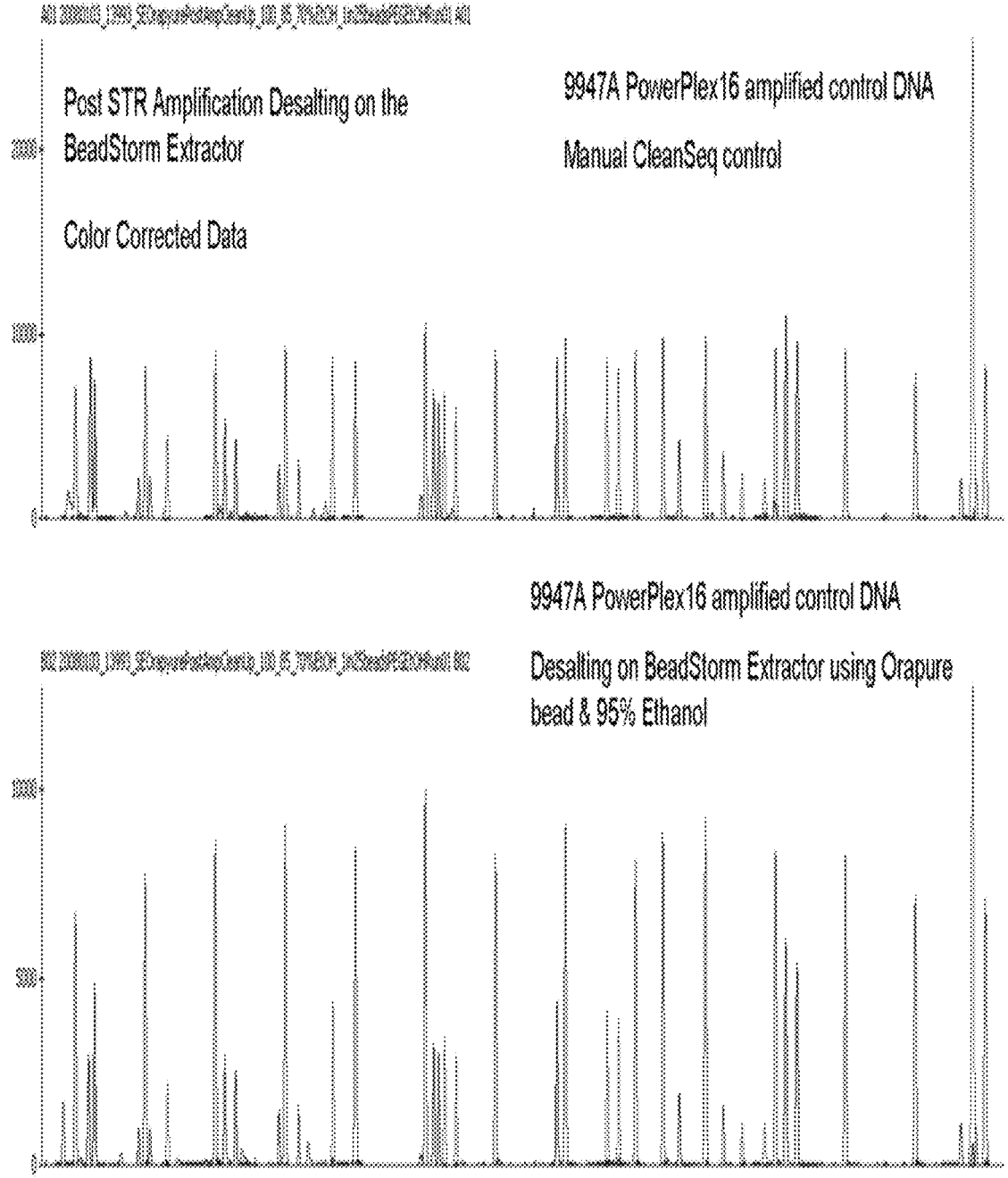
FIG. 19 shows purification of samples in a cartridge using paramagnetic beads.

FIG. 19 shows data for standard material prepared in this manner on the swab extractor and analyzed on a MegaBACE. The products were cleaned with Orapure beads in the sample preparation device configured as a swab extractor using cartridge (1) and compared to products that were cleaned using a manually prepared control that had been processed with CleanSeq (Agencourt). About ~60% recovery was observed in comparison with the same process performed off device. It should be noted that the swab extractor cleaned material yields significantly more efficient injections than the commonly used process which dilutes the sample by 1:50 to 1:100.

In another embodiment, a Post-amplification STR clean-up device delivers the STR reaction premix to the thermocycler; meters the sample during the isolated DNA bead capture; performs a bead cleanup on the STR amplified products; delivers the eluted products to the cathode; and provides reagents to the cathode assembly during preparation of the separation and detection device and sample injection processes.

Figure 47:
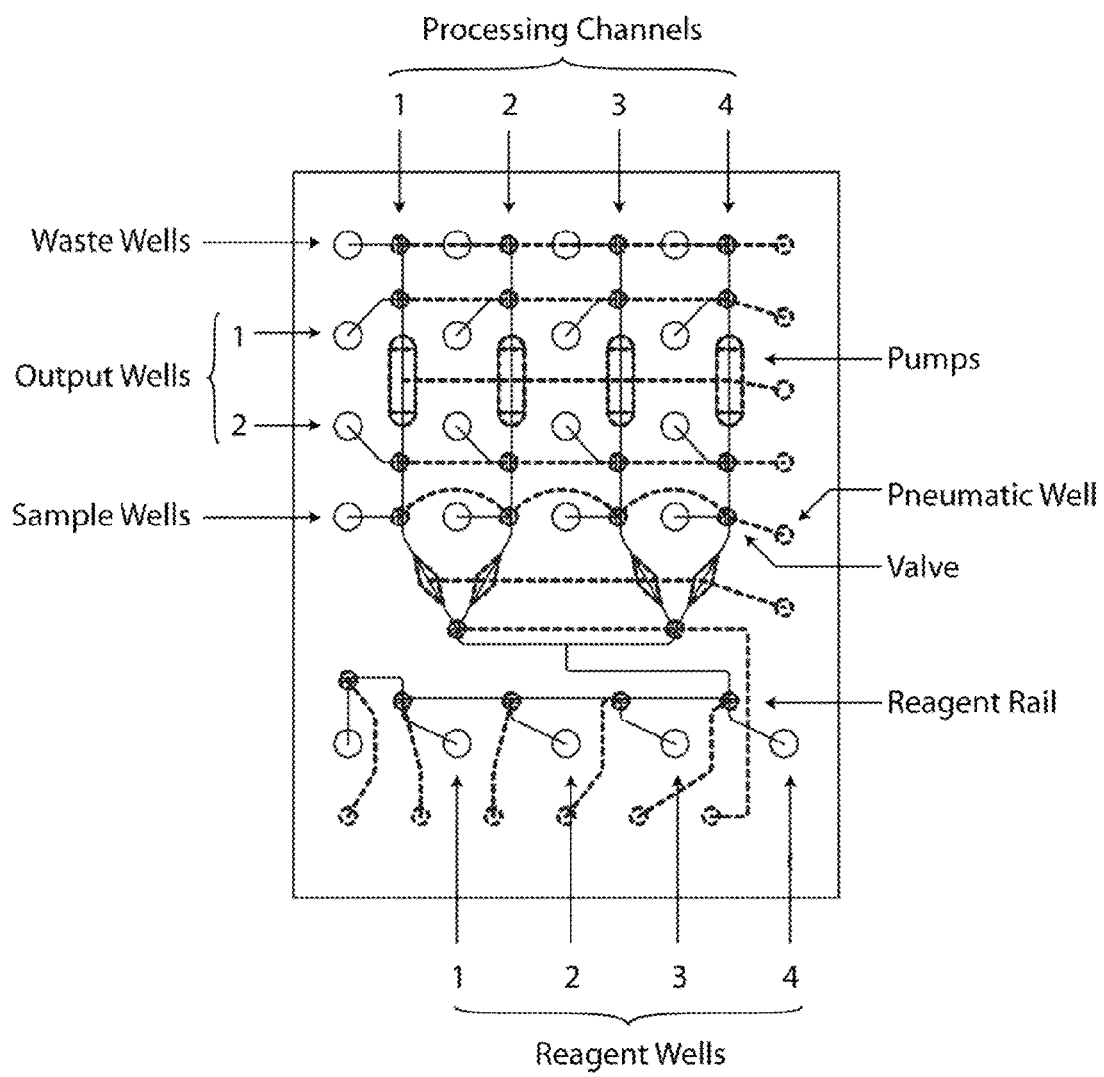
FIG. 47 depicts fluidics and pneumatic layers of a microfluidic microchip with four sets of pumps.
Figure 71:
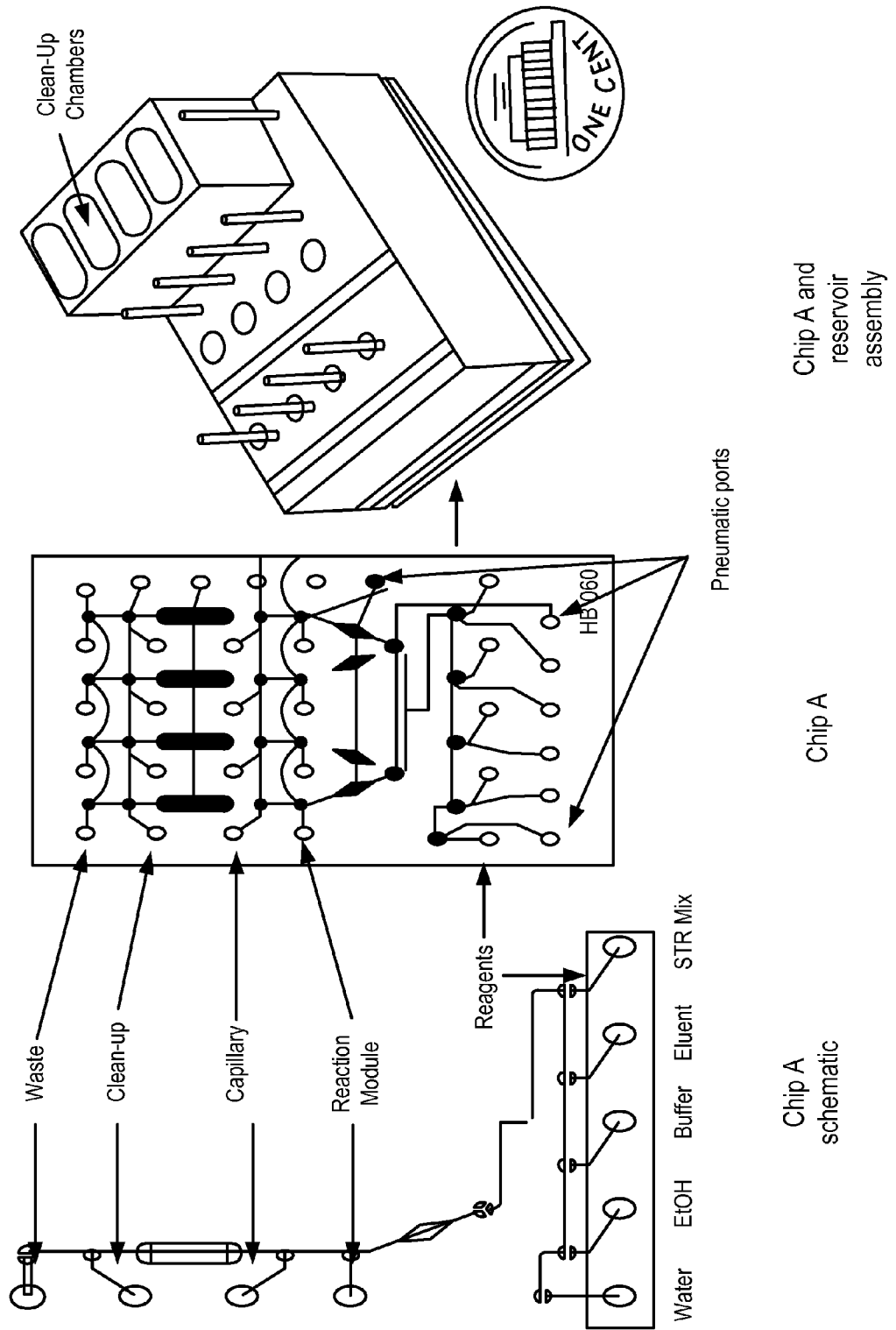
FIG. 71 shows a four-channel post amplification device combined with an Chip A microchip with a fluidics manifold: the Chip A microchip design is shown on the left, the fabricated microchip is shown in the center, and the assembled fluidic manifold and microchip is shown on the right.
Figure 72:
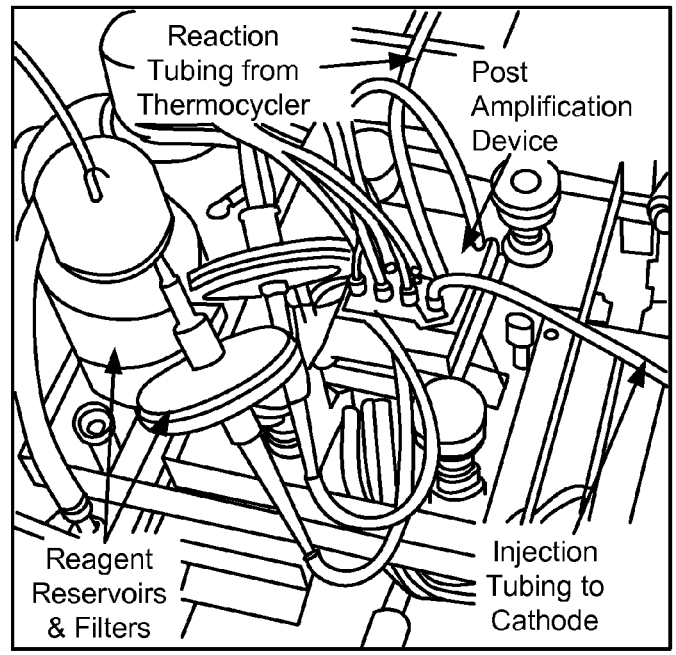
FIG. 72 shows a post-amplification STR clean-up subsystem with the post-amplification device.

The four-channel Post-amplification STR clean-up device combines an Chip A microchip, shown in FIG. 47, with an enlarged fluidics manifold with cleanup chambers (FIG. 71) and mounted on a pneumatics control manifold (FIG. 72). Agencourt CleanSeq beads are delivered to the clean-up chamber, the sample is pumped through the reaction tubing 250 from the thermocycler to the clean-up chamber and ethanol is added. The sample is mixed by air bubbling to facilitate DNA capture onto the beads. A magnet is actuated at the base of the device cause the DNA and beads to be captured against the bottom of the clean-up chamber; the remaining liquid is then pumped to waste. The magnet is moved away from the device and eluent containing fluorescently labeled DNA size standard in a formamide solution is pumped into the clean-up chamber. The STR amplification products are eluted in this solution and the magnet is once again actuated to capture the beads before the purified and concentrated sample and size standard are pumped to the cathode, ready for injection into a separation capillary.

Figure 73:
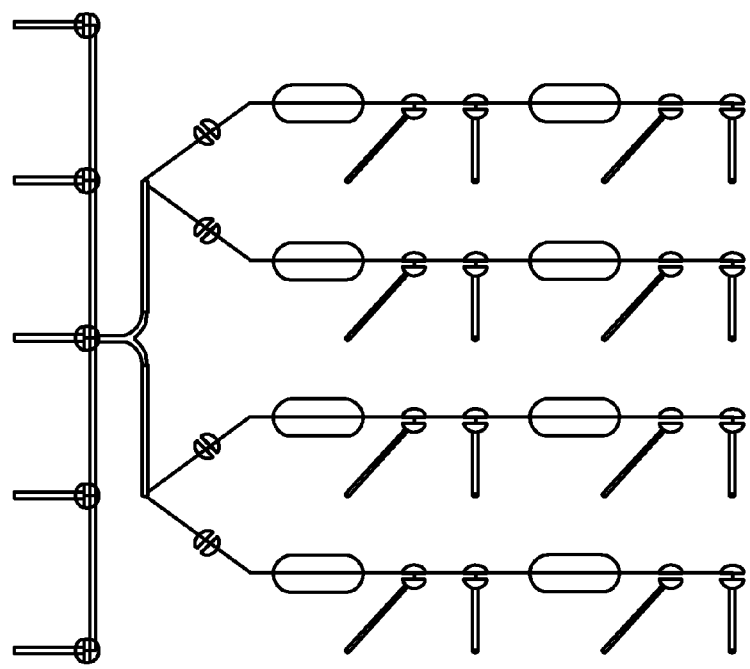
FIG. 73 shows the Chip E microchip design, which can be used a post-amplification device.
Figure 74:
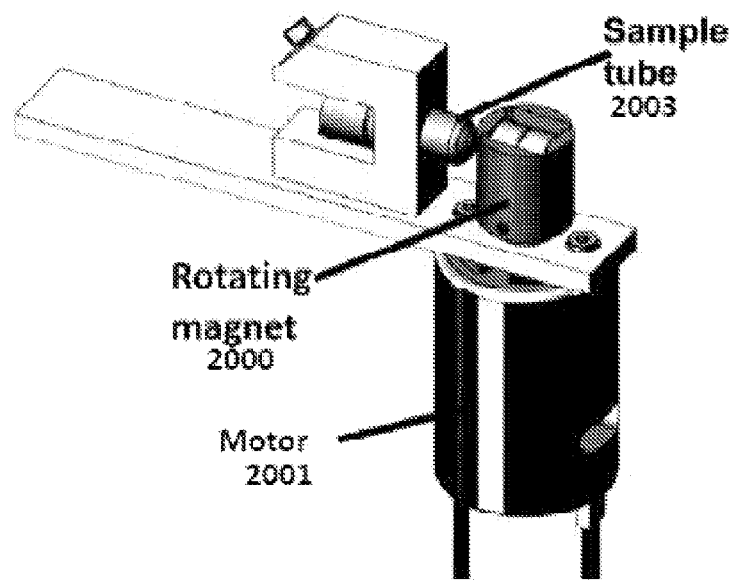
FIG. 74 shows a diagram of a mixer.
Figure 75:
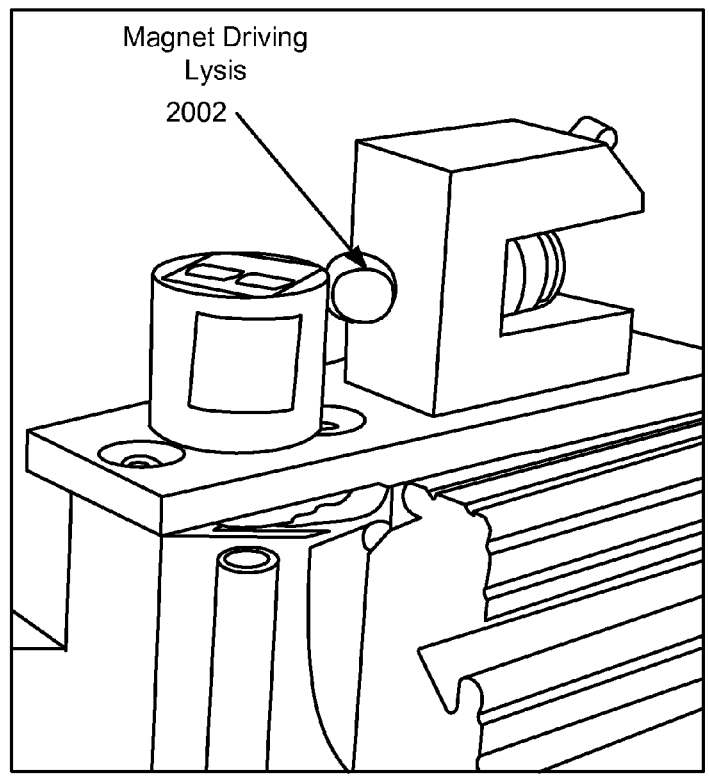
FIG. 75 shows a diagram of a mixer.

Testing of the post amplification device using Chip A highlighted issues with priming and pumping ethanol through the Chip A microchip due to the high level of resistance in the reagent pathway of this microchip. The microchip design, Chip E, (FIG. 73) significantly improves functionality and robustness of the post amplification device by widening channels and replacing three way MOVe routers with a pair of MOVe microvalves.

Example 2

Universal Sample Preparation

The previous example illustrated one embodiment in which the disclosed apparatus can be used to prepare samples for analysis and showed one example of STR amplification. Another embodiment involves the use of a Universal Sample Preparation Module (USPM). The USPM device can consist of a sample processing cartridge (1), accompanying apparatus to operate the cartridge, a microprocessor, and software that can readily be interfaced to downstream analytical devices. In one embodiment the USPM can be tightly integrated with analytical devices to form a modular sample-to-answer system. The cartridge can be configured as a disposable single-use device that can process swabs or liquids (including aerosol samples) for field monitoring processes, or as a reusable, flow-through format for remote operations with rare positives. Target specificity of the USPM is imparted through the use of specific antibodies (that bind selected targets) attached to paramagnetic beads; different cartridges can be supplied with various mixtures of targets.

Figure 18:
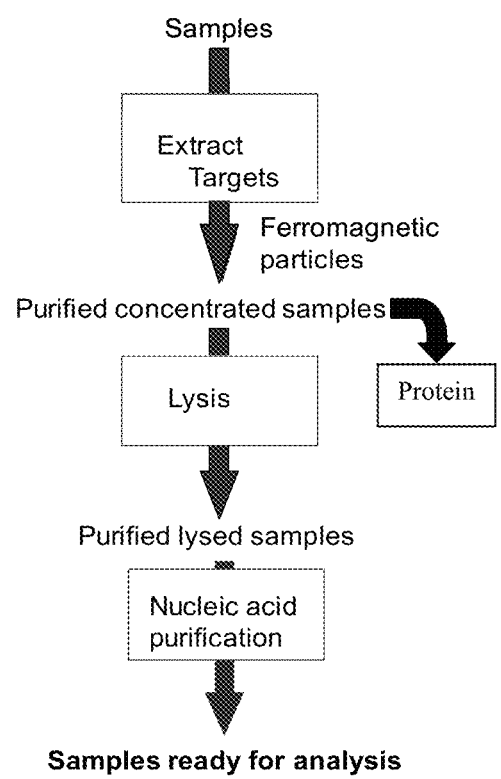
FIG. 18 shows a universal sample preparation workflow to prepare nucleic acids and toxins.

A USPM can use a multistep fully automated process to prepare biological samples for downstream analysis. One example in FIG. 18 can use swabs or liquids; the operator can select the sample type and then insert samples into input port(s). The first step can apply immunomagnetic separations (IMS) to capture, concentrate, and purify target molecules from solution onto paramagnetic beads. Targets already tested include cells, spores, viruses, proteins, or toxins. For toxin and protein detection, or for use as a triggering device, the captured targets from the IMS can be exported directly to the downstream analytical device. For nucleic acid detection, the second step can lyse the cells or spores to release the DNA and/or RNA using mechanical or other lysis techniques. The third step, nucleic acid purification, can adsorb, concentrate, and purify the nucleic acids onto a second set of paramagnetic beads and output the beads with nucleic acid, or purified desorbed nucleic acid, for downstream analysis.

Referring to cartridge (1), the immunomagnetic separation can be performed by using reagent beads that have antibodies or other immunomagnetic, affinity magnetic, or surface chemistry magnetic separations. For example, immunomagnetic beads with antibodies can be added to cartridge (1) to capture, purify, and concentrate cells, viruses, spores, toxins and other biomolecules onto bead.

Upstream sample processing for the USPM can be done in the sample preparation devices, which can process samples over 0.6 mL in a microfluidic cartridge (1) (FIG. 21). The sample processing cartridge, about 1 in cubed dimension, (FIG. 3, FIG. 21) was developed to automatically remove collected buccal cells from a swab, lyses the cells, and purifies released cellular DNA on magnetic beads. The bead beds are typically 100 nL and can be used for downstream STR analysis with microfluidics devices or full scale qPCR reactions.

The sample preparation device uses a MOVe microvalve microchip interfaced with the bottom of the cube (FIG. 3, arrow labeled 2) to direct pressure-driven flows consisting of fluids, beads, and samples among the reagent and reaction reservoirs. The MOVe microvalves replace conventional valves and tubing between the reservoirs, thereby providing a non-leakable, directable fluid transport and enable miniaturization of the entire cube and sample preparation device.

Figure 10:
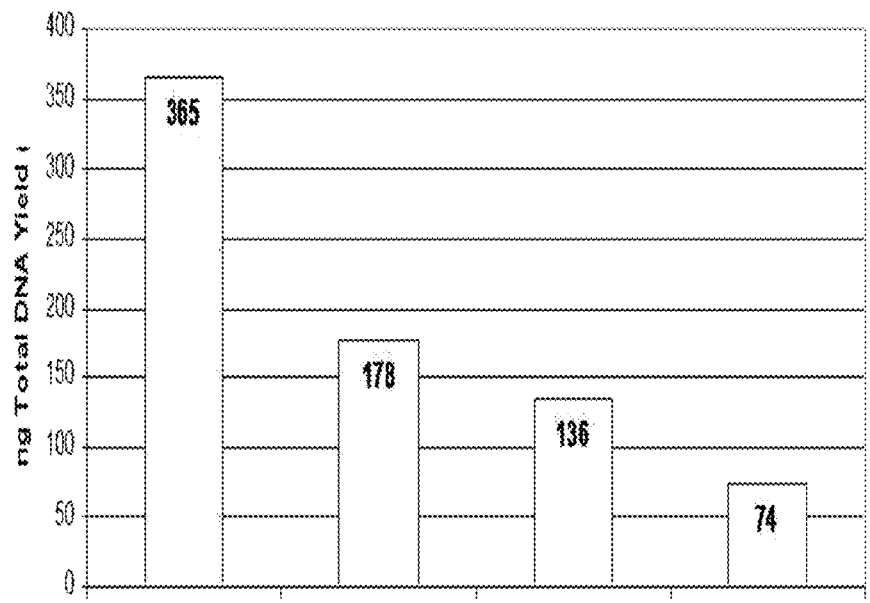
FIG. 10 shows purification of DNA from 25 uL of blood at 69', 23.5', 10.5', and 4.5'; yield in ng is shown on the bars.

This sample preparation device technology has been used to automate DNA extraction from buccal swabs as described above. FIG. 10 shows automated preparation of DNA from 25 uL of blood in the automated sample preparation device using pressure driven flows, vibrational mixing, MOVe valves, actuated magnets, and magnetic beads. The fully automated process produced DNA ready for STR analysis in less than five minutes.

Figure 27:
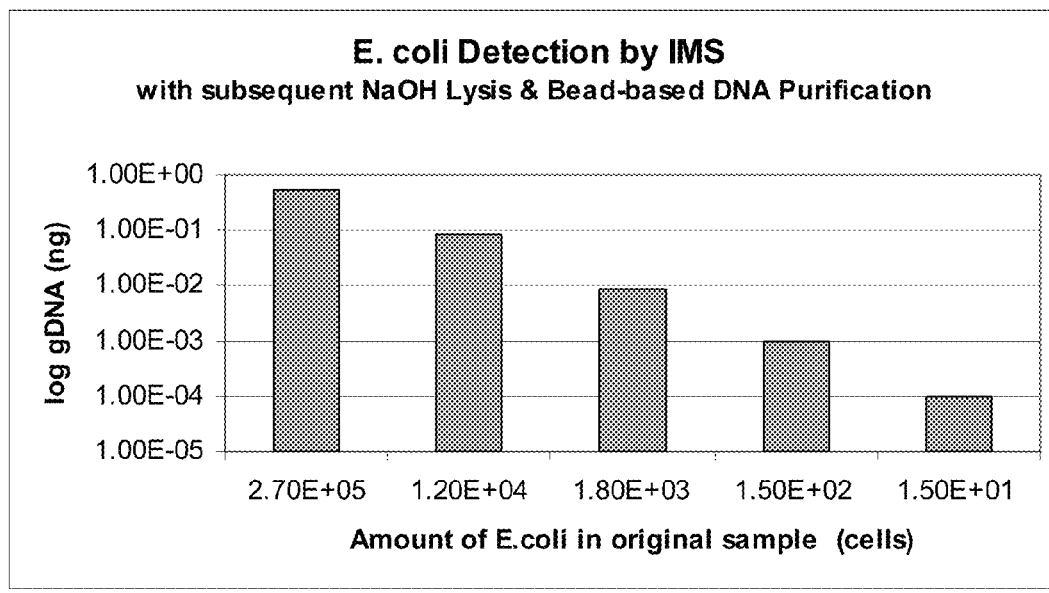
FIG. 27 shows detection of E. coli by immunomagnetic separation, followed by alkaline lysis and PEG-facilitated capture on magnetic beads, and analyzed by real-time PCR.

We have developed an automated system for capturing, concentrating, and purifying cells, viruses, and toxins from liquid samples (1-10 mL) using magnetic beads coated with antibodies specific to targets of interest. Thus, a variety of targets have been concentrated and purified with this automated system. Using this approach, *E. coli* cells were captured and detected at cell concentrations as low as 15 cells/mL/sample (FIG. 27). Similar results of greater than 90% capture efficiency were obtained using *Bacillus* spores, $Gm^+$ and $Gm^-$ vegetative cells, a model virus (bacteriophage fd), SEB, and ovalbumin as targets. Purified samples can be further processed in the sample preparation device (e.g., lysis and nucleic acid purification), moved onto a microchip for analysis, or used with an off-chip PCR/qPCR device.

We have shown that IMS capture works well in complex samples such as aerosols and in the presence of biological clutter (See U.S. Patent Publication No. 20080014576, herein incorporated by reference in its entirety). For clutter, we showed that up to $10^5$-fold levels of added bacteria produced only a two-fold reduction in capture efficiency. For complex samples, add-back experiments using many different aerosol samples established that aerosol samples reduce the binding of *B. cereus* spores to IMS beads by less than 50%. Therefore, there is less than a two-fold loss of sensitivity in complex, real-world samples.

We have used IMS to capture, concentrate, and detect toxins. We have developed IMS assays for ovalbumin and SEB, multiplexed the assays, and developed two generations of completely integrated microfluidic systems that automate the IMS assays. Less than 10 ng of SEB can be reliably detected in a one mL samples with no interference from closely related *Staphylococcal* enterotoxins.

We have shown that IMS can:

Select target organisms from samples with high backgrounds of interferents (selectivity), Discriminate between two different strains or species of bacteria (specificity), Effectively capture cells and toxins across a wide range of concentrations from a wide range of samples (sensitivity, robustness)

Reduce target sample volume significantly, from mL to nL volume

The instant invention and the apparatus and methods are capable of implementing IMS and coupling it to nucleic acid extractions.

The next step in the USPM is the lysis of the captured target when it is a cell, virus, prion, or spore. Lysis of spores is particularly challenging. A MagMill or magnetically driven lysis or homogenizing device has been developed for efficient lysis of *Bacillus* and other spores, as well as vegetative cells. The MagMill consists of a rapidly rotating magnet 2000 actuated by a motor 2001 (FIG. 74) that drives rotation of another magnet 2002 contained within a sample-containing vessel 2003 or compartment (FIG. 75). The magnet 2002 contained within the sample-containing vessel can have any shape. For example, the magnet can have a bar, spherical, cylindrical, rectangular, oval, hexagonal, or propeller shape. Alternatively, the magnet can have holes through it, such that liquid may be forced through the holes and increase the shear force applied to the sample when the magnet is rotated by a magnetic field. The same basic components can be miniaturized, incorporated into a microfluidic format, or connected to a microfluidic format. The overall effect is analogous to a magnetic stir plate, with the sample being rapidly vortexed within the sample tube. Using magnetically driven sample agitation by MagMill treatment, spore lysis is achieved without silica, zirconia or other beads. Lysis may be accomplished by shear forces generated as the spore passes between the magnet and the vessel walls. The magnet can rotate at a rate of greater than about 10, 50, 100, 150, 200, 250, 500, 750, 1000, 1500, 2000, 2500, 5000, or 10000 rpm.

Figure 76:
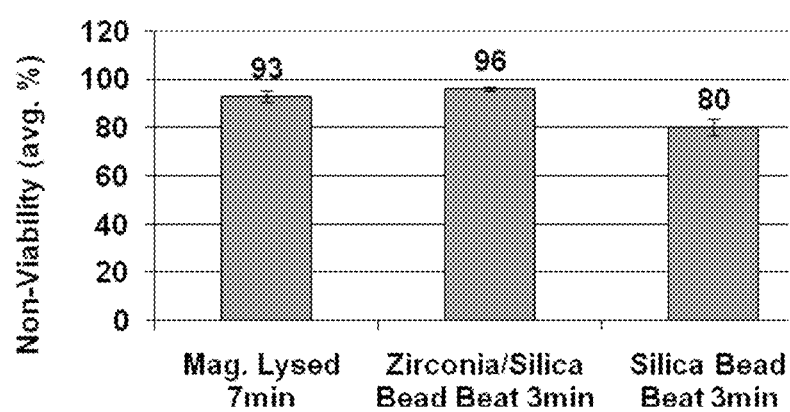
FIG. 76 shows results of using a mixer to lyse cells.

This device disrupts spores with similar efficiency as traditional bead beating that employs silica/zirconia beads (FIG. 76). Spores ($3.2 \times 10^7$) were lysed in a volume of 1 ml with viability was determined by plating on Tryptic Soy Agar; results are an average of two separate experiments each run with duplicate samples (total n=4). The non-viability of magnetically-driven spore lysates was 93% compared to traditional bead beating (BioSpec beater) lysates using either Zirconia/silica which was 96% or silica beads which was 80%. The same pattern was confirmed by qPCR The advantage of using the MagMill (versus traditional bead beating) is that the design is more mechanically robust and thus able to withstand many cycles of use without failure, and samples can be lysed using just the agitation of the magnet in the sample, without the need for inclusion of silica/zirconia beads that have been shown to bind released DNA causing a loss in follow-on detection sensitivity. The basic features of the MagMill can be reconfigured in a miniaturized format that can be integrated into a sample preparation device. The system can potentially be down-sized to fit into a microfluidic microchip. Despite changes in configuration, however, the principle driving lysis, that of a rapidly rotating magnet contained within a sample vessel, remains the same.

Example 3

Sample Preparation for Library Construction

The cartridge (1) technology and the sample preparation device can be further used to perform a series of complex molecular biology reactions in small volumes with bead-based manipulation of DNA samples. The DNA can be processed to prepare genomic libraries for next generation sequencing systems (i.e., Roche 454 system, or the Applied Biosystems SOLiD), Real-time PCR, or other DNA assay systems.

By incorporating a reverse transcriptase step, RNA libraries can also be converted into DNA libraries by essentially the same method. The advantage of building an RNA library is that the representation in the final amplified library will directly mirror the original starting material since the amplification will be based upon single molecule amplification.

Figure 29:
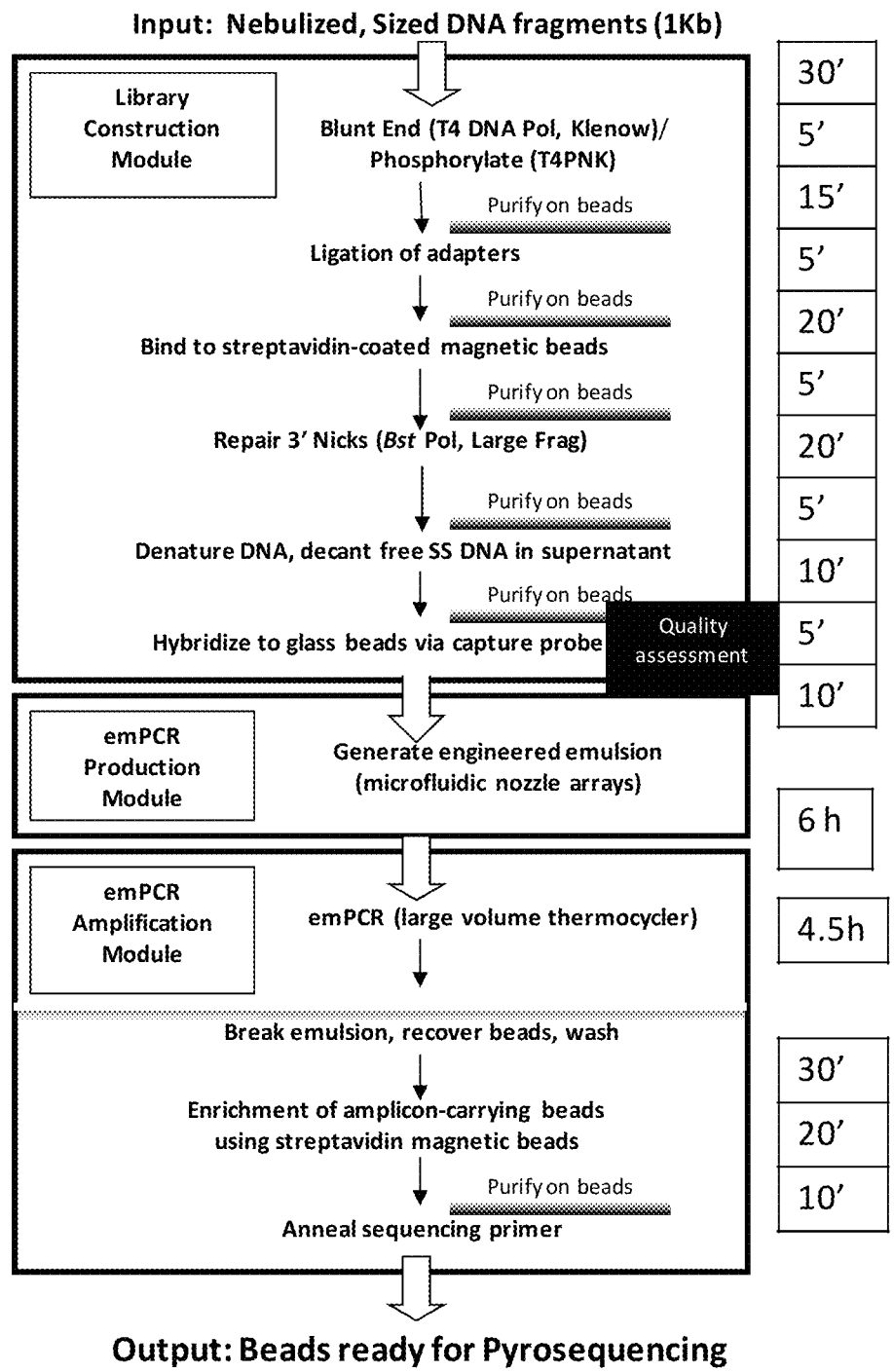
FIG. 29 shows the workflow to prepare genomic libraries using the cartridge.

The design concept for the Library Construction Module (LCM) is an instrument that holds bulk reagents and provides fluidic control to the small disposable Library Construction Module cartridges that processes individual libraries. The LCM instrument can control fluid flow, mixing, temperature, and bead manipulation in LCM cartridges through DevLink software. An array of reagents stored in temperature controlled reservoirs can be accessible through a MOVe block of valves (actuated by computer-directed pneumatics 700). Workflow for producing beads with amplified DNA attached from single molecules is shown in FIG. 29. The Library Construction Module uses the cartridge as a preferred implementation.

MOVe valves are extremely durable, compact, inexpensive compared to conventional valves, have dead volumes of about 10 nL, and are compatible with dispensing volumes as low as 100 nL. The instrument can use pressure-driven flows to move fluids from the reagent reservoirs through the MOVe valve block, to the reaction chambers in the LCM disposable cartridge, and out to final sample output vessels (FIG. 25). Reagents and substrates can be mixed in sample preparation devices using pressurized flow, vibrational mixing, and pneumatic-driven MOVe valves; magnetic beads are captured and released using DevLink-controlled actuated magnets.

Each disposable LCM cartridge can contain embedded MOVe valves (FIG. 28). The MOVe valves direct fluids from reagent reservoirs and connect the three reaction chambers. One chamber, the processing chamber A, can carry out the sequential solution-based molecular biology reactions. The second, the purification chamber B, can be for bead-based purification of intermediate products. The third chamber, the annealing chamber C, can perform the final annealing to glass beads. The annealing chamber can comprise a filter to separate the beads from surrounding solution. Pneumatic lines (P1, P2, P3, P4, P5, P6, P7, and P8) can control the valves of the microchip that control and/or force flow to the chambers.

Pressure driven flow through the MOVe valves can move fluids between chambers. The processing and annealing chambers can be capable of mixing contents and incorporate thermal control.

In the next sections, the workflow to prepare DNA library samples using the LCM is described as an example. It is readily apparent that RNA libraries can be prepared after a reverse transcriptase step.

Demonstration of Microfluidic Reactions Preceding emPCR

The starting input for the Library Construction Module can be nebulized, sheared DNA that has been size fractionated to 800-1,000 bp, purified, and has already had small fragments (<500 bp) removed. Size fractionation can also be carried out on the LCM by selective binding to magnetic beads, e.g., AMPure, (Agencourt). Input DNA can be assessed for size and concentration on a BioAnalyzer 2100 (Agilent) and by dye binding (Pico-Green, Quant-it, Invitrogen). The sequence of reactions is shown schematically in FIG. 29 in the Library Construction Module box.

Fragment End Polishing

In one embodiment DNA nebulization generates fragments with a preponderance of frayed ends that require filling in/blunt-ending before further manipulations can take place (Bankier 1987). Phosphorylation of 5' hydroxyl termini is also required for subsequent ligation of adapters. This can be accomplished through the successive activities of T4 DNA polymerase and T4 polynucleotide kinase. Substrates are combined with reaction buffer, BSA, ATP, dNTPs and the two enzymes in a small reaction volume, initially 25 uL, incubated first at 12 degrees Celsius for 15 min., then at 25 degrees Celsius for 15 min. Temperature control can be through Peltier devices mounted on the hard instrument interface. Controls for the polishing reactions can rely on incorporation of fluorescently labeled dNTPs, assayed using fluorescent imaging and quantification or using radiolabeled dNTPs.

Microfluidic Bead-Based Purification

Following polishing, the fragments are purified by precipitation onto beads. The LCM instrument can move fluids to the LCM cartridge (see FIG. 28) to force DNA onto beads, actuate a magnet to concentrate beads onto a wall of the purification chamber, and then wash the beads. As needed the DNA can be eluted from the beads, the DNA can be moved to the processing chamber A and the beads discarded, or the beads moved into another chamber for further processing. This method can be reused multiple times throughout the process. Column-based purifications are thus replaced with bead-based purification. The sample preparation device routinely purifies DNA in cartridges using magnetic SPRI beads (Agencourt Biosciences), DNA IQ(Promega), and carboxylated beads (Invitrogen) for DNA sequencing, forensics, and biodefense applications respectively. Purified products can be assayed on a BioAnalyzer (Agilent) and by dye binding (Pico-Green, Quant-it, Invitrogen).

Ligation of Adaptors

Next, adaptors are ligated to the purified DNA. The DNA in the purification chamber can first be eluted from the beads into ligation buffer, which is moved to the reaction chamber by pressure driven flow, and adaptors and ligase added. The adaptors can contain nested PCR and sequencing priming sites, blunt 3' ends and 5' overhangs; one adaptor of each pair can have a biotin on the 5' end. Each adaptor can incorporate a nucleotide-based 'key' that serves to identify the sample and the processing steps and a 'sequencing key' to assist in base-calling. Ligation and further selection selects for fragments with different adapter (one with biotin, one without) on each end. At this point before being bound to streptavidin beads the ligation products again can need to be purified on beads in the purification chamber and the library moved back to the processing chamber.

Ligations can be conducted with ligase such as quick ligase (New England Biolabs), buffer and adaptors and incubated for 15 min at 25 degrees Celsius. Products can be assayed for the ligation of adaptors by Q-PCR, using the PCR priming sites and 5' sequencing priming site for probe. Efficiencies of ligation and recovery of target can be calculated by comparing the amount of starting materials and yields after relevant steps. Also, pre-binding one adaptor via a biotin-streptavidin linkage to a paramagnetic bead will result in bead-bound fragments that can then be subjected to a second round of ligation with the second adapter. This approach can prevent the generation of fragments with no biotinylated adapters and those with two biotinylated adapters, which are both lost during processing. This could significantly improve the final yield of template. After ligation, the products are again bead-purified.

Library Immobilization

Pre-washed streptavidin-coated beads resuspended in Library Binding Buffer can be added from a reagent reservoir to the purified ligation reaction products that have been moved back to the processing chamber and incubated for 20 min with mixing at RT. The material is then bead purified on the streptavidin bead in the purification chamber to remove adaptor dimers.

Nick Repair

Ligation results in 3' nicks, which can be repaired by Bst DNA polymerase (Large Fragment). Fill-in Buffer, and dNTPs, can be added directly to the beads and incubated at 65 degrees Celsius for 30 min. The beads are then purified in the purification chamber.

25 uL of premixed Melt Solution (125 mM NaOH) can be added directly to washed beads in the purification chamber, mixed, the bead pelleted using a magnet, and the resulting supernatant moved to the processing chamber where 62.5 uL Neutralization Solution (0.15% acetic acid) can be added. A second round of treating the beads with denaturant results in a total volume of 113 uL of single stranded template. These would again be purified before eluting in a volume of 10 uL.

Automation, upstream normalization of the input material, or using limiting amounts of beads are various steps that can greatly aid in uniform production and amplification of libraries, which can lead to the elimination of the quality check at this point.

In one embodiment, continued quality assessment and functional quantification can be performed. The quality of the SS library can be assessed off-line, if required, using an Agilent 2100 Bioanalyzer, which can provide the size range of fragments; yields can also be assessed using Q-PCR, or dye binding (RiboGreen, Quant-iT, Invitrogen). The library can further be functionally tested by forming a dilution series, performing emulsion PCR (emPCR), and pyrosequencing to determine the working dilution for the emPCR. Automated fragment separation can also be incorporated into the device.

Binding to Capture Beads

The SS DNA prepared in prior steps can be annealed to controlled pore glass (CPG) or styrene beads with bound DNA capture primers complementary to the ends of the ligated adapters. Handling of non-magnetic beads, such as these, can require the use of pumped filtration technology (to avoid the use of centrifugation). Because the reagents used can be purified of any particulates and the beads can be pre-washed and quantified using a Coulter Counter (Beckman Coulter), filter clogging should not be an issue.

The beads can be added to the template library, now single stranded, and mixed to favor annealing of a single template/bead in hybridization solution in the annealing chamber. Initially, the bead-template mixture can be divided into aliquots for subsequent emulsion generation and annealed by ramping from 80 degrees Celsius with holds at 10 degrees Celsius intervals in a standard thermal cycler. Temperature-ramping capabilities can also be incorporated into the LCM device. Resuspension of filtrates (i.e., washed beads) can be accomplished by back washing the filters. Hybridization of the SS library can be assessed by assaying for unhybridized SS DNA in the supernatant by Q-PCR on aliquots before and after bead hybridization. At this stage of processing the single stranded template on beads can be transferred to the emPCR Production Module or similar device for further processing.

Example 4

Figure 32:
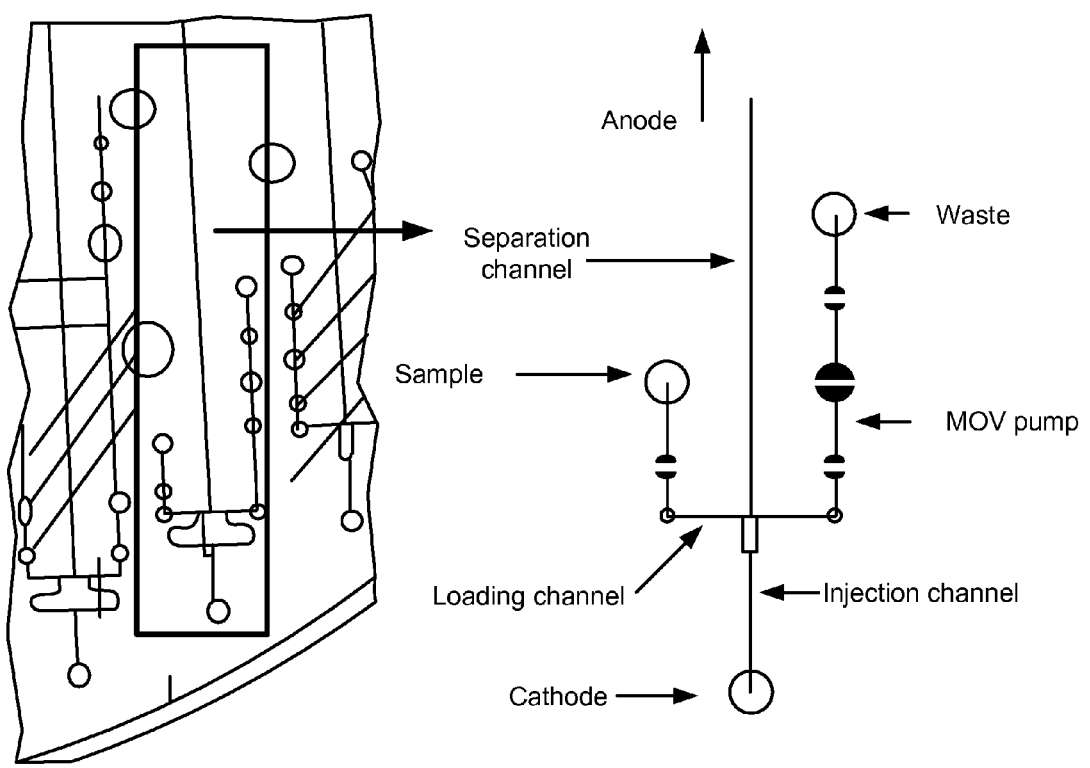
FIG. 32 shows a forked injector coupled to MOVe microvalves.
Figure 34:
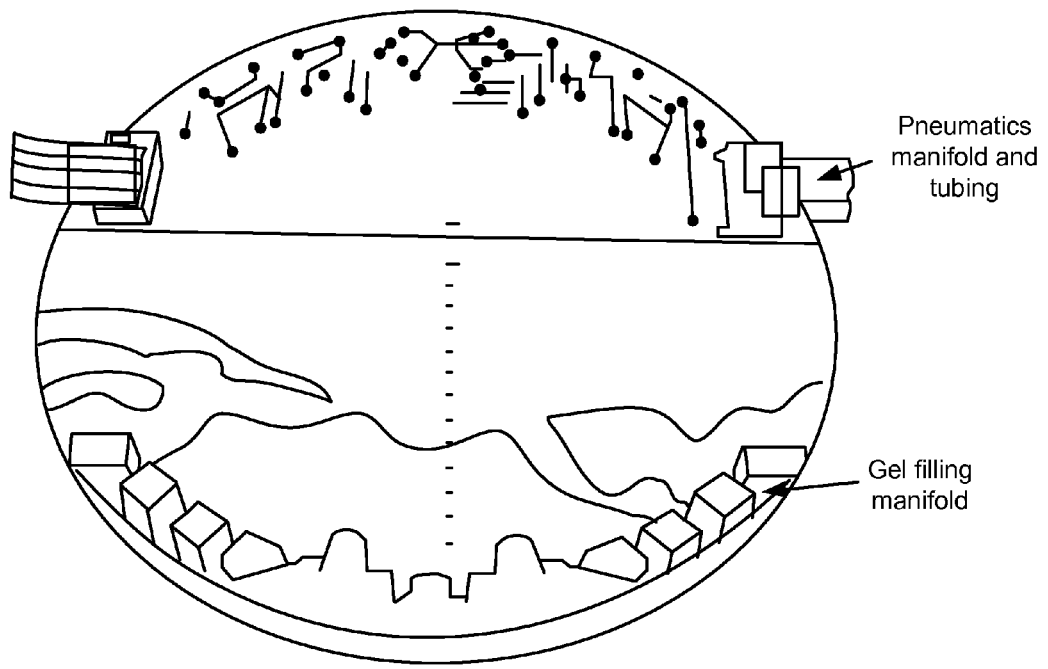
FIG. 34 shows a photograph of a microchip with the forked injector.
Figure 35:
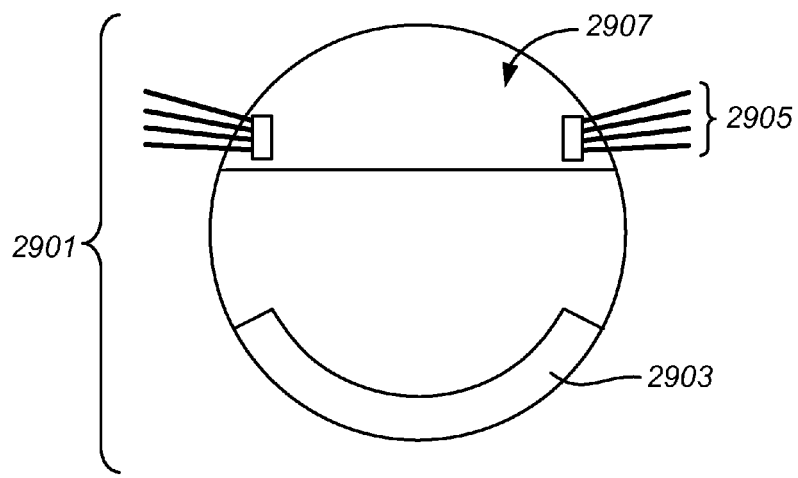
FIG. 35 shows a photograph of a microchip with the forked injector.
Figure 36:
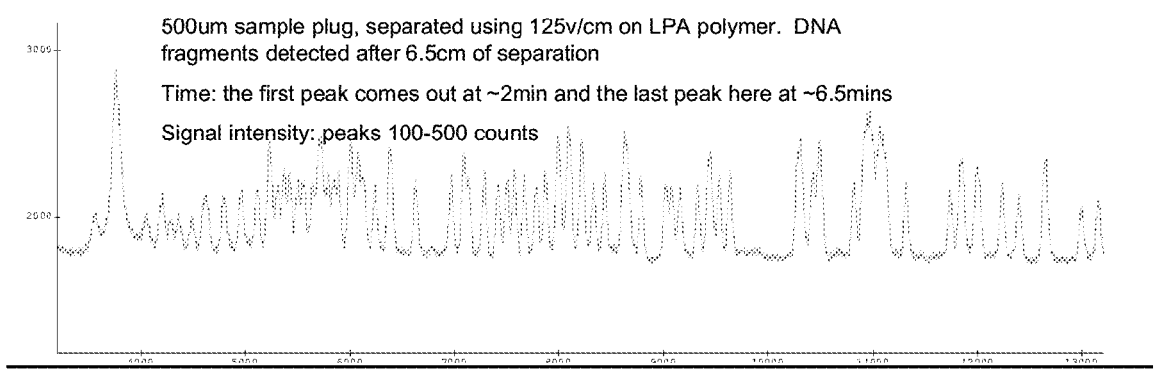
FIG. 36 shows an electropherogram of a single color from a DNA sequencing trace from a forked cathode injector.

Coupling of a Sample Preparation Device with a Microchip-Based Sample Cleanup and Separation FIG. 34 and FIG. 35 show a device with a cartridge (2907) and microchip (2901) that was designed to incorporate the Forked Injector design, as shown in FIG. 32, a gel filling manifold (2903), and associated components. The cartridge is fluidically connected to a pneumatics manifold and tubing (2905). Different configurations of the injector design, separation channel length and separation polymer were tested. FIG. 36 show an electropherogram of an M13 T track injected and separated on a microchip channel using the Forked Cathode injector, with sample detection on a confocal microscope breadboard system. The sample was injected uniformly with short and long DNA fragments represented equally. The results show that an M13 T track DNA ladder can be uniformly injected and single base pair resolution can be obtained out to approximately 330 base pairs in less than 20 minutes. Higher sample signal strengths were obtained compared to injections using a conventional twin T design. When integrated with a detection system, the microchip is held at a constant 50° C. in order to obtain separations with good resolution.

Figure 37:
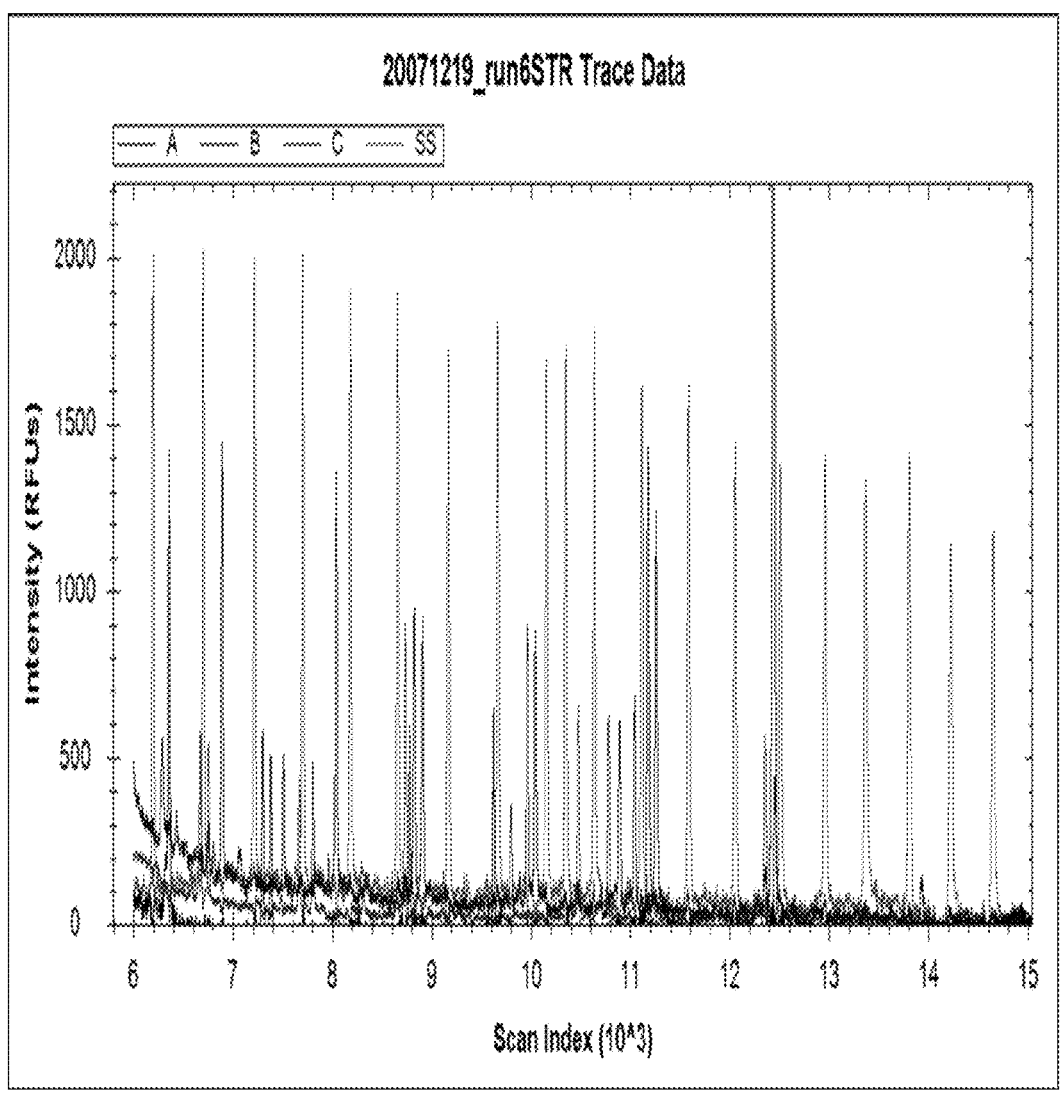
FIG. 37 shows STR separations on a forked cathode injection system.
Figure 37:
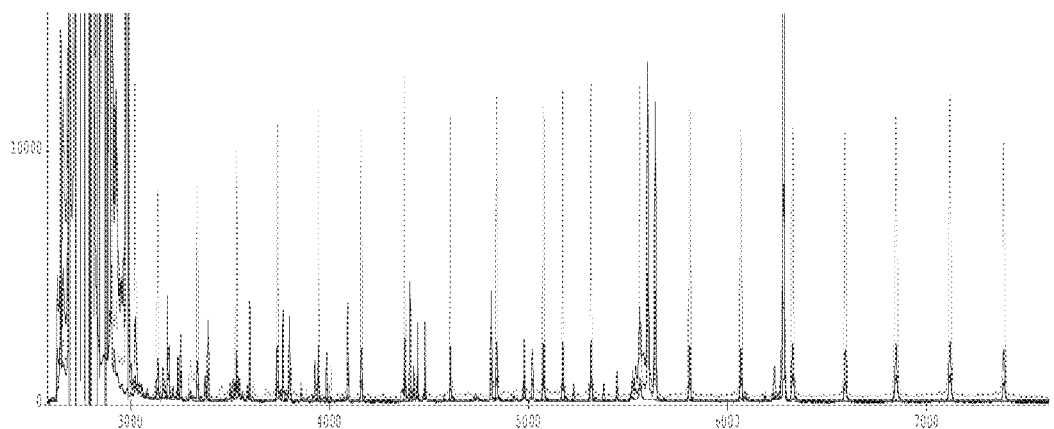

Using these processes, excellent results were obtained for MOVe integrated, field amplified stacking injections of liquid samples (FIG. 37). This data was generated with all sample loading, manipulation and injection processes carried out under software control using MOVe microvalves. The data has been minimally processed, color corrected from a detector that uses eight diode channels to four dye traces.

Figure 38:
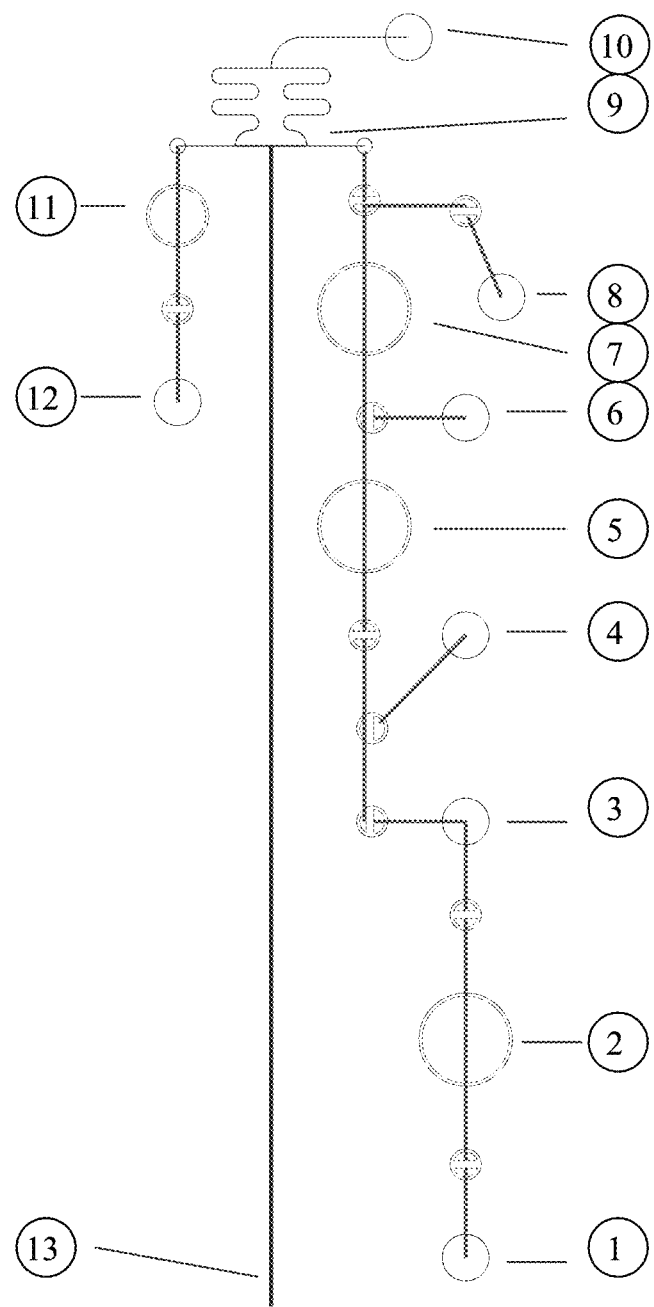
FIG. 38 shows a forked cathode with MOVe microfluidics for shuttle loading.

One embodiment of a microchip that combines the forked cathode with a MOVe sample preparation device is shown in FIG. 38. This device comprised additional processes that enable integration with the rest of the system, i.e., the sample preparation device (1000 shown in FIG. 22), the reaction channel (250 shown in FIG. 6), and the output of the STR purification as described in the STR example. FIG. 38 shows a forked cathode with MOVe fluidics and shuttle sample loading for integration with post amplification STR purification system. The parts are: 1—Reagent input port, 2—Reagent pump head, 3—Sample input port, 4—Size Standard/eluent input port, 5—Capture valve, 6—Waste port, 7—Elution valve, 8—Sample waste port, 9—Cathode, 10—Cathode port, 11—Sample valve, 12—Sample port, and 13—Separation channel. The anode port, which is downstream of the channel, is not shown.

The sample to be separated is introduced as a bead solution in ethanol. This can be the purified reaction products on beads output as described above. In one embodiment, the sample is an STR reaction. In other embodiments, the sample can be nucleic acid fragments of different lengths produced by other reaction chemistries including DNA sequencing by Sanger chemistry. The solution containing the sample is flowed from the Sample input port to the Sample waste port with the Capture valve and other intervening valves open. The open Capture valve facilitates a slowing of the stream flow and bead capture by a fixed magnet placed above or below the valve. The ethanol solution is completely run through the system followed by air yielding a relatively dry and clean bead bed, with purified products, in the valve. At this point the valve is closed and reopened (in coordination with other valves) to fill it eluent solution from the associated port. For an STR analysis or other analyzes where an internal size standard is needed, the eluent can contain a size standard. The solution is moved between the Elution valve and the Capture valve to facilitate mixing, ending with the solution in the Elution valve. The Sample valve is then opened in coordination with the Elution valve closing to "shuttle" the sample through the sample channel leaving it filled. The sample FASS injection is carried out as previously described. An additional noteworthy function of the device is that in one embodiment the Reagent input port and Reagent pump are used to provide metered STR reaction premix to the reaction channel (250 shown in FIG. 6) after the swab extraction of DNA on the sample preparation device; in other embodiments, the device can provide other nucleic acid reaction reagents such as cycle sequencing mixture or provide PCR reagents to perform a PCR amplification followed by providing cycle sequencing reagents to perform cycle sequencing with bead-based cleanup reactions integrated as needed. Other chemistries will be apparent to one skilled in the art.

Example 5

Figure 39:
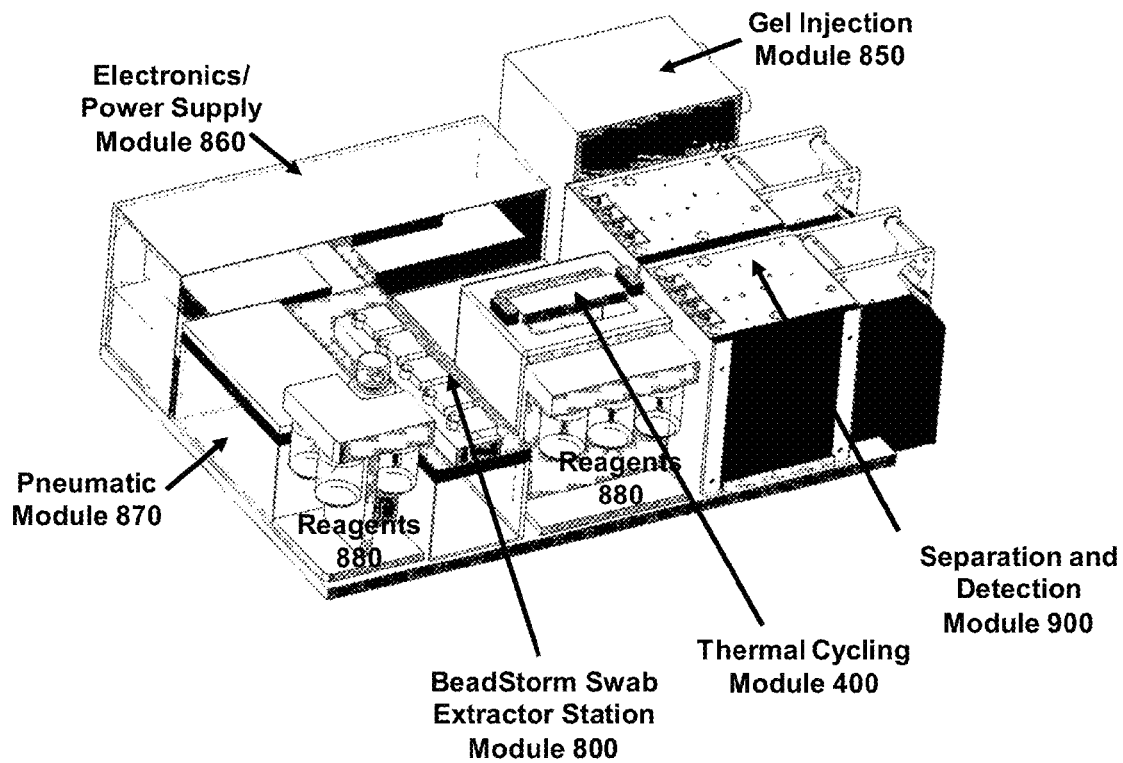
FIG. 39 shows an integrated system for nucleic acid isolation, amplification(s), separation and detection.

Integrated Nucleic Acid Isolation, Amplification, Separation and Detection System A sample preparation device with cartridge(s) and thermal regulating device can be integrated with downstream detection systems to produce a sample-to-answer fully integrated system. The system can be fashioned into a compact format that is compatible with laboratory, clinical, and field operation as a benchtop or portable device, as shown in FIG. 39. FIG. 39 shows one embodiment of a system that can extract swabs or other materials using a five channel swab extraction assembly 800 using cartridges (1) to purify nucleic acids from input buccal swabs, liquids, solids, and other materials. The purified nucleic acids on beads is PCR amplified in Thermal Cycling Module 400. In one embodiment, the samples are bead purified in swab extraction assembly 800 using cartridges (1) to purify the desired products onto beads. The beads are moved to Separation and Detection Module 900 to receive the products on beads, elute the sample and separate it by capillary electrophoresis or microchip capillary electrophoresis or other separation methods with detection methods such as Laser Induced Fluorescence or mass spectroscopy. For capillary electrophoresis or microchip capillary electrophoresis, Gel Injection Module 850 pumps separation matrix or gels or other materials to provide the separation columns and regenerate them. In another embodiment, the Gel Injection Module 850 could pump chromatography media if the separation was by HPLC or other liquid chromatography methods. Electronics and Power Supply Module 860 provides control and power function. Pneumatics Module 870 supplies regulated air and vacuum to operate the swab extraction assembly 800. Reagents are stored in reagent storage 880. Reagents can be stored in solution or dehydrated or stabilized forms such as Ready-to-Go (GE Healthcare) and lyophilized forms.

In one embodiment, the system is configured to perform STR analysis of buccal swabs. Buccal swabs are extracted in assembly 800 and the extracted samples amplified in Thermal Cycling Module 400 using reagents for STR amplification. The amplified samples are purified using nucleic acid extractions onto beads, for example using Orapure or DNA IQ chemistries and beads. The purified STR products on beads are then moved to Separation and Detection Module 900 and the beads are captured and the DNA eluted, preferably on a microchip with MOVe microvalves. The samples are then injected preferably into a Forked Cathode Injector on a microchip or a capillary electrophoresis capillary coupled to a microchip and using capillary gel electrophoresis separations with gels such as dynamic coating gels, V2E (GE Healthcare), polydimethyl acrylamide, the POP family of matrices (Applied Biosystems), hydroxymethylcellulose, guarin, and linear polyacrylamide. The detected products with fluorescent labels pass a Laser Induced Fluorescent detector which detects the peaks as they move by.

In another embodiment, the system is configured as an integrated DNA sequencer. The sample is extracted in assembly 800 and the extracted samples amplified in Thermal Cycling Module 400 using reagents for PCR amplification. The samples can be whole organisms, tissues, cell, viruses, air, liquid, or solid without limitation. The DNA extraction can be non-specific using a bead-based purification method such as Orapure (Agencourt) or can use hybridization or other methods to select one or more regions from the input sample to produce a less complex sample. It will be apparent to one skilled in the art that the USPM workflow with IMS followed by the nucleic acid purification can also be adapted to the sample preparation device 800 and the swab extraction replaced by many other initial purification workflows. The PCR amplification can be of a single region or multiplexed to target multiple regions. The amplified PCR samples are purified using nucleic acid extractions onto beads, for example using Orapure or DNA IQ chemistries and beads. The purified PCR products on beads are then moved to the Thermal Cycling Module 400 and cycle sequencing master mix added and the samples cycle sequenced. This can be with fluorescent labels or as four sets of unlabeled primers for label-less detection by UV or other methods. The cycle sequenced samples are then moved to assembly 800 and bead purified to remove unwanted ions and labels, and other material. The beads are then moved to Separation and Detection Module 900 and the beads are captured and the DNA eluted, preferably on a microchip with MOVe microvalves or into capillaries. The samples are then injected preferably into a Forked Cathode Injector on a microchip or a capillary electrophoresis capillary coupled to a microchip and using capillary gel electrophoresis separations with gels such as dynamic coating gels, V2E (GE Healthcare), polydimethyl acrylamide, the POP family of matrices (Applied Biosystems)hydroxymethylcellulose, guarin, and linear polyacrylamide. The detected products with fluorescent labels pass a Laser Induced Fluorescent detector which detects the peaks as they move by.

In other embodiments the protein, carbohydrate, or other assays are performed and the detection is by mass spectrometry, imaging, HPLC, GC, or other analytic methods well known to one skilled in the art.

For DNA, the processed sample can be amplified by PCR, rolling circle, branched DNA, EXPAR, and other DNA amplification methods well known to one skilled in the art or analyzed by mass spectroscopy or single molecule detection methods. RNA can be processed by Reverse Transcriptase real time-PCR, or samples prepared for DNA microarrays, or other analytical methods. Real time or end point analyzes can be performed with the apparatus. For proteins, assays can be performed in the cartridge including enzymatic assays, sandwich immunoassays, antibody precipitation, protein digestion, protein and peptide labeling, and other commonly used protein analysis methods. Similarly, other cellular components or chemicals can be extracted or purified using standard methods in the apparatus. Molecular biology methods are readily adapted to the apparatus. Samples can be completely analyzed on the apparatus in a single cartridge, moved to a separate cartridge, or analyzed or further processed in a separate instrument comprising a capillary electrophoresis system or microchip capillary electrophoresis; multidimensional gel and capillary electrophoresis; mass spectroscopy, multidimensional mass spectroscopy with HPLC, ICP, Raman spectroscopy, particle, nanoparticles, and bead based detection, imaging, comprising fluorescence, IR, optical, or any other analytical systems well know to one in the art.

The integration of a complete sample-to-answer instrument incorporating the cartridge to prepare DNA samples from many inputs and sample types and a microchip-based capillary electrophoresis device for separation of DNA fragments is taught for DNA sequencing, fragment sizing, and forensics.

Example 6

Device with Four Processing Channels

Figure 45:
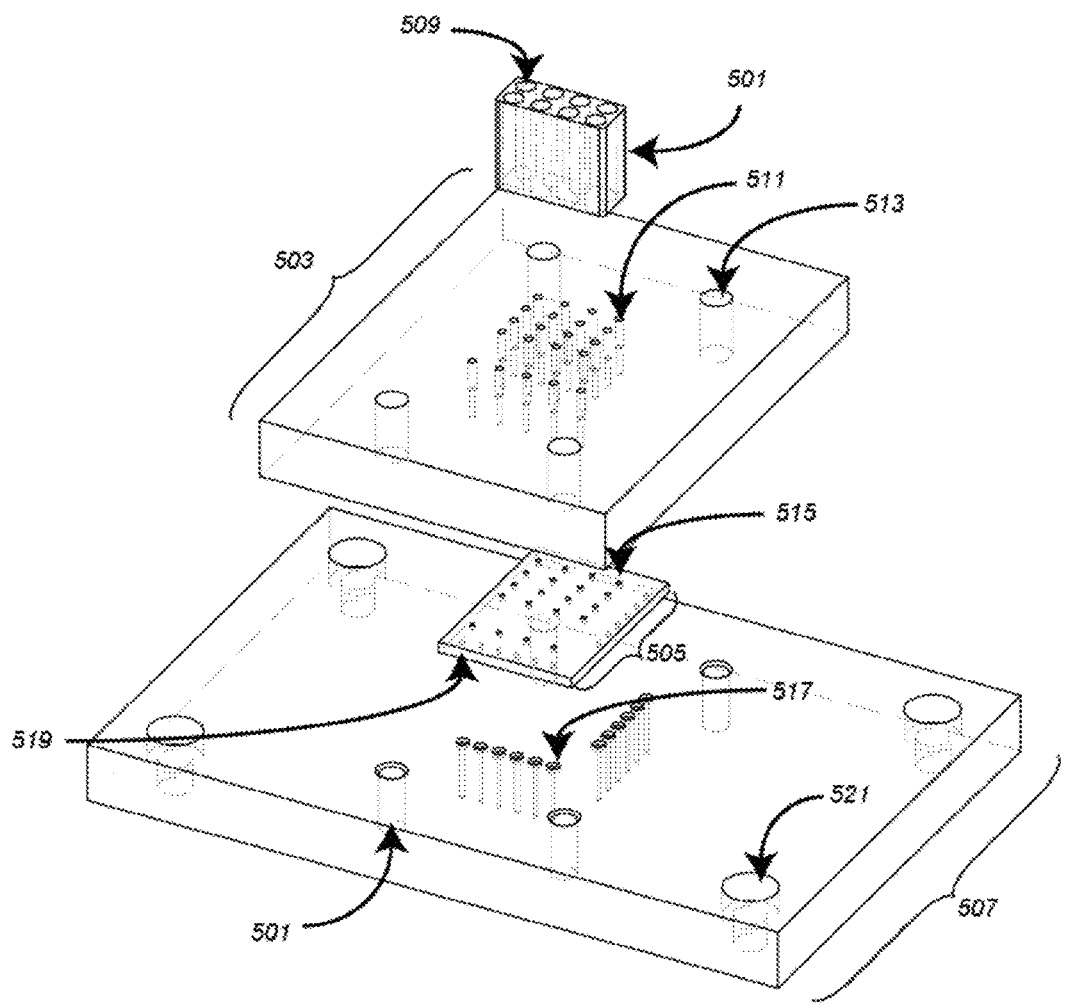
FIG. 45 depicts an expanded view of a heat block 509, a cartridge 50, a microfluidic microchip 519 and a pneumatics manifold 507.
Figure 46:
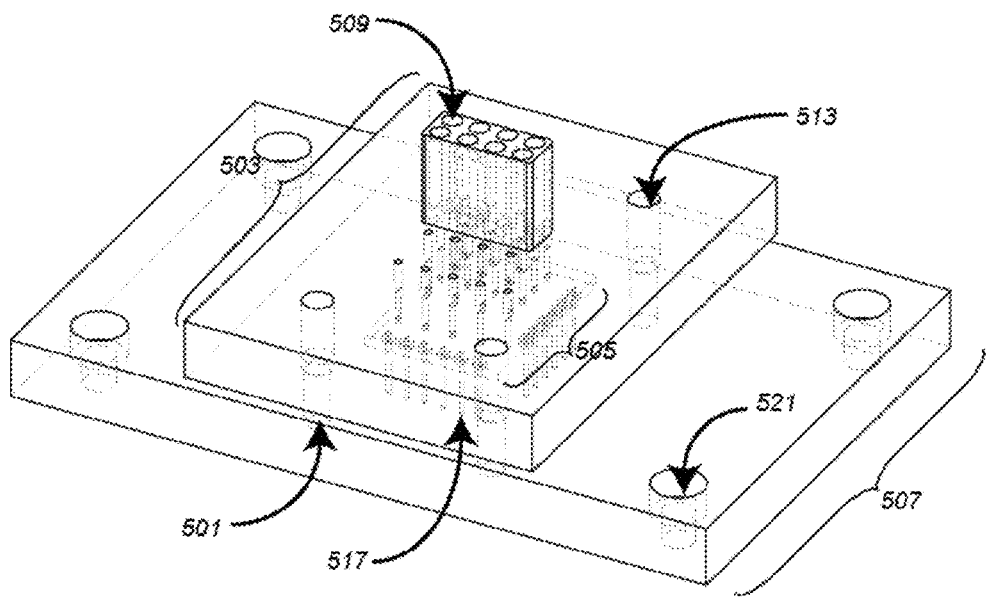
FIG. 46 depicts a heat block, a cartridge, a microfluidic microchip and a pneumatics manifold in an assembled form.

A microchip or microfluidic microchip can be used to amplify mRNA, concentrate nucleic acids on magnetic beads and inject purified samples into electrophoretic separation capillaries. As shown in FIG. 45 and FIG. 46, a microchip (505) can be interfaced with a cartridge (503) and a pneumatic manifold (507). FIG. 45 shows an expanded view of the microchip, cartridge, and pneumatic manifold. FIG. 46 shows a view of the cartridge interfaced with the microchip, which is interfaced with the pneumatic manifold. The cartridge can completely cover the surface of the microchip. Additionally, a block (501) has holes (509) that help to hold for incubation materials delivered to or from ports (511) of the cartridge (503). The block can be a heat block or a temperature controlling block. The holes (509) can be used to hold to hold pipette tips or be used as a large volume reactor or processor. The block (509) can be heated or cooled to control the temperature of material being delivered to cartridge and microchip or removed from the cartridge and microchip. The block can be in thermal contact with the cartridge. The ports of the cartridge can lead to reservoirs that are fluidically connected to ports that mate with ports (515) on the microchip (505). The microchip (505) can have pneumatic line ports (519) that mate with ports (517) of the pneumatic manifold. The ports of the pneumatic manifold can have o-ring gaskets that seal the pneumatic manifold to the microchip, allowing for high and low pressures to be delivered without leaking or with a reduced loss of pressure or vacuum. The cartridge, microchip, and pneumatic manifold can be held together using bolts or other securing objects that pass through openings (513, 501) of the cartridge and the pneumatic manifold.

A diagram of the Chip A microchip is shown in FIG. 47. The microchip comprises three layers: (i) a top fluidics layer (e.g., glass) carrying fluidic channels and wells, (ii) a bottom pneumatics layer (e.g., glass) carrying pneumatic channels and wells, and (iii) a middle flexible membrane, (e.g., 250 um thick, PDMS layer) (not shown). The PDMS membrane can be featureless. The PDMS membrane can deflect in response to positive or negative pressure applied to localized areas defined by the pneumatic channel system (dashed lines in FIG. 47). Pneumatic and fluidic channel etch depths are typically 50 um and can be designed to offer minimal hydraulic resistance. Valves in the microfluidic system can include pump valves. Pump valves can be larger than other valves, depending on the desired pump capacity, and can lack a valve seat. Removal of the valve seat can increase the pumping capacity, or the volume of fluid that is pumped per pump stroke. Other valves can be smaller, and have a valve seat that allows them to close firmly. Such reduced volume on/off valves can reduce the overall void space within the microfluidic microchip. Inlet and outlet valves can be such on/off valves.

As shown in FIG. 47, the microchip has four identical processing channels, each of which can control reagent flows for off-microchip or on-microchip magnetic-bead-based nucleic acid concentration and capillary electrophoresis sample injection. The four processing channels are fed by a common "reagent rail" which can select input reagents from four input wells (the fifth well can be used as a waste port). Individual samples can be fed into each processing channel from channel-specific sample wells, and can be processed in parallel (the microchip shown is a 4-plex processing device). Each processing channel can have a 0.8 μL, pump, sample input well, two output wells, and a waste well. Beads, such as magnetic beads, can be captured in any of the wells, e.g. one or both of the output wells. This output well can interface with the cartridge or fluidic manifold.

Figure 48:
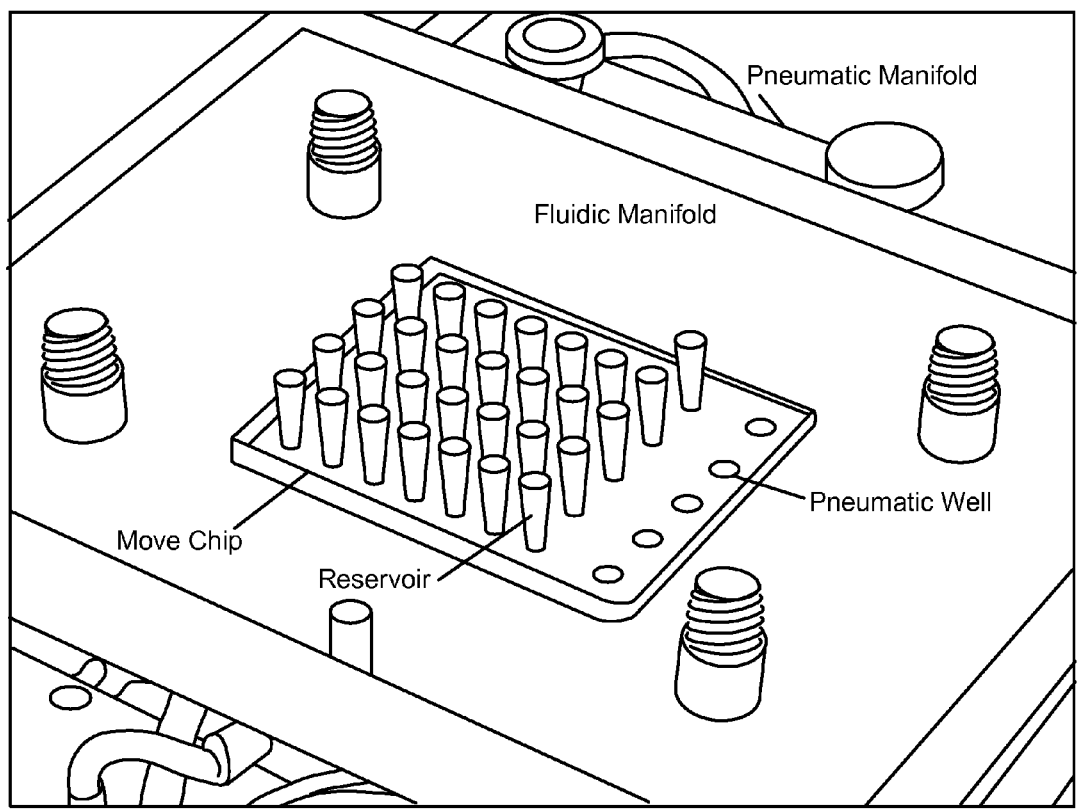
FIG. 48 depicts a cartridge for interfacing with a fluidics layer of a microfluidic microchip.

A photograph of the Chip A microchip, is shown in FIG. 48. The microchip can be mounted between a top fluidic manifold, mating fluid reservoirs to wells on the top surface of the microchip, and a bottom pneumatic manifold, mating pneumatic control lines to wells on the bottom surface of the microchip via o-ring seals. Microchip valves and pumps can be actuated by a pneumatic control system driven by computer scripts, such as DevLink scripts, or other software. The system can supply positive pressure (approximately +10 psi) to close valves, and/or negative pressure (approximately −20 psi or vacuum) to open them. The same pneumatic system can operate microchip pumps, with negative pressure acting to fill the pump bodies (on the fluidic channel side of an elastomeric layer), and positive pressure acting to empty them. As described herein, pumping action depends on the coordinated actions of pumps and flanking inlet and outlet valves.

Example 7 mRNA Amplification Using Device with Four Processing Channels

Chip A was used to perform the first, reverse transcription, reaction of the Eberwine protocol. Effective mixing and incubation methods were developed.

Figure 49:
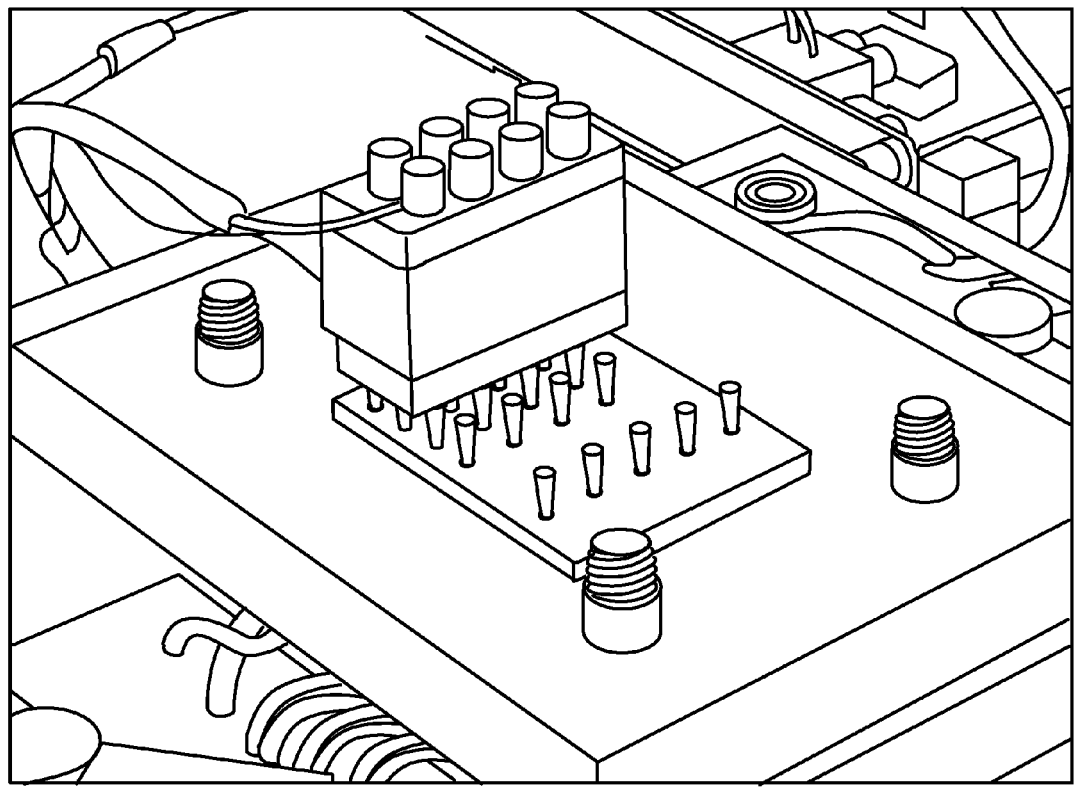
FIG. 49 depicts a block for holding tips that interface with a cartridge.

In order to provide temperature control for the approximately 10 ul reaction, a simple heated aluminum block (509), carrying eight 200 ul pipette tips, was fabricated and mated to the fluidic manifold as shown in FIG. 45, FIG. 46, and FIG. 49. Each pipette tip connected to a microchip output. In the experiment, only 4 tips, connected to microchip Output-1 wells (as indicated in FIG. 47), were actually used. Heating (50° C.) was accomplished with a thin-film heater attached to the outer surface of the block with adhesive. A thermocouple was inserted into the center of the block, and the heater was controlled with a DevLink PID control loop.

For mixing, a DevLink script was developed to mix samples and a reagent in a 1:1 ratio by alternately pumping approximately 0.6 ul from each respective reservoir into a pipette tip mated to Output-1. Experiments with food dye confirmed that alternate pumping effectively mixed the two components in the tip.

To perform the reaction, a mixture of total RNA and T7 Promoter-Primer (in water) was pipetted into sample well reservoirs, and a two-fold concentrated RT Mix, containing Superscript III reverse transcriptase, was pipetted into a reagent reservoir. After 15 ul had been loaded into the tips (12 pump cycles), the script terminated, and the reactions continued incubating for 15 minutes at 50° C. At this point the tips were removed, emptied into 0.2 ml PCR tubes, and the reactions terminated by incubation at 85° C. for 5 minutes in a thermocycler.

Positive control reactions were treated identically, except that these reactions were performed entirely at the bench and incubated 15 min at 50° C. in a thermocycler. Negative control reactions were mixed (at the bench) and immediately terminated by incubation for 5 min at 85° C.

Figure 50:
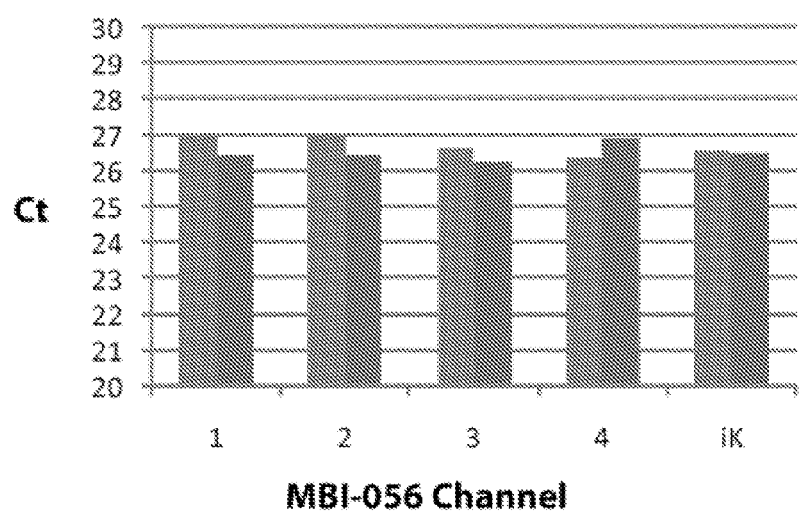
FIG. 50 depicts results of reverse transcription reactions of an mRNA amplification scheme.

Reactions were analyzed by TaqMan real-time quantitative PCR using a Gusb primer and probe set (ABI). The results are shown in FIG. 50 for 15 µL reactions containing approximately 500 ng total RNA (Rat Liver) and 10 U/µL Superscript III RT. Results from channels 1-4 are shown with results on the performed entirely at the bench indicated by iK. In FIG. 50, the pair of bars shown for each of channels 1, 2, 3, 4, and iK represent replicate reactions. The results showed that microchip and bench reactions were identical in their yield of first-strand Gusb cDNA. Both reactions produced Ct's between 26 and 27. Negative control reactions produced Ct>35 (data not shown).

Example 8

Device with Bead Clean-Up Chambers

Figure 51:
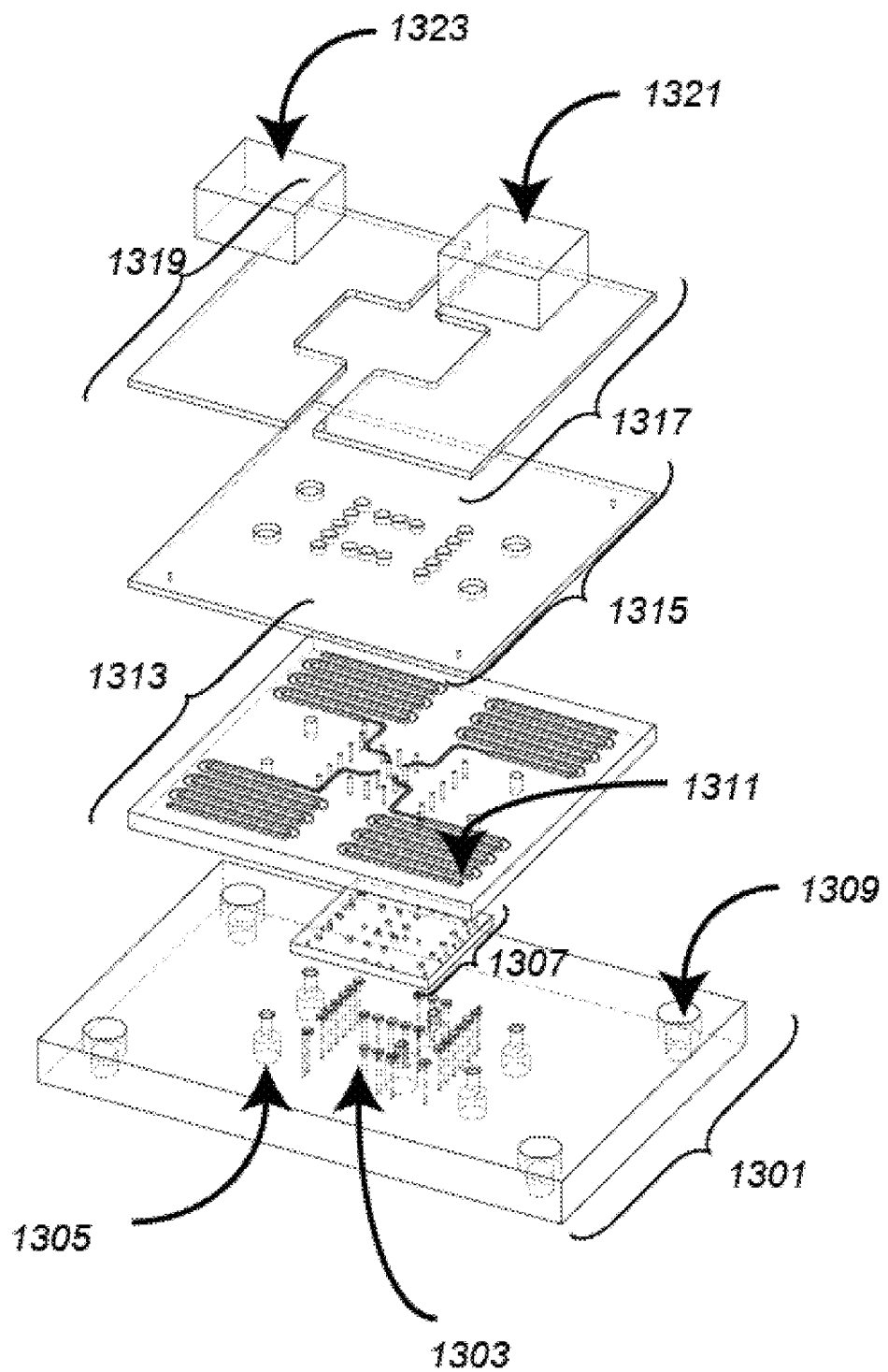
FIG. 51 depicts an expanded view of a heat block with a heat distributing element, a cartridge, a microfluidic microchip and a pneumatics manifold.
Figure 52:
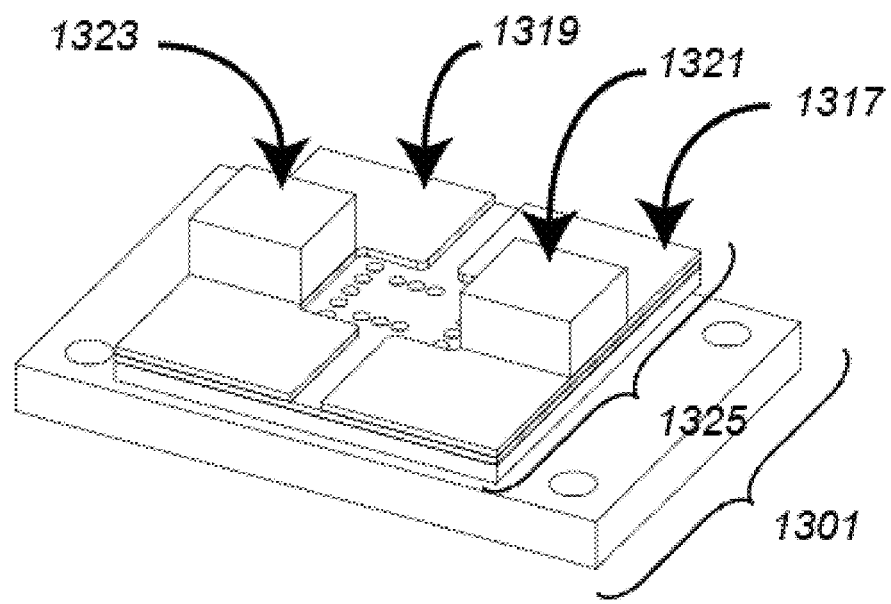
FIG. 52 depicts a heat block with a heat distributing element, a cartridge, a microfluidic microchip and a pneumatics manifold in an assembled form.
Figure 53:
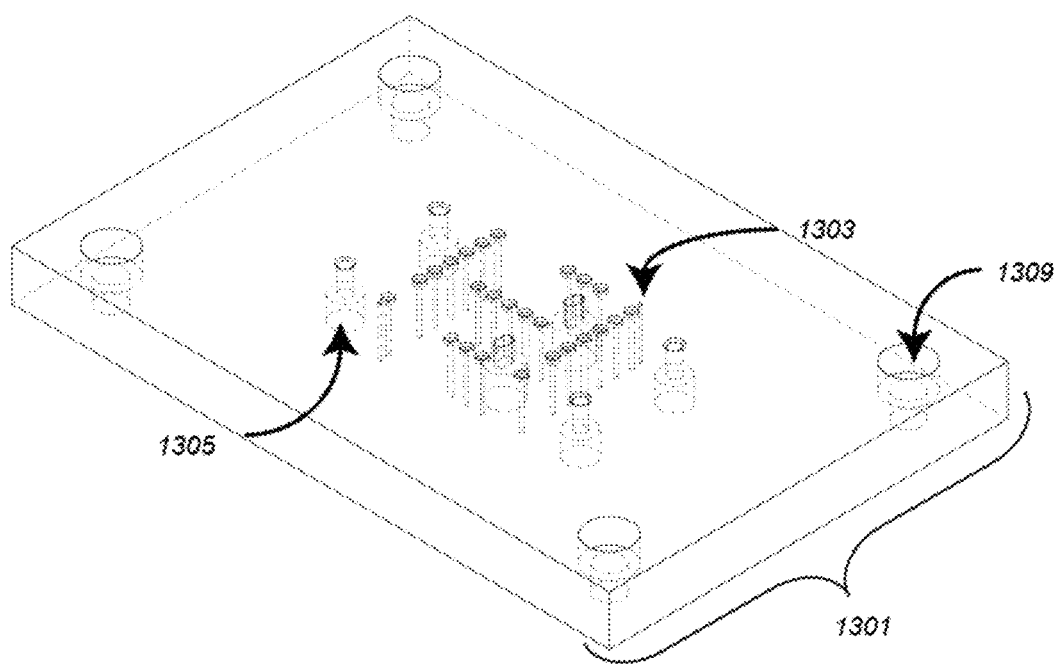
FIG. 53 depicts a pneumatics manifold.
Figure 54:
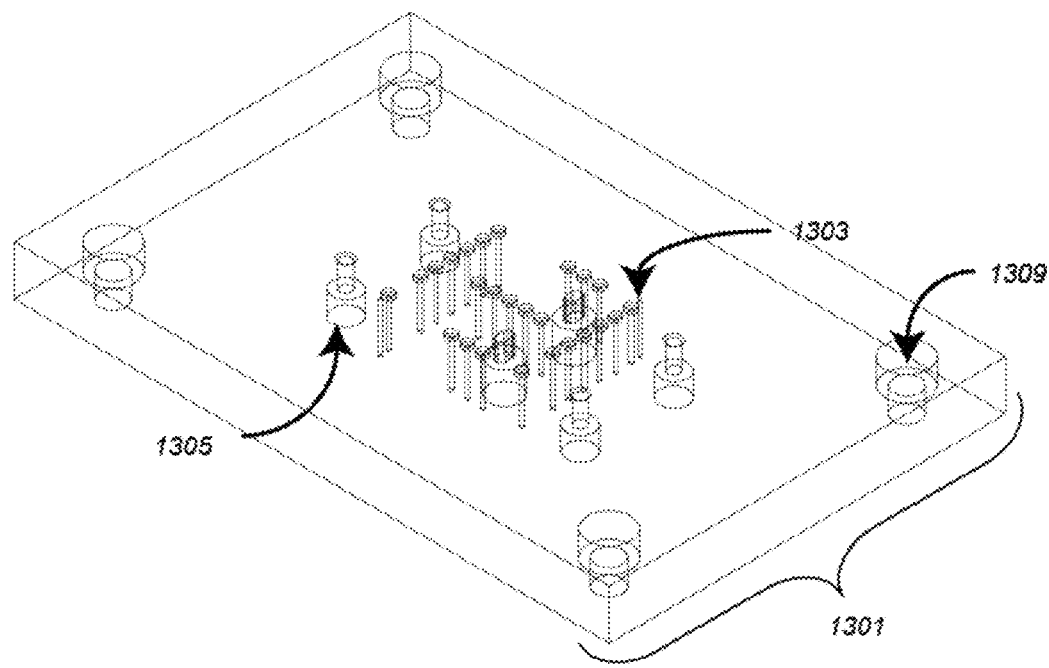
FIG. 54 depicts a pneumatics manifold.
Figure 55:
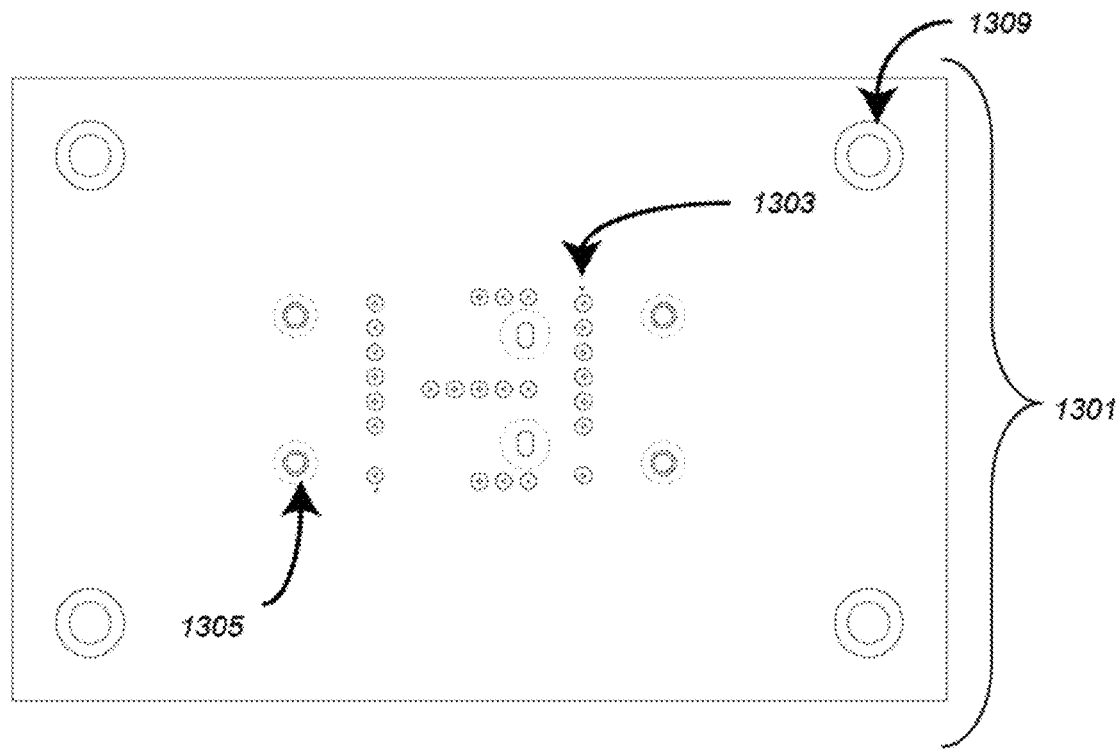
FIG. 55 depicts a pneumatics manifold.
Figure 56:
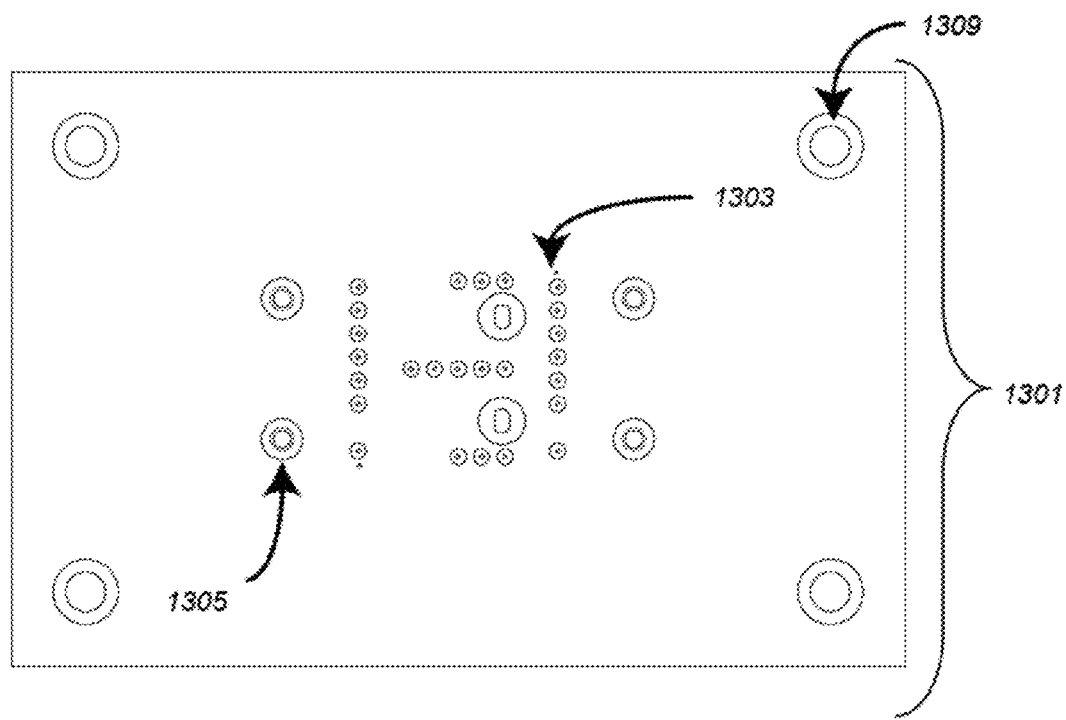
FIG. 56 depicts a pneumatics manifold.

A microchip or microfluidic microchip can be used to amplify mRNA, and to concentrate and purify nucleic acids on magnetic beads. FIG. 51 shows an expanded view of a device that has a microchip 1307 that can be interfaced with a cartridge made of two pieces 1313, 1315 and a pneumatic manifold 1301. The cartridge is made of a first piece that has serpentine channels 1311, wells, reservoirs, and chambers, and a second piece (1315) that has wells and chambers. The serpentine channels can be used to increase heat transfer between the heat distributing piece and a fluid contained within the serpentine channels. The second piece and first piece can be bonded together such that the serpentine channels are enclosed on a top side. The cartridge can be overlayed or in thermal contact with a heat distributing piece (1317) that distributes heat from thermal control blocks (1323, 1321). The thermal control blocks can be thermo electric coolers (TECs or Peltier devices), thin-film heaters, or other thermal control devices. The heat distributing piece and heat blocks may or may not be bonded or secured to the cartridge. Screws, bolts, and/or hinges may facilitate the securing of the heating distributing piece and/or heat blocks to the cartridge. FIG. 52 shows a view of the cartridge interfaced with the microchip, which is interfaced with the pneumatic manifold. The pneumatic block may have annular spaces (1305, 1309) for bolts and/or screws and ports (1303) that interface between pneumatic lines and the pneumatic layer of the microfluidic microchip. Additional views of the pneumatic layer are shown in FIG. 53, FIG. 54, FIG. 55, and FIG. 56. FIG. 53 and FIG. 55 show views with dashed lines indicating edges that are hidden from view. FIG. 53 and FIG. 54 show three dimensional views of the pneumatic layer. FIG. 55 and FIG. 56 show top views of the pneumatic layer.

Figure 57:
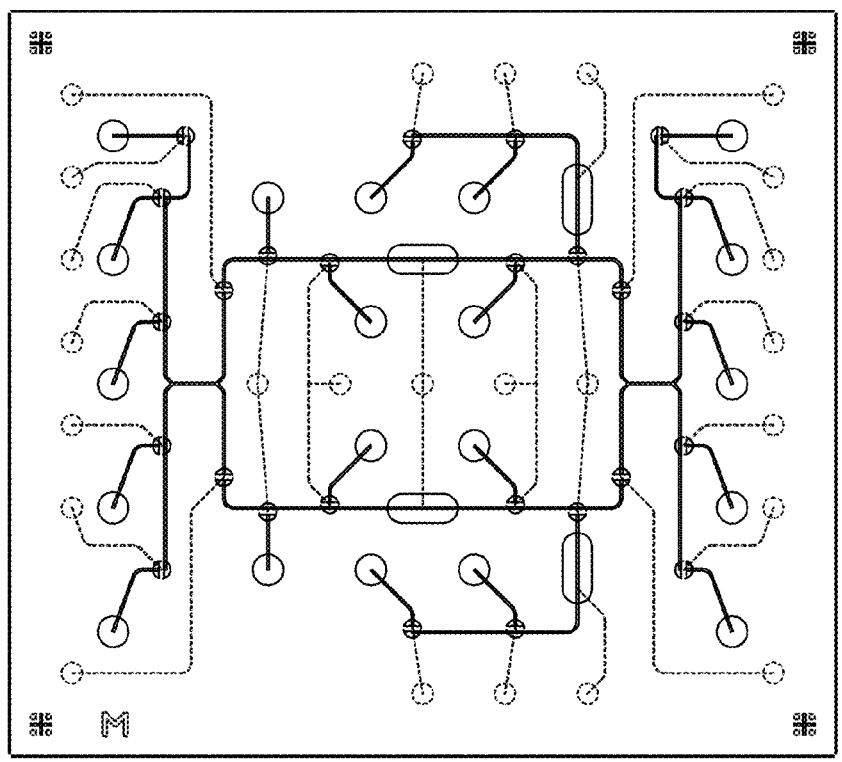
FIG. 57 depicts fluidics and pneumatic layers of a microfluidic microchip with a reagent and bead rail with the fluidic layer shown in solid lines and the pneumatics layer shown in dashed lines.
Figure 58:
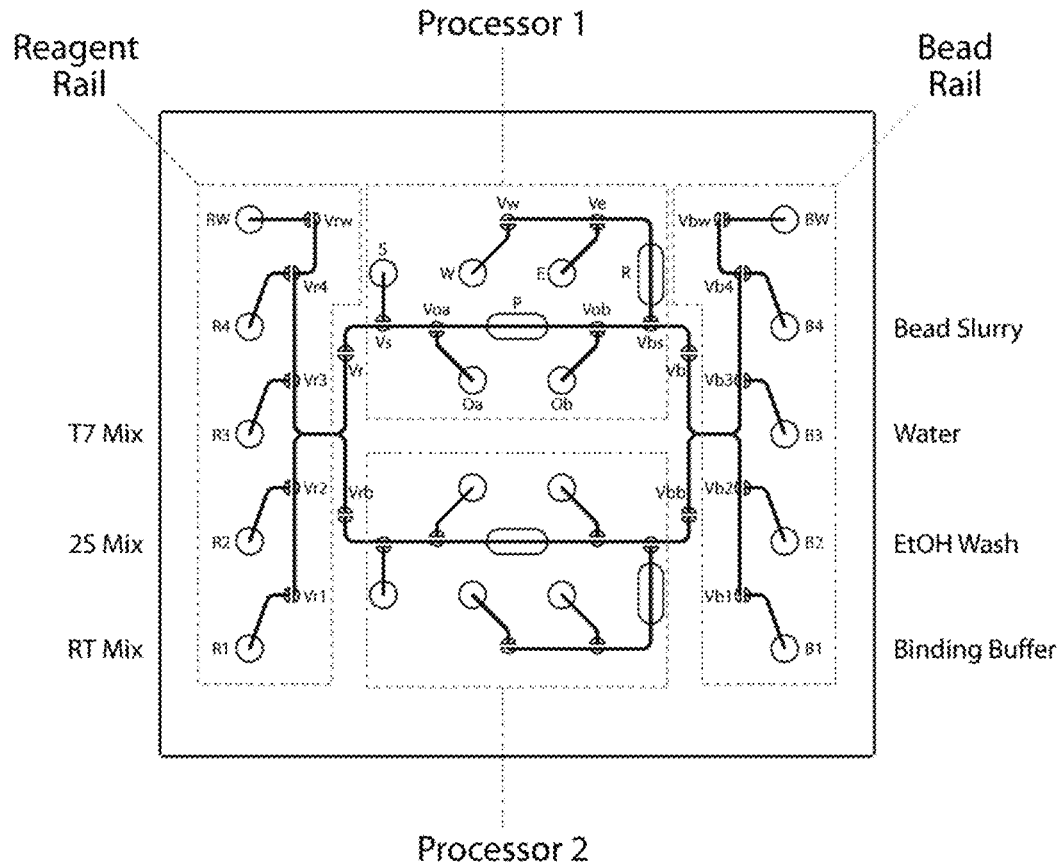
FIG. 58 depicts fluidics layers of a microfluidic microchip with a reagent and bead rail.

FIG. 57 and FIG. 58 show diagrams of a microfluidic microchip, the Chip B microchip, with bead clean-up chambers. Referring to FIG. 58, the microchip has four main sections: Reagent Rail, Bead Rail, Processor 1, and Processor 2. The two rails and the two processors have mirrored geometries. The microchip is configured so that either reagent rail may feed either processor. Access to the processors is controlled by valves Vr and Vb for the top processor and by valves Vrb and Vbb for the bottom processor. During reagent processing and enzymatic reactions of the top processor, Vr is opened and Vb is closed. During reagent processing and enzymatic reactions of the bottom processor, Vrb is opened and Vbb is closed. During clean-up, the reverse applies, that is, for the top processor Vr is closed and Vb is opened and for the bottom processor Vrb is closed and Vbb opened. It can be seen that the top and bottom processor can operate either in parallel or separately. Reagent and Bead Rail design closely follows the Chip A design. Each rail can access four different reagents (R1-4 and B1-4), via valves Vr1-4 and Vb1-4 respectively, and each rail has waste wells (RW and BW), accessed by valves Vrw and Vbw, respectively. Each processor has a sample input well (S), two output wells (Oa, Ob), and a bead side channel accessed by valves Vs, Voa, Vob, Vbs respectively. The bead side channel has a bead reservoir (R), and two valves (Vw and Ve) accessing waste (W) and elution (E) wells, respectively. Pneumatic lines and ports for control of the valves are shown as dashed in FIG. 57.

For purposes of explanation below, it is assumed that Processor 1 and Processor 2 are operated identically in parallel, and that Chip B is a duplex device, processing two samples simultaneously. For clarity, the operation of only the top processor is detailed. However, non-parallel operation is also possible. It is also assumed that wells Oa and Ob are connected to appropriate capacity reservoirs in a fluidic manifold or tubing. Reservoirs can be pipette tips, a reservoir in a cartridge, or connected by tubing to larger volumes The microfluidic microchip can have 75 µm channel depth, 250 µm (final) fluid channel width, and 0.6 µl (estimated) pumping stroke volume.

Referring to FIG. 58, a reaction comprising Reagent 1 and Sample may be assembled in well Oa by alternate 4-cycle pumping (A, B, C, D). Assume all valves are initially closed. In cycle A, valves Vr1 and Vr open, allowing pump P to draw Reagent 1 from well R1 with a down-stroke (negative pressure applied to pump P to open the valve). In cycle B, valves Vr1 and Vr close and valve Voa opens, allowing pump P to expel its contents (from R1 in this example) into well Oa with an up-stroke (positive pressure applied to pump P to close it). In cycle C, valve Vs opens and valve Voa closes, allowing pump P to draw Sample from well S with a down-stroke. In cycle D, valve Vs closes and Voa opens, allowing pump P to expel its contents into well Oa with an up-stroke. These four cycles are repeated until a sufficient volume has been pushed into Oa. The mixing ratio between Sample and Reagent 1 is determined by the ratio of cycles AB:CD. In the process described above, the mixing ratio is 1:1, but it can in principle be any value. Finally, similar procedures can be used to mix any of the reagents (R1-4) with sample S, by substituting the appropriate valve for Vr1. Referring to FIG. 58, in 4-cycle pumping, the fluid can be pumped in a first direction from a first source well to a space within a pumping valve in the first step. In the second step, the fluid can be pumped in a direction opposite to the first direction by moving the fluid from the pumping valve to a mixing well. The third and fourth steps can be repeated with a second source well instead of the first source well. The pumping in opposite directions to obtain mixing in the mixing well can be a result of having the source well, mixing well, and pumping valve positioned along a channel such that the pumping valve is not located between the source well and the mixing well. This configuration can reduce the dead space within the microfluidic microchip, improve mixing, or improve uniformity of reagent and sample handling. As well, this configuration can allow for a central pump to move liquid between many different wells on a microfluidic microchip through the opening and closing of appropriate valves.

The valves shown in FIG. 57 and FIG. 58 and any other valve shown herein sometimes are placed at T-shaped junctions. The valves can close off flow from one channel of the T to the other two channels leading into the T, while continuing to allow flow between the other two channels. For example, closing valve Voa prevents fluid from flowing from pump P to Oa, but does not prevent fluid from flowing from pump P to S if valve Vs is open. Alternatively, a valve can obstruct flow between all channels leading into the T. The same can be applied to valves that are placed at junctions of 4, 5, 6, or more channels. The valves can also be replaced by valves that are only in the reagent or bead channel as needed.

Example 9 mRNA Amplification Using Device with Bead Clean-Up Chambers

As described above, the Eberwine mRNA amplification procedure is a cascade of three binary additions. To execute the Eberwine sequence, R1 contains RT Mix, R2 contains 2S (second-strand) Mix, and R3 contains T7 Mix, as shown in FIG. 58. A two-fold (2×) volume of 2S Mix can be added to the RT reaction, and a one-fold volume of T7 Mix can be added to the 2S reaction, as shown in FIG. 44. This requires a 2:1 pumping ratio (AB:CD) for the 2S Mix addition, and a 1:1 ratio for the T7 Mix addition.

The first (RT) reaction with a 1:1 mixture of total RNA+ Primer, from well S, and 2×RT Mix, from well R1, can be formed using the methods described herein. After an appropriate incubation period, the second-strand reaction may be assembled in well Ob by drawing from well Oa (rather than well S), and drawing from well R2 (rather than from well R1). A four-cycle pumping scheme (A, B, C, D) similar to that described in Example 8 can be used. In cycle A, Vr2 opens rather than Vr1; in cycle B, Vob opens rather than Voa; in cycle C, Voa opens rather than Vs; and in cycle D, Vob opens rather than Voa. To obtain the required 2:1 mixing ratio, two cycles can draw from R2 for every cycle drawing from Oa.

After another appropriate incubation period, the third (T7) reaction may be assembled in well Oa with a similar process (drawing from R3 and Ob, 1:1 ratio). Thus the final T7 reaction can reside in Oa. After an appropriate incubation period, aRNA can be ready for purification.

Purification involves operation of the Bead Rail rather than the Reagent Rail. Thus, during this phase of microchip operation, valve Vr remains closed and Vb can open.

To purify aRNA, reservoir R must first be loaded with magnetic beads. This may be accomplished with a 2-cycle procedure, similar to that of cycles A and B of Example 8, except that input to pump P can be via valves Vb4 and Vb (cycle A), and output from pump P can be via valves Vbs and Vw (cycle B). This sequence can draw bead slurry from well B4 into pump P, and expel bead slurry from pump P through reservoir R into waste well W. As the slurry passes through reservoir R, beads can be captured by a magnet placed below reservoir R.

Before aRNA (in well Oa) can be captured, it must be mixed with Binding Buffer. This can be accomplished with another 4-cycle procedure, similar to that in Example 8, except that Binding Buffer can be drawn from well B1 in the Bead Rail, and the mixture can accumulate in well Ob.

aRNA in well Ob can then be captured by beads in reservoir R by pumping the contents of well Ob through reservoir R out into waste well W. This can be accomplished with a 2-cycle procedure in which pump P is filled via valve Vob (cycle A) and emptied via valves Vbs and Vw (cycle B).

Loaded beads can then be washed with ethanol pumped from well B2. This can be accomplished with a 2-cycle procedure in which pump P is filled via valves Vb2 and Vb (cycle A) and emptied via valves Vbs and Vw (cycle B). After ethanol from well B2 has been exhausted, pumping can continue to draw air over the beads to dry them.

Finally, aRNA can be eluted from the beads into well E by pumping water through reservoir R with a 2-cycle procedure in which pump P is filled via valves Vb3 and Vb (cycle A) and emptied via valves Vbs and Ve (cycle B).

Example 10

Short RNA Amplification Using Device with Real-Time PCR Detection

MicroRNA (miRNA) are short (19-25 nucleotide) single-stranded RNAs that are produced by processing larger RNAs, while siRNA are short (20-25 nucleotide) double-stranded RNAs that are also produced by processing larger RNAs. miRNAs have been implicated in regulating translation of mRNA while siRNAs can silence or activate transcription of genes. Both miRNA and siRNA, collectively small RNAs, can be assayed using the devices described herein. To assay either small RNA, the device in FIG. 58 would be reconfigured with 1) R3 containing a mixture to polyadenylate the short RNA, 2) R4 containing real-time PCR primers and real-time master mix, and 3) the RT mixture in R1 can contain a polyT sequence with a 5' sequence for real-time PCR amplification instead of a T7 promoter. The reaction would proceed as described in Example 9 except first a polyA tail would be added to the small RNAs to produce polyadenylated small RNAs using R3 as the reagent source. The reverse transcription and second strand synthesis can operate as described in Example 9. The final step of T7 transcription is then replaced by mixing the real time PCR primers and master mix from R4 with the second strand product. The real time PCR primers are then amplified using PCR with real time detection. The amplification can occur off-microchip or a detector and thermal cycling can be incorporated on the microchip or in heating block (509). Real time PCR on microchips was previously described, e.g. Jovanovich, S., I. Blaga, and D. Rank. Microfluidic Devices. US Patent Publication No. 2007/0248958 and PCT Publication No. WO/2006/032044, which are hereby incorporated by reference. It will be obvious to one skilled in the art that other mRNAs can be processed as described in this example by omitting the polyadenylation step.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, any MOVe valve, pump, router, or other MOVe device described herein can be replaced with any pneumatically actuated valve, pump router or other device. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method for generating short tandem repeat (STR) profiles on each of a plurality of samples comprising, for each sample:
   a) isolating DNA from the sample by:
      delivering a lysis buffer into a lysis chamber of a cartridge, wherein the lysis chamber contains a swab or swipe containing human cells from the sample, to produce a lysate, wherein the cartridge is configured as a disposable single-use device;
      transporting the lysate from the cartridge through a microfluidic channel in a microfluidic microchip to which the cartridge is mated and into a DNA isolation chamber comprising paramagnetic beads in the cartridge, wherein the microfluidic channel
   comprises at least one valve that controls movement of a fluid through the channel;
      binding the DNA onto the beads;
      applying a magnetic field to a side of the DNA isolation chamber to capture the paramagnetic beads; and
      washing the beads, to produce purified DNA bound to the beads;
   b) amplifying STR markers by:
      moving the purified DNA bound to the beads through a microfluidic channel in the microfluidic microchip to a reaction chamber of a thermocycler wherein the reaction chamber is in thermal contact with a temperature modulator, and wherein the reaction chamber is off-chip;
      capturing purified DNA bound to the beads in the reaction chamber of the thermocycler by applying a magnetic field;
      moving reagents for STR amplification to the reaction chamber of the thermocycler;
      performing PCR in the reaction chamber of the thermocycler to amplify STRs to produce amplification product;
   and
   c) analyzing the amplification product by:
      moving the amplification product to a loading channel, wherein the loading channel intersects a gel-filled separation channel, and wherein a cathode and an anode are configured to apply a voltage across the loading channel and the separation channel;
      injecting amplification product from the loading channel into the separation channel by applying a voltage across the cathode and the anode;
      performing electrophoresis on the amplification product in the separation channel to separate analytes in the amplification product; and
      generating an STR profile of the sample from the separation;
   wherein all the method is performed on each sample in parallel on an integrated system using software that automates the process.

2. The method of claim 1, wherein separation obtains single base pair resolution out to approximately 330 base pairs in less than 20 minutes.

3. The method of claim 1, wherein isolating DNA from the sample is performed in less than 5 minutes.

4. The method of claim 1, wherein the method is performed on at least 4 samples.

5. The method of claim 1, wherein the magnetic field is applied to the side of the DNA isolation chamber using a movable magnet.

6. The method of claim 1, wherein the cartridge and the microfluidic microchip are clamped together.

7. The method of claim 1, wherein the temperature modulator is a Peltier device.

8. The method of claim 1, wherein the thermocycler further comprises a heat distributing element between the reaction chamber and the temperature modulator.

9. The method of claim 1, wherein the at least one valve is a diaphragm valve that comprises an elastomeric layer and a seat, wherein the valve obstructs flow through the channel when the elastomeric layer is in contact with the seat.

10. The method of claim 9, wherein the at least one diaphragm valve comprises an elastomeric layer that is normally not in contact with the seat.

11. The method of claim 1, wherein the microfluidic channel comprises at least three valves that control movement of a fluid through the channel.

12. The method of claim 1, wherein delivering the lysis buffer into a lysis chamber of the cartridge comprises using an external pressure source.

13. The method of claim 1, wherein moving reagents for STR amplification to the thermocycler comprises using an external pressure source.

14. The method of claim 1, wherein performing PCR in the thermocycler produces a labeled amplification product.

15. The method of claim 14, wherein the labeled amplification product is fluorescently labeled.

16. The method of claim 1, wherein moving the amplification product to the loading channel comprises eluting the amplification product from the beads.

17. The method of claim 1, wherein injecting amplification product from the loading channel into the separation channel comprises field amplified sample stacking.

18. The method of claim 1, wherein injecting amplification product from the loading channel into the separation channel comprises applying a voltage of about 25 to 500 V/cm.

19. The method of claim 1, wherein the microfluidic microchip comprises a fluidics layer, an actuation layer, and a pneumatics layer, and wherein the fluidics layer is adjacent to the cartridge.

20. The method of claim 1, wherein the separation channel comprises a capillary.

21. The method of claim 20, wherein the capillary has an outer diameter of about 150-500 microns and an inner diameter of about 10-100 microns.

22. The method of claim 1, wherein generating the STR profile comprises detecting the analytes in the separation channel, wherein detecting the analytes is performed using a light source and a photodetector.

23. The method of claim 22, wherein the photodetector comprises a CCD.

24. The method of claim 22, wherein the photodetector comprises a CMOS.

25. The method of claim 22, wherein the photodetector comprises a photomultiplier tube (PMT).

26. The method of claim 22, wherein the light source comprises a coherent light source.

27. The method of claim 26, wherein the coherent light source comprises a laser.

\* \* \* \* \*

UNITED STATES PATENT AND TRADEMARK OFFICE
CERTIFICATE OF CORRECTION

| | | |
|---|---|---|
| PATENT NO. | : 8,748,165 B2 | Page 1 of 1 |
| APPLICATION NO. | : 13/590965 | |
| DATED | : June 10, 2014 | |
| INVENTOR(S) | : Mattias Vangbo et al. | |

It is certified that error appears in the above-identified patent and that said Letters Patent is hereby corrected as shown below:

On the title page, at item (75) Inventors, please replace "Steven B. Jovanovich" with
-- Stevan B. Jovanovich --.

Signed and Sealed this
Sixteenth Day of June, 2015

Michelle K. Lee
*Director of the United States Patent and Trademark Office*